(12) United States Patent
Fish et al.

(10) Patent No.: US 10,201,388 B2
(45) Date of Patent: *Feb. 12, 2019

(54) GRAPHICAL USER INTERFACE FOR REAL-TIME RF LESION DEPTH DISPLAY

(71) Applicant: St. Jude Medical, Atrial Fibrillation Division, Inc., St. Paul, MN (US)

(72) Inventors: Jeffrey M. Fish, Maple Grove, MN (US); Israel A. Byrd, Richfield, MN (US); Jeremy D. Dando, Plymouth, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 299 days.

This patent is subject to a terminal disclaimer.

(21) Appl. No.: 15/275,530

(22) Filed: Sep. 26, 2016

(65) Prior Publication Data

US 2017/0065348 A1 Mar. 9, 2017

Related U.S. Application Data

(63) Continuation of application No. 12/963,257, filed on Dec. 8, 2010, now Pat. No. 9,492,226, which is a
(Continued)

(51) Int. Cl.
*A61B 18/12* (2006.01)
*A61B 34/10* (2016.01)
(Continued)

(52) U.S. Cl.
CPC .......... *A61B 34/10* (2016.02); *A61B 18/1492* (2013.01); *A61B 34/25* (2016.02);
(Continued)

(58) Field of Classification Search
CPC . A61B 18/14; A61B 18/1492; A61B 18/1233; A61B 19/56; A61B 19/5225;
(Continued)

(56) References Cited

U.S. PATENT DOCUMENTS 2,184,511 A 12/1939 Bagno et al.
3,316,896 A 5/1967 Thomasset
(Continued)

FOREIGN PATENT DOCUMENTS

EP 1472976 11/2004
EP 1586281 4/2009
(Continued)

OTHER PUBLICATIONS

Author: Gales, Rosemary Title: Use of bioelectrical impedance analysis to assess body composition of seals Citation: Marine Mammal Science, vol. 10, Issue 1, Abstract Publication Date: Aug. 26, 2006.
(Continued)

*Primary Examiner* — Daniel W Fowler
(74) *Attorney, Agent, or Firm* — Dykema Gossett PLLC

(57) ABSTRACT

A system for displaying characteristics of target tissue during an ablation procedure is provided that includes an electronic control unit (ECU) configured to receive data regarding electrical properties of the target tissue for a time period. The ECU is also configured to determine a value responsive to the data and indicative of at least one of a predicted depth of a lesion in the target tissue, a predicted temperature of the target tissue, and a likelihood of steam pop of the target tissue for the time period. The system further includes a display device operatively connected to the ECU. The display device is configured to receive the value and display a visual representation indicative of at least one of a predicted depth of a lesion in the target tissue, a predicted temperature of the target tissue, and a likelihood of steam pop of the target tissue for the time period.

19 Claims, 27 Drawing Sheets

Related U.S. Application Data continuation-in-part of application No. 12/946,941, filed on Nov. 16, 2010, now Pat. No. 8,603,084, which is a continuation-in-part of application No. 12/622,488, filed on Nov. 20, 2009, now Pat. No. 8,403,925, which is a continuation-in-part of application No. 12/253,637, filed on Oct. 17, 2008, now Pat. No. 8,449,535, which is a continuation-in-part of application No. 12/095,688, filed as application No. PCT/US2006/061714 on Dec. 6, 2006, now Pat. No. 9,271,782, which is a continuation-in-part of application No. 12/353,897, filed on Jan. 14, 2009, which is a continuation-in-part of application No. 12/253,637, filed on Oct. 17, 2008, now Pat. No. 8,449,535, which is a continuation-in-part of application No. 12/095,688, filed on May 30, 2008, now Pat. No. 9,271,782.

(60) Provisional application No. 60/748,234, filed on Dec. 6, 2005, provisional application No. 61/020,806, filed on Jan. 14, 2008, provisional application No. 61/177,876, filed on May 13, 2009.

(51) Int. Cl.
  *A61B 18/14* (2006.01)
  *A61B 34/00* (2016.01)
  *A61B 17/00* (2006.01)
  *A61B 18/00* (2006.01)
  *A61B 34/30* (2016.01)
  *A61B 90/00* (2016.01)

(52) U.S. Cl.
  CPC .......... *A61B 34/73* (2016.02); *A61B 18/1233* (2013.01); *A61B 18/14* (2013.01); *A61B 2017/00084* (2013.01); *A61B 2017/00256* (2013.01); *A61B 2018/00178* (2013.01); *A61B 2018/00577* (2013.01); *A61B 2018/00702* (2013.01); *A61B 2018/00791* (2013.01); *A61B 2018/00803* (2013.01); *A61B 2018/00875* (2013.01); *A61B 2018/00886* (2013.01); *A61B 2034/104* (2016.02); *A61B 2034/105* (2016.02); *A61B 2034/301* (2016.02); *A61B 2090/062* (2016.02); *A61B 2090/065* (2016.02)

(58) Field of Classification Search
  CPC .... A61B 2017/00256; A61B 2019/462; A61B 2019/465; A61B 2019/504; A61B 5/01; A61B 5/06; A61B 5/4848; A61B 5/6885–5/6886; A61B 2018/00178; A61B 2018/00648; A61B 2018/00773; A61B 2018/00875; A61B 2018/00904
  See application file for complete search history.

(56) References Cited

U.S. PATENT DOCUMENTS

| | | |
|---|---|---|
| 3,949,736 A | 4/1976 | Vrana et al. |
| 4,641,649 A | 2/1987 | Walinsky |
| 5,230,349 A | 7/1993 | Langberg |
| 5,257,635 A | 11/1993 | Langberg |
| 5,297,549 A | 3/1994 | Beatty |
| 5,311,866 A | 5/1994 | Kagan |
| 5,341,807 A | 8/1994 | Nardella |
| 5,366,896 A | 11/1994 | Margrey et al. |
| 5,423,808 A | 6/1995 | Edwards |
| 5,429,131 A | 7/1995 | Scheinman |
| 5,447,529 A | 9/1995 | Marchlinski |
| 5,462,544 A | 10/1995 | Saksena et al. |
| 5,546,940 A | 8/1996 | Panescu et al. |
| 5,562,721 A | 10/1996 | Marchlinski |
| 5,582,609 A | 12/1996 | Swanson |
| 5,588,432 A | 12/1996 | Crowley |
| 5,630,034 A | 5/1997 | Oikawa |
| 5,657,755 A | 8/1997 | Desai |
| 5,659,624 A | 8/1997 | Fazzari |
| 5,673,704 A | 10/1997 | Marchlinski |
| 5,688,267 A | 11/1997 | Panescu |
| 5,697,377 A | 12/1997 | Wittkampf |
| 5,702,386 A | 12/1997 | Stern et al. |
| 5,718,241 A | 2/1998 | Ben-Haim |
| 5,722,402 A | 3/1998 | Swanson |
| 5,730,127 A | 3/1998 | Avitall |
| 5,759,159 A | 6/1998 | Masreliez |
| 5,782,900 A | 7/1998 | de la Rama |
| 5,800,350 A | 9/1998 | Coppleson |
| 5,810,742 A | 9/1998 | Pearlman |
| 5,814,043 A | 9/1998 | Shapeton |
| 5,836,943 A | 11/1998 | Miller, III |
| 5,836,990 A | 11/1998 | Li |
| 5,837,001 A | 11/1998 | Mackey |
| 5,846,238 A | 12/1998 | Jackson et al. |
| 5,904,709 A | 5/1999 | Arndt |
| 5,944,022 A | 8/1999 | Nardella |
| 5,954,665 A | 9/1999 | Ben-Haim |
| 6,001,093 A | 12/1999 | Swanson |
| 6,019,757 A | 2/2000 | Scheldrup |
| 6,026,323 A | 2/2000 | Skladnev |
| 6,035,341 A | 3/2000 | Nunally |
| 6,063,078 A | 5/2000 | Wittkampf |
| 6,129,669 A | 10/2000 | Panescu et al. |
| 6,171,304 B1 | 1/2001 | Netherly |
| 6,179,824 B1 | 1/2001 | Eggers |
| 6,206,874 B1 | 3/2001 | Ubby |
| 6,217,574 B1 | 4/2001 | Webster |
| 6,217,576 B1 | 4/2001 | Tu |
| 6,221,070 B1 | 4/2001 | Tu |
| 6,226,542 B1 | 5/2001 | Reisfeld |
| 6,233,476 B1 | 5/2001 | Strommer |
| 6,246,896 B1 | 6/2001 | Dumoulin et al. |
| 6,256,540 B1 | 7/2001 | Panesou |
| 6,322,558 B1 | 11/2001 | Taylor et al. |
| 6,337,994 B1 | 1/2002 | Stoianovici |
| 6,391,024 B1 | 5/2002 | Sun |
| 6,423,057 B1 | 7/2002 | He et al. |
| 6,427,089 B1 | 7/2002 | Knowlton |
| 6,443,894 B1 | 9/2002 | Sumanaweera |
| 6,445,952 B1 | 9/2002 | Manrodt |
| 6,456,864 B1 | 9/2002 | Swanson |
| 6,471,693 B1 | 10/2002 | Carroll |
| 6,475,215 B1 | 11/2002 | Tanrisever |
| 6,486,271 B1 | 11/2002 | Sosa et al. |
| 6,490,474 B1 | 12/2002 | Willis |
| 6,498,944 B1 | 12/2002 | Ben-Haim |
| 6,507,751 B2 | 1/2003 | Blume |
| 6,511,478 B1 | 1/2003 | Burnside |
| 6,546,270 B1 | 4/2003 | Goldin et al. |
| 6,558,382 B2 | 5/2003 | Jahns et al. |
| 6,569,160 B1 | 5/2003 | Goldin |
| 6,575,969 B1 | 6/2003 | Rittman, III |
| 6,605,082 B2 | 8/2003 | Hareyama |
| 6,652,518 B2 | 11/2003 | Wellman |
| 6,663,622 B1 | 12/2003 | Foley et al. |
| 6,676,654 B1 | 1/2004 | Balle-Petersen et al. |
| 6,683,280 B1 | 1/2004 | Wofford |
| 6,690,963 B2 | 2/2004 | Ben-Haim |
| 6,696,844 B2 | 2/2004 | Wong |
| 6,712,074 B2 | 3/2004 | Edwards |
| 6,743,225 B2 | 6/2004 | Sanchez |
| 6,755,790 B2 | 6/2004 | Stewart |
| 6,780,182 B2 | 8/2004 | Bowman |
| 6,788,967 B2 | 9/2004 | Ben-Haim |
| 6,813,515 B2 | 11/2004 | Hashimshony |
| 6,840,938 B1 | 1/2005 | Morley et al. |
| 6,917,834 B2 | 7/2005 | Koblish et al. |
| 6,918,876 B1 | 7/2005 | Kamiyama |
| 6,926,669 B1 | 8/2005 | Stewart |
| 6,936,047 B2 | 8/2005 | Nasab |
| 6,950,689 B1 | 9/2005 | Willis |

(56) References Cited

U.S. PATENT DOCUMENTS

| | | |
|---|---|---|
| 6,964,867 B2 | 11/2005 | Downs |
| 6,965,795 B2 | 11/2005 | Rock |
| 6,993,384 B2 | 1/2006 | Bradley |
| 7,041,095 B2 | 5/2006 | Wang et al. |
| 7,041,096 B2 | 5/2006 | Malis |
| 7,106,043 B1 | 9/2006 | Da Silva |
| 7,197,354 B2 | 3/2007 | Sobe |
| 7,248,032 B1 | 7/2007 | Hular |
| 7,263,395 B2 | 8/2007 | Chan |
| 7,263,397 B2 | 8/2007 | Hauck |
| 7,386,339 B2 | 6/2008 | Strommer |
| 7,497,858 B2 | 3/2009 | Chapelon |
| 7,499,745 B2 | 3/2009 | Littrup |
| 7,536,218 B2 | 5/2009 | Govari |
| 7,565,613 B2 | 7/2009 | Forney |
| 7,610,078 B2 | 10/2009 | Willis |
| 7,633,502 B2 | 12/2009 | Willis |
| 7,671,871 B2 | 3/2010 | Gonsalves |
| 7,776,034 B2 | 8/2010 | Kampa |
| 7,819,870 B2 | 10/2010 | Thao et al. |
| 7,865,236 B2 | 1/2011 | Cory |
| 7,904,174 B2 | 3/2011 | Hammill |
| 7,925,349 B1 | 4/2011 | Wong et al. |
| 7,953,495 B2 | 5/2011 | Sommer |
| 8,075,498 B2 | 12/2011 | Leo et al. |
| 8,403,925 B2 | 3/2013 | Miller et al. |
| 2001/0034501 A1 | 10/2001 | Tom |
| 2001/0039413 A1 | 11/2001 | Bowe |
| 2001/0047129 A1 | 11/2001 | Hall |
| 2001/0051774 A1 | 12/2001 | Littrup et al. |
| 2002/0013537 A1 | 1/2002 | Rock |
| 2002/0022836 A1 | 2/2002 | Goble |
| 2002/0049375 A1 | 4/2002 | Strommer et al. |
| 2002/0068931 A1 | 6/2002 | Wong |
| 2002/0072686 A1 | 6/2002 | Hoey et al. |
| 2002/0077627 A1 | 6/2002 | Johnson et al. |
| 2002/0120188 A1 | 8/2002 | Brock et al. |
| 2002/0123749 A1 | 9/2002 | Jain |
| 2002/0151887 A1 | 10/2002 | Stern et al. |
| 2002/0177847 A1 | 11/2002 | Long |
| 2003/0004587 A1 | 1/2003 | Joseph et al. |
| 2003/0028183 A1 | 2/2003 | Sanchez et al. |
| 2003/0045871 A1 | 3/2003 | Jain et al. |
| 2003/0060696 A1 | 3/2003 | Skladnev et al. |
| 2003/0065364 A1 | 4/2003 | Wellman |
| 2003/0093067 A1 | 5/2003 | Panescu |
| 2003/0093069 A1 | 5/2003 | Panescu |
| 2003/0100823 A1 | 5/2003 | Kipke |
| 2003/0109871 A1 | 6/2003 | Johnson |
| 2003/0130711 A1 | 7/2003 | Pearson et al. |
| 2003/0187430 A1 | 10/2003 | Vorisek |
| 2004/0006337 A1 | 1/2004 | Nasab et al. |
| 2004/0030258 A1 | 2/2004 | Williams et al. |
| 2004/0044292 A1 | 3/2004 | Yasushi et al. |
| 2004/0078036 A1 | 4/2004 | Keidar |
| 2004/0078058 A1 | 4/2004 | Holmstrom |
| 2004/0082946 A1 | 4/2004 | Malis |
| 2004/0087975 A1 | 5/2004 | Lucatero |
| 2004/0097806 A1 | 5/2004 | Hunter |
| 2004/0147920 A1 | 7/2004 | Keidar |
| 2004/0181165 A1 | 9/2004 | Hoey et al. |
| 2004/0243018 A1 | 12/2004 | Organ |
| 2004/0243181 A1 | 12/2004 | Conrad |
| 2004/0267252 A1 | 12/2004 | Washington |
| 2005/0010263 A1 | 1/2005 | Schauerte |
| 2005/0054944 A1 | 3/2005 | Nakada |
| 2005/0065507 A1 | 3/2005 | Hartley |
| 2005/0222554 A1 | 10/2005 | Wallace |
| 2006/0015033 A1 | 1/2006 | Blakley |
| 2006/0085049 A1 | 4/2006 | Cory et al. |
| 2006/0116669 A1 | 6/2006 | Dolleris |
| 2006/0173251 A1 | 8/2006 | Govari et al. |
| 2006/0200049 A1 | 9/2006 | Leo et al. |
| 2006/0235286 A1 | 10/2006 | Stone et al. |
| 2007/0016006 A1 | 1/2007 | Shachar |
| 2007/0055142 A1 | 3/2007 | Webler |
| 2007/0073179 A1 | 3/2007 | Afonso et al. |
| 2007/0083193 A1 | 4/2007 | Werneth et al. |
| 2007/0100332 A1 | 5/2007 | Paul et al. |
| 2007/0106289 A1 | 5/2007 | O'Sullivan |
| 2007/0118100 A1 | 5/2007 | Mahesh et al. |
| 2007/0123764 A1 | 5/2007 | Thao et al. |
| 2007/0161915 A1 | 7/2007 | Desai |
| 2007/0225558 A1 | 9/2007 | Hauck |
| 2007/0225593 A1 | 9/2007 | Porath |
| 2007/0244479 A1 | 10/2007 | Beatty et al. |
| 2007/0255162 A1 | 11/2007 | Abboud et al. |
| 2008/0091193 A1 | 4/2008 | Kauphusman |
| 2008/0097220 A1 | 4/2008 | Lieber |
| 2008/0097422 A1 | 4/2008 | Edwards |
| 2008/0132890 A1 | 6/2008 | Woloszko et al. |
| 2008/0183071 A1 | 7/2008 | Strommer |
| 2008/0183189 A1 | 7/2008 | Teichman et al. |
| 2008/0221440 A1 | 9/2008 | Iddan et al. |
| 2008/0234564 A1 | 9/2008 | Beatty et al. |
| 2008/0249536 A1 | 10/2008 | Stahler |
| 2008/0275465 A1 | 11/2008 | Paul et al. |
| 2008/0288023 A1 | 11/2008 | John |
| 2008/0288038 A1 | 11/2008 | Paul |
| 2008/0300589 A1 | 12/2008 | Paul |
| 2008/0312713 A1 | 12/2008 | Wilfley |
| 2009/0012533 A1 | 1/2009 | Barbagli |
| 2009/0036794 A1 | 2/2009 | Stubhaug |
| 2009/0163904 A1 | 6/2009 | Miller |
| 2009/0171235 A1 | 7/2009 | Schneider |
| 2009/0171345 A1 | 7/2009 | Miller |
| 2009/0177111 A1 | 7/2009 | Miller |
| 2009/0247942 A1 | 10/2009 | Kirschenman |
| 2009/0247943 A1 | 10/2009 | Kirschenman |
| 2009/0247944 A1 | 10/2009 | Kirschenman |
| 2009/0247993 A1 | 10/2009 | Kirschenman |
| 2009/0248042 A1 | 10/2009 | Kirschenman |
| 2009/0275827 A1 | 11/2009 | Aiken et al. |
| 2009/0276002 A1 | 11/2009 | Sommer |
| 2009/0306655 A1 | 12/2009 | Stangenes |
| 2010/0069921 A1 | 3/2010 | Miller et al. |
| 2010/0168550 A1 | 7/2010 | Byrd |
| 2010/0168735 A1 | 7/2010 | Deno |
| 2010/0191089 A1 | 7/2010 | Stebler et al. |
| 2010/0256558 A1 | 10/2010 | Olson et al. |
| 2010/0274239 A1 | 10/2010 | Paul |
| 2010/0298623 A1 | 11/2010 | Cao |
| 2011/0015569 A1 | 1/2011 | Kirschenman |
| 2011/0118727 A1 | 5/2011 | Fish |
| 2011/0313311 A1 | 12/2011 | Gaw |
| 2011/0313417 A1 | 12/2011 | de la Rama et al. |
| 2012/0158011 A1 | 6/2012 | Sandhu |

FOREIGN PATENT DOCUMENTS

| | | |
|---|---|---|
| JP | H08511440 | 12/1996 |
| JP | 2005279256 | 10/2005 |
| WO | 1998/046149 | 10/1998 |
| WO | 2000/078239 | 12/2000 |
| WO | 2007/067628 | 6/2007 |
| WO | 2007/067938 | 6/2007 |
| WO | 2007/067941 | 6/2007 |
| WO | 2009/065140 | 5/2009 |
| WO | 2009/085457 | 7/2009 |
| WO | 2009/120982 | 10/2009 |
| WO | 2011/123669 | 10/2011 |

OTHER PUBLICATIONS

Author: Masse, Stephane Title: A Three-dimensional display for cardiac activation mapping Citation: Pace, vol. 14 Publication Date: Apr. 1991.

Avitall, Boaz; "The Effects of Electrode-Tissue Contact on Radiofrequency Lesion Generation"; PACE, vol. 20; Reference pp. 2899-2910; Publication Date: Dec. 1997.

(56) References Cited

OTHER PUBLICATIONS

Chakraborty, D. P.; "ROC curves predicted by a model of visual search"; Institute of Physics Publishing, Phys. Med. Biol. 51; Reference pp. 3463-3482; Publication Date: Jul. 6, 2006.

Cho, Sungbo, "Design of electrode array for impedance measurement of lesions in arteries", Physiological Measurement, vol. 26 S19-S26, Apr. 2005.

Dumas, John H.; "Myocardial electrical impedance as a predictor of the quality of RF-induced linear lesions"; Physiological Measurement, vol. 29; Reference Pages: Abstract only; Publication Date: Sep. 17, 2008.

Fenici, R. R.; "Biomagnetically localizable multipurpose catheter and method for MCG guided intracardiac electrophysiology, biopsy and ablation of cardiac arrhythmias"; International Journal of Cardiac Imaging 7; Reference pp. 207-215; Publication Date: Sep. 1991.

Gao et al. "Computer-Assisted Quantitative Evaluation of Therapeutic Responses for Lymphoma Using Serial PET/CT Imaging", Academic Radiology, vol. 17, No. 4, Apr. 2010.

He, Ding Sheng; "Assessment of Myocardial Lesion Size during In Vitro Radio Frequency Catheter Ablation"; IEEE Transactions on Biomedical Engineering, vol. 50, No. 6; Reference pp. 768-776; Publication Date: Jun. 2003.

Himel, Herman D.; "Development of a metric to assess completeness of lesions produced by radiofrequency ablation in the heart"; Dept. of Biomedical Engineering, University of NC, Chapel Hill; Reference pp. i-xvii; 1-138; Publication Date: 2006.

Holmes, Douglas, Tissue Sensing Technology Enhances Lesion Formation During Irrigated Catheter Ablation, HRS, Reference Pages: Abstract only, Publication Date: May 2008.

Salazar, Y; "Transmural versus nontransmural in situ electrical impedance spectrum for healthy, ischemic, and healed myocardium", Transactions on Biomedical Engineering, vol. 51, No. 8, Aug. 2004.

Thomas, Stuart P., et al., Comparison of Epicardial and Endocardial Linear Ablation Using Handheld Probes, The Annals of Thoracic Surgery, vol. 75, Issue 2, pp. 543-548, Feb. 2003.

Zheng, Xiangsheng; "Electrode Impedance: An Indicator of Electrode-Tissue Contact and Lesion Dimensions During Linear Ablation": Journal of Interventional Cardiac Electrophysiology 4; Reference pp. 645-654; Publication Date: Dec. 2000.

| TIME (t) | RESISTANCE (R) | PHASE ANGLE ($\phi$) | AVG. POWER (AVG.P) |
|---|---|---|---|
| $t_0$ | $R_0$ | $\phi_0$ | -- |
| $t_1$ | $R_1$ | $\phi_1$ | $AVG.P_1$ |
| $t_2$ | $R_2$ | $\phi_2$ | $AVG.P_2$ |
| $t_3$ | $R_3$ | $\phi_3$ | $AVG.P_3$ |
| . | . | . | . |
| . | . | . | . |
| $t_n$ | $R_n$ | $\phi_n$ | $AVG.P_n$ |

FIG.7

| TIME (t) | RESISTANCE (R) | REACTANCE (X) | ECI | AVERAGE POWER (AVG.P) |
|---|---|---|---|---|
| $t_1$ | $R_1$ | $X_1$ | $ECI_1$ | $AVG.P_1$ |
| $t_2$ | $R_2$ | $X_2$ | $ECI_2$ | $AVG.P_2$ |
| $t_3$ | $R_3$ | $X_3$ | $ECI_3$ | $AVG.P_3$ |
| ... | ... | ... | ... | ... |
| $t_n$ | $R_n$ | $X_n$ | $ECI_n$ | $AVG.P_n$ |

FIG. 11

| TIME (t) | RESISTANCE (R) | REACTANCE (X) | IMPEDANCE (Z) | TEMPERATURE (T) | POWER (P) |
|---|---|---|---|---|---|
| $t_1$ | $R_1$ | $X_1$ | $Z_1$ | $T_1$ | $P_1$ |
| $t_2$ | $R_2$ | $X_2$ | $Z_2$ | $T_2$ | $P_2$ |
| $t_3$ | $R_3$ | $X_3$ | $Z_3$ | $T_3$ | $P_3$ |
| ... | ... | ... | ... | ... | ... |
| $t_n$ | $R_n$ | $X_n$ | $Z_n$ | $T_n$ | $P_n$ |

FIG. 15

ND/OR THE LIKELIHOOD OF STEAM POP DURING AN ABLATION
GRAPHICAL USER INTERFACE FOR REAL-TIME RF LESION DEPTH DISPLAY

CROSS-REFERENCE TO RELATED APPLICATIONS

This application is a continuation of U.S. application Ser. No. 12/963,257, filed 8 Dec. 2010 (the '257 application), now U.S. Pat. No. 9,492,226, which is a continuation-in-part of U.S. application Ser. No. 12/946,941, filed 16 Nov. 2010 (the 941 application), now U.S. Pat. No. 8,603,084, which is a continuation-in-part of U.S. application Ser. No. 12/622,488, filed 20 Nov. 2009 (the '488 application), now U.S. Pat. No. 8,403,925, which claims the benefit of U.S. application No. 61/177,876, filed 13 May 2009 (the '876 application) and is a continuation-in-part of U.S. application Ser. No. 12/253,637, filed 17 Oct. 2008 (the '637 application), now U.S. Pat. No. 8,449,535, which is a continuation-in-part of U.S. application Ser. No. 12/095,688, filed 30 May 2008 (the '688 application), now U.S. Pat. No. 9,271,782, which is a national stage application of International application no. PCT/US2006/061714, filed 6 Dec. 2006 (the '714 application), which claims the benefit of U.S. application No. 60/748,234, filed 6 Dec. 2005 (the '234 application). The '257 application, in turn, is a continuation-in-part of U.S. application Ser. No. 12/353,897, filed 14 Jan. 2009 (the '897 application), now abandoned, which claims the benefit of U.S. application No. 61/020,806, filed 14 Jan. 2008 (the '806 application) and is also a continuation-in-part of U.S. application Ser. No. 12/253,637, filed 17 Oct. 2008 (the '637 application), now U.S. Pat. No. 8,449,535, which is a continuation-in-part of U.S. application Ser. No. 12/095,688, filed 30 May 2008 (the '688 application), now U.S. Pat. No. 9,271,782, which is a national stage application of International application no. PCT/US2006/061714, filed 6 Dec. 2006 (the '714 application), which claims the benefit of U.S. application No. 60/748,234, filed 6 Dec. 2005 (the '234 application). The '257 application also claims the benefit of U.S. application No. 61/285,756, filed 11 Dec. 2009 (the '756 application). The '257 application, '941 application, '488 application, '876 application, '637 application, '688 application, '714 application, '234 application, '897 application, '806 application and '756 application are each hereby incorporated by reference as though fully set forth herein.

BACKGROUND OF THE INVENTION a. Field of the Invention

This disclosure relates to a system and method for assessing the formation of a lesion in target tissue and displaying a visual representation indicative of the characteristics of a lesion formed in the target tissue. More particularly, this disclosure relates to a system and method for assessing the depth of a lesion formed in the target tissue and displaying a visual representation indicative of the depth of the lesion formed in the target tissue. The system and method may also display a visual representation indicative of the thickness of the target tissue and provide a visual representation indicative of the depth of the lesion formed in the target tissue relative to the thickness of the target tissue (i.e., provide information regarding the transmurality of the lesion). The system and method may also display a visual representation indicative of the likelihood a lesion has reached a predetermined depth, the temperature of the target tissue during an ablation procedure being performed on the target tissue, and/or the likelihood of steam pop during an ablation procedure being performed on the target tissue.

b. Background Art

It is known that ablation therapy may be used to treat various conditions afflicting the human anatomy. One such condition that ablation therapy finds particular applicability is in the treatment of atrial arrhythmias, for example. When tissue is ablated, or at least subjected to ablative energy generated by an ablation generator and delivered by an ablation catheter, lesions form in the tissue. More particularly, electrode mounted on or in the ablation catheter are used to create tissue necrosis in cardiac tissue to correct conditions such as atrial arrhythmia (including, but not limited to, ectopic atrial tachycardia, atrial fibrillation, and atrial flutter). Atrial arrhythmias can create a variety of dangerous conditions including irregular heart rates, loss of synchronous atrioventricular contractions and stasis of blood flow which can lead to a variety of ailments and even death. It is believed that the primary cause of atrial arrhythmia is stray electrical signals within the left or right atrium of the heart. The ablation catheter imparts ablative energy (e.g., radio frequency energy, cryoablation, lasers, chemicals, high-intensity focused ultrasound, etc.) to cardiac tissue to create a lesion in the cardiac tissue. The lesion disrupts undesirable electrical pathways and thereby limits or prevents stray electrical signals that lead to arrhythmias.

One challenge with ablation procedures is in the assessment of the lesion formation as a result of the application of ablative energy to the tissue. For example, it is difficult to evaluate, assess, and/or determine the depth of a lesion in the tissue. As such, it is difficult to determine whether the tissue has been sufficiently or acceptably ablated, or at least whether a lesion has reached a desired depth. Lesion formation has typically been fairly crudely assessed.

For example, conventional techniques to assess lesion formation, and particularly, lesion depth, have included monitoring the impedance on the ablation generator and monitoring electrogram reduction as the ablation procedure is performed and progresses. However, conventional techniques have proved to be less than optimal as none of the conventional techniques provide an accurate means by which the depth of a lesion, for example, can be predicted with any real certainty. Accordingly, it is also difficult to determine whether a lesion is transmural (i.e., that the lesion extends through the entire thickness of the target tissue) and may be useful in connection with blocking arrythmias and/or atrial fibrillation.

By providing information to the clinician regarding lesion formation in target tissue as a result of an ablation procedure being performed thereon, lesion creation may be completed in a safer, more efficacious manner with a greater chance of transmural lesions and a lesser chance of collateral damage when performing an ablation procedure on thin target tissue.

Accordingly, the inventors herein have recognized a need for a system and method for assessing lesion formation in target tissue as a result of an ablation procedure being performed thereon and displaying information regarding lesion formation in target tissue that will minimize and/or eliminate one or more of the deficiencies in conventional ablation systems.

BRIEF SUMMARY OF THE INVENTION

The present invention is directed to a method and system for displaying characteristics of target tissue during an ablation procedure. The system according to the present teachings includes an electronic control unit (ECU). The ECU is configured to receive as an input data regarding the electrical properties of the target tissue for a time period. The data regarding the electrical properties of the target tissue may be generated by measuring electrical properties of the target tissue with a sensor on an ablation catheter.

The ECU is further configured to determine a value responsive to the data and indicative of at least one of a predicted depth of a lesion in the target tissue, a predicted temperature of the target tissue, and a likelihood of steam pop of the target tissue for the time period. The ECU is further configured to output the value. The system according to the present teachings further includes a display device operatively connected to the ECU. The display device is configured to receive the value and display a visual representation indicative of at least one of a predicted depth of a lesion in the target tissue, a predicted temperature of the target tissue, and a predicted likelihood of steam pop of the target tissue for the time period. In an exemplary embodiment, the visual representation is displayed during the time period. In one embodiment, the ECU is configured to store the value, to retrieve the stored value subsequent to the time period, and to output the stored value to the display device subsequent to the time period. In this embodiment, the display device is configured to display a visual representation corresponding to the stored value and indicative of at least one of a predicted depth of a lesion in the target tissue, a predicted temperature of the target tissue, and a likelihood of steam pop of the target tissue subsequent to the time period.

In an exemplary embodiment, the ECU is further configured to receive as an input data regarding the thickness of the target tissue. The display device may be further configured to display a visual representation indicative of the thickness of the target tissue. The display device may also be further configured to display a visual representation indicative of the transmurality of a lesion in the target tissue.

The format of the visual representation indicative of at least one of a predicted depth of a lesion in the target tissue, a predicted temperature of the target tissue, and a predicted likelihood of steam pop of the target tissue for the time period may vary and may comprise any number of representations in accordance with various embodiments of the invention. For example, the representation may comprise an expandable graph or meter, a gauge including a scale and an indicator moveable along the scale, and/or a color in accordance with an exemplary embodiment of the invention. For example, the expandable graph or meter may be at least partially overlaid over the visual representation indicative of the thickness of the target tissue. For another example, the system may be configured to store a first color associated with a first range of values indicative of at least one of a predicted depth of a lesion in the target tissue, a predicted temperature of the target tissue, and a predicted likelihood of steam pop of the target tissue for the time period. The system may further be configured to store a second color associated with a second range of values indicative of at least one of a predicted depth of a lesion in the target tissue, a predicted temperature of the target tissue, and a predicted likelihood of steam pop of the target tissue for the time period. The system may further be configured to store a third color associated with a third range of values indicative of at least one of a predicted depth of a lesion in the target tissue, a predicted temperature of the target tissue, and a predicted likelihood of steam pop of the target tissue for the time period. The system may then be configured to display a color associated with the value indicative of at least one of a predicted depth of a lesion in the target tissue, a predicted temperature of the target tissue, and a predicted likelihood of steam pop of the target tissue for the time period.

The display device may be further configured to display a slider bar configured to adjust a threshold against which the value indicative of at least one of a predicted depth of a lesion in the target tissue, a predicted temperature of the target tissue, and a likelihood of steam pop of the target tissue may be compared, thereby adjusting a sensitivity of the graphical user interface system.

The display device may further be configured to display a visual representation indicative of an ablation catheter used to perform the ablation procedure in accordance with an exemplary embodiment. This may include a first view along a first axis of a body upon which the ablation procedure is performed and a second view along a second axis of the body upon which the ablation procedure is performed.

In accordance with another aspect of the invention, the system for displaying characteristics of target tissue during an ablation procedure includes an ablation catheter including a sensor configured for obtaining data regarding the electrical properties of the target tissue for a time period; an electroanatomic visualization, mapping, and navigation system configured for generating an anatomical model of at least the target tissue, the electroanatomic visualization, mapping, and navigation system including a display device for displaying the anatomical model; and a graphical user interface system as described hereinabove. The visual representation indicative of one of a predicted depth of a lesion in the target tissue, a predicted temperature of the target tissue, and a predicted likelihood of steam pop of the target tissue for the time period may appear as an inset on the display device of the electromagnetic visualization, mapping, and navigation system in accordance with an embodiment of the invention. The display device may be further configured to receive the value and display a visual representation indicative of a location of the ablation catheter used to perform the ablation procedure relative to the anatomical model generated by the electroanatomic visualization, mapping, and navigation system.

In accordance with an exemplary embodiment, at least one of the display device and the ablation catheter may be configured to present at least one of an audible indication, a tactile indication, and a vibrational indication if the value indicative of one of a predicted depth of a lesion in the target tissue, a predicted temperature of the target tissue, and a predicted likelihood of steam pop of the target tissue for the time period exceeds a predetermined threshold.

In accordance with another aspect of the invention, a method for displaying characteristics of target tissue during an ablation procedure is provided. In accordance with the present teachings, the method includes the steps of obtaining data regarding the thickness of the target tissue; displaying a visual representation indicative of the thickness of the target tissue; obtaining data regarding the electrical properties of the target tissue for a time period; determining a value responsive to the data regarding the electrical properties of the target tissue that is indicative of one of a predicted depth of a lesion in the target tissue, a predicted temperature of the target tissue, and a predicted likelihood of steam pop of the target tissue for the time period; and displaying a visual representation indicative of one of a predicted depth of a lesion in the target tissue, a predicted temperature of the target tissue, and a predicted likelihood of steam pop of the target tissue for the time period.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 7 is a table showing an exemplary embodiment of how data acquired by the system of FIG. 1 is organized and/or stored.

FIG. 11 is a table showing another exemplary embodiment of how data acquired by the system of FIG. 1 is organized and/or stored.

FIG. 15 is a table showing another exemplary embodiment of how data acquired by the system of FIG. 1 is organized and/or stored.

DETAILED DESCRIPTION OF THE INVENTION

Figure 1:
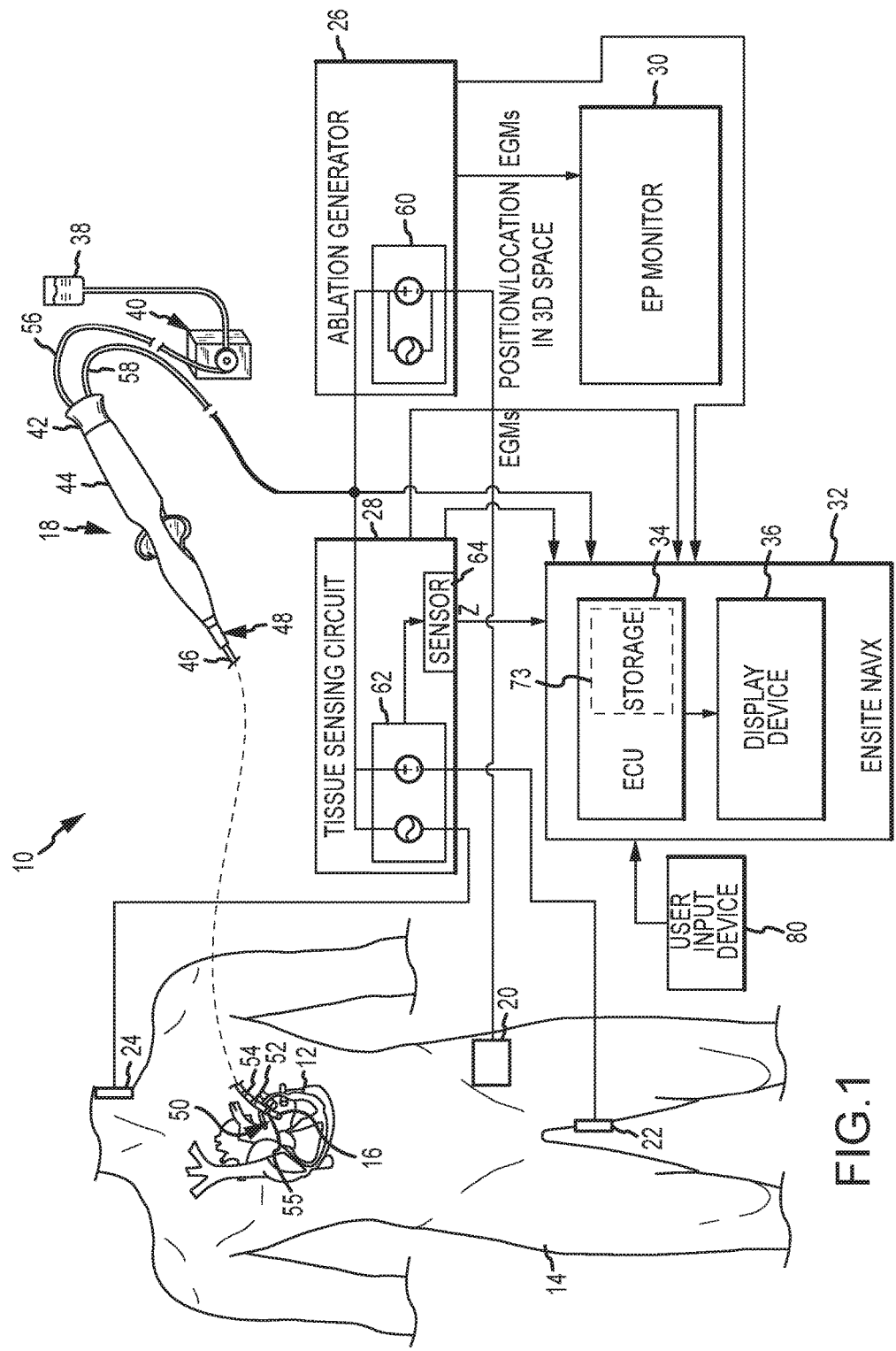
FIG. 1 is a diagrammatic view of a system in accordance with the present teachings.

Referring now to the drawings wherein like reference numerals are used to identify identical components in the various views, FIG. 1 illustrates one exemplary embodiment of a system 10 configured, at least in part, for assessing the formation of a lesion in a tissue 12 of a body 14 as a result of an ablation procedure being performed on the tissue 12.

In an exemplary embodiment wherein the tissue 12 is cardiac tissue, the system 10 is configured to assess the formation of a lesion in the tissue 12 being ablated by radio frequency (RF) energy or power delivered from an electrode 16 disposed on a catheter 18. For the sake of clarity and brevity alone, the description set forth below will be with respect to cardiac tissue only. It should be understood, however, that the present disclosure may find application in connection with assessing lesion depth in other types of tissue during ablation procedures. Accordingly, the present disclosure is not meant to be limited solely to cardiac tissue.

In addition to the electrode 16 and the catheter 18, the system 10 may include patch electrodes 20, 22, 24, an ablation generator 26, a tissue sensing circuit 28, an electrophysiology (EP) monitor 30, and a system 32 for visualization, mapping, and navigation of internal body structures, which may include an electronic control unit 34 and a display device 36, among other components.

The catheter 18 is provided for examination, diagnosis and treatment of internal body tissues such as the tissue 12. In accordance with one embodiment, the catheter 18 comprises an ablation catheter and, more particularly, an irrigated radio-frequency (RF) ablation catheter. In an exemplary embodiment, the catheter 18 is connected to a fluid source 38 having a biocompatible fluid, such as saline through a pump 40 (which may comprise, for example, a fixed rate roller pump or variable volume syringe pump with a gravity feed supply from the fluid source 38 as shown), for irrigation. It should be noted, however, that the present disclosure is not meant to be limited to irrigated catheters, but rather it may find applicability with any number of electrode and ablation device combinations. In an exemplary embodiment, the catheter 18 is also electrically connected to the ablation generator 26 for delivery of RF energy or power. The catheter 18 may include a cable connector or interface 42, a handle 44, a shaft 46 having a proximal end 48 and a distal 50 end (as used herein, "proximal" refers to a direction toward the end of the catheter near the clinician, and "distal" refers to a direction away from the clinician and (generally) inside the body of a patient) and one or more electrodes 16, 52, 54, 55. The catheter 18 may also include other conventional components, such as, for example, a temperature sensor (e.g., a thermocouple or temperature-sensing electrode, for example) for sensing the temperature of the tip of the catheter 18, other additional electrodes and corresponding conductors or leads not illustrated herein, or additional ablation elements (e.g., a high intensity focused ultrasound ablation element).

The connector 42 provides mechanical, fluid and electrical connection(s) for cables 56, 58 extending, for example, from the pump 40 and the ablation generator 26. The connector 42 is conventional in the art and is disposed at the proximal end 48 of the catheter 18.

The handle 44 provides a location for the clinician to hold the catheter 18 and may further provide a means for steering or the guiding of the shaft 46 within the body 14. For example, the handle 44 may include means to change the length of a guidewire extending through the catheter 18 to the distal end 50 of the shaft 46 to steer the shaft 46. The handle 44 is also conventional in the art and it will be understood that the construction of the handle 44 may vary. In an alternate exemplary embodiment to be described in greater detail below, the catheter 18 may be robotically or magnetically driven or controlled. Accordingly, rather than a clinician manipulating a handle to steer or guide the catheter 18, and the shaft 46 thereof, in particular, a robot or a magnetic-based system is used to manipulate the catheter 18.

The shaft 46 is an elongated, tubular, flexible member configured for movement within the body 14. The shaft 46 supports the electrodes 16, 52, 54, 55, associated conductors, and possibly additional electronics used, for example, for signal processing or conditioning. The shaft 46 may also permit transport, delivery and/or removal of fluids (including irrigation fluids, cryogenic ablation fluids, and bodily fluids), medicines, and/or surgical tools or instruments. The shaft 46 may be made from conventional materials such as polyurethane and defines one or more lumens configured to house and/or transport electrical conductors, fluids or surgical tools. The shaft 46 may be introduced directly into a blood vessel or other structure within the body 14, or may be introduced through a conventional introducer. The shaft 46 may then be steered or guided through the body 14 to a desired location such as the tissue 12 with guidewires or other means known in the art.

The electrodes 16, 52, 54, 55 are provided for a variety of diagnostic and therapeutic purposes including, for example, electrophysiological studies, catheter identification and location, pacing, cardiac mapping, temperature sensing, and ablation. In the illustrated embodiment, the catheter 18 includes an ablation tip electrode 16 at the distal end 50 of the shaft 46, a plurality of ring electrodes 52, 54, 55. The catheter 18 may include a temperature sensor. In some embodiments, one of the electrodes 52, 54, 55 may comprise a temperature-sensing electrode. In other embodiments, the catheter 18 may include an additional temperature sensor. It should be understood, however, that the number, shape, orientation, and purpose of the electrodes 16, 52, 54, 55 may vary. Accordingly, the illustrated embodiment is provided for exemplary purposes only.

The patch electrodes 20, 22, 24 provide RF or navigational signal injection paths and/or are used to sense electrical potentials. The electrodes 20, 22, 24 may also have additional purposes, such as, for example, facilitating the generation of an electromechanical map by the electrodes 16, 52, 54, 55. The electrodes 20, 22, 24 are made from flexible, electrically conductive material and are configured for affixation to the body 14 such that the electrodes 20, 22, 24 are in electrical contact with the patient's skin. The electrode 20 may function as an RF indifferent/dispersive return for the RF ablation signal. The electrodes 22, 24 may function as returns for the RF ablation signal source and/or an excitation signal generated by the tissue sensing circuit 28 as described in greater detail hereinbelow. In accordance with one aspect of the present disclosure discussed hereinbelow, the electrodes 22, 24 are preferably spaced relatively far apart. In the illustrated embodiment, the electrodes 22, 24, are located on the medial aspect of the left leg and the dorsal aspect of the neck. The electrodes 22, 24, may alternatively be located on the front and back of the torso or in other conventional orientations.

The ablation generator 26 generates, delivers, and controls RF energy output by the ablation catheter 18, and the electrode 16, in particular. The generator 26 is conventional in the art and may comprise the commercially available unit sold under the model number IBI-1500T-11 RF Cardiac Ablation Generator, available from Irvine Biomedical, Inc. The generator 26 includes an RF ablation signal source 60 configured to generate an ablation signal that is output across a pair of source connectors: a positive polarity connector SOURCE (+) which may connect to the tip electrode 16; and a negative polarity connector SOURCE(−) which may be electrically connected by conductors or lead wires to one of the patch electrodes 20, 22, 24 (see FIG. 2). It should be understood that the term connectors as used herein does not imply a particular type of physical interface mechanism, but is rather broadly contemplated to represent one or more electrical nodes. The source 60 is configured to generate a signal at a predetermined frequency in accordance with one or more user specified parameters (e.g., power, time, etc.) and under the control of various feedback sensing and control circuitry as is know in the art. The source 60 may generate a signal, for example, with a frequency of about 200 kHz or greater. The generator 26 may also monitor various parameters associated with the ablation procedure including impedance, the temperature at the tip of the catheter, ablation energy, and the position of the catheter and provide feedback to the clinician regarding these parameters. The impedance measurement output by a typical currently available generator reflects the magnitude of impedance not only at the tissue 12, but the entire impedance between the tip electrode 16 and the corresponding patch electrode 20 on the body surface. In an exemplary embodiment, the ablation generator 26 may generate a higher frequency current for the purposes of RF ablation, and a second lower frequency current for the purpose of measuring impedance.

The tissue sensing circuit 28 provides a means, such as a tissue sensing signal source 62, for generating an excitation signal used in impedance measurements and means, such as a complex impedance sensor 64, for resolving the detected impedance into its component parts. In another exemplary embodiment, the complex impedance may be measured using components other than the tissue sensing circuit 28, such as, for example, the ablation generator 26. However, in an embodiment wherein the tissue sensing circuit 28 is used, the signal source 62 is configured to generate an excitation signal across source connectors SOURCE (+) and SOURCE (−) (See FIG. 2). The source 62 may output a signal having a frequency within a range from about 1 kHz to over 500 kHz. In an exemplary embodiment, the frequency is about 20 kHz. In one exemplary embodiment, the excitation signal is a constant current signal that, in an exemplary embodiment, is in the range of between 20-200 µA. In another exemplary embodiment, the current is about 100 µA. As discussed below, the constant current AC excitation signal generated by the source 62 is configured to develop a corresponding AC response voltage signal that is dependent on the complex impedance of the tissue 12 and is sensed by the complex impedance sensor 64. The sensor 64 resolves the complex impedance into its component parts (i.e., the resistance (R) and reactance (X), or the impedance magnitude (|Z|) and phase angle (∠Z or ϕ)). Sensor 64 may include conventional filters (e.g., bandpass filters) to block frequencies that are not of interest, but permit appropriate frequencies, such as the excitation frequency, to pass, as well as conventional signal processing software used to obtain the component parts of the measured complex impedance.

It should be understood that variations are contemplated by the present disclosure. For example, the excitation signal may be an AC voltage signal where the response signal comprises an AC current signal. Nonetheless, in an exemplary embodiment, a constant current excitation signal is employed. It should be appreciated that in an exemplary embodiment the excitation signal frequency is outside of the frequency range of the RF ablation signal, which allows the complex impedance sensor 64 to more readily distinguish the two signals, and facilitates filtering and subsequent processing of the AC response voltage signal. In an exemplary embodiment, the excitation signal frequency is also outside the frequency range of conventionally expected electrogram (EGM) signals in the frequency range of 0.05 Hz-1 kHz. Thus, in summary, in an exemplary embodiment the excitation signal has a frequency that is above the typical EGM signal frequencies and below the typical RF ablation signal frequencies. Additionally, in certain embodiments multiple excitation signals of different frequencies may be used to determine multiple complex impedances. For example, in one exemplary embodiment, a 20 kHz signal and a 200 kHz signal may be generated and a complex impedance corresponding to each may be determined and used as will be described below. Accordingly, the present invention is not limited to an embodiment wherein a single excitation signal is employed, but rather includes embodiments wherein multiple excitation signals are used. For the sake of clarity and brevity, however, the following description will be limited to the embodiment wherein a single excitation signal is use.

The circuit 28 is also connected, for a purpose described hereinbelow, across a pair of sense connectors: a positive polarity connector SENSE (+) which may connect to the tip electrode 16; and a negative polarity connector SENSE (−) which may be electrically connected to one of the patch electrodes 20, 22, 24 (see FIG. 2; note, however, that the connector SENSE (−) should be connected to a different electrode of the electrodes 20, 22, 24 relative to the connector SOURCE (−) as discussed below). It should again be understood that the term connectors as used herein does not imply a particular type of physical interface mechanism, but is rather broadly contemplated to represent one or more electrical nodes.

Figure 2:
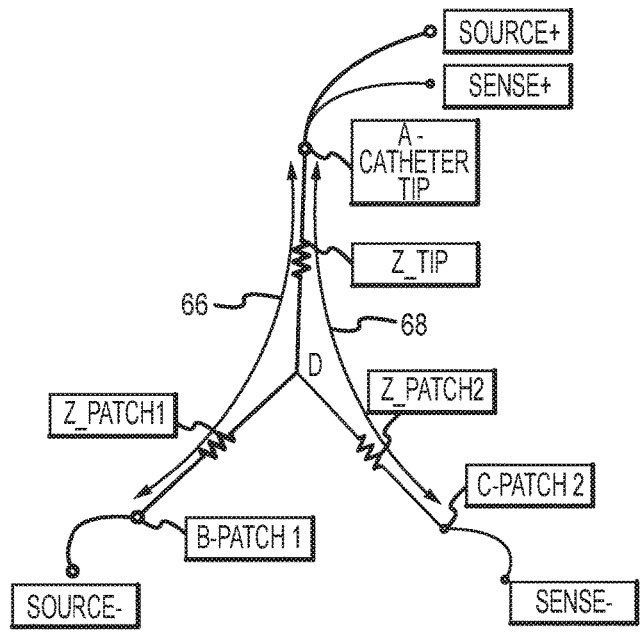
FIG. 2 is a simplified schematic diagram illustrating how impedance is determined in accordance with the present teachings.

Referring now to FIG. 2, connectors SOURCE (+), SOURCE (−), SENSE (+) and SENSE (−) form a three terminal arrangement permitting measurement of the complex impedance at the interface of the tip electrode 16 and the tissue 12. Complex impedance can be expressed in rectangular coordinates as set forth in equation (1):

$$Z=R+jX \quad (1)$$

where R is the resistance component (expressed in ohms); and X is a reactance component (also expressed in ohms). Complex impedance can also be expressed polar coordinates as set forth in equation (2):

$$Z=r \cdot e^{j\theta}=|Z|\angle\theta \quad (2)$$

where |Z| is the magnitude of the impedance (expressed in ohms) and ∠Z=θ is the phase angle expressed in radians. Alternatively, the phase angle may be expressed in terms of degrees where $$\phi = \left(\frac{180}{\pi}\right)\theta.$$

Throughout the remainder of this specification, phase angle will be preferably referenced in terms of degrees. The three terminals comprise: (1) a first terminal designated "A-Catheter Tip" which is the tip electrode 16; (2) a second terminal designated "B-Patch 1" such as the source return patch electrode 24; and (3) a third terminal designated "C-Patch 2" such as the sense return patch electrode 22. In addition to the ablation (power) signal generated by the source 60 of the ablation generator 26, the excitation signal generated by the source 62 in the tissue sensing circuit 28 is also be applied across the source connectors (SOURCE (+), SOURCE(−)) for the purpose of inducing a response signal with respect to the load that can be measured and which depends on the complex impedance.

As described above, in one embodiment, a 20 kHz, 100 µA AC constant current signal is sourced along a path 66, as illustrated, from one connector (SOURCE (+), starting at node A) through the common node (node D) to a return patch electrode (SOURCE (−), node B). The complex impedance sensor 64 is coupled to the sense connectors (SENSE (+), SENSE (−)), and is configured to determine the impedance across a path 68. For the constant current excitation signal of a linear circuit, the impedance will be proportional to the observed voltage developed across SENSE (+)/SENSE(−), in accordance with Ohm's Law: Z=V/I. Because voltage sensing is nearly ideal, the current flows through the path 66 only, so the current through the path 68 (node D to node C) due to the excitation signal is effectively zero. Accordingly, when measuring the voltage along the path 68, the only voltage observed will be where the two paths intersect (i.e., from node A to node D). Depending on the degree of separation of the two patch electrodes (i.e., those forming nodes B and C), an increasing focus will be placed on the tissue volume nearest the tip electrode 16. If the patch electrodes are physically close to each other, the circuit pathways between the catheter tip electrode 16 and the patch electrodes will overlap significantly and impedance measured at the common node (i.e., node D) will reflect impedances not only at the interface of the catheter electrode 16 and the tissue 12, but also other impedances between the tissue 12 and the surface of body 14. As the patch electrodes are moved further apart, the amount of overlap in the circuit paths decreases and impedance measured at the common node is only at or near the tip electrode 16 of the catheter 18.

Figure 3:
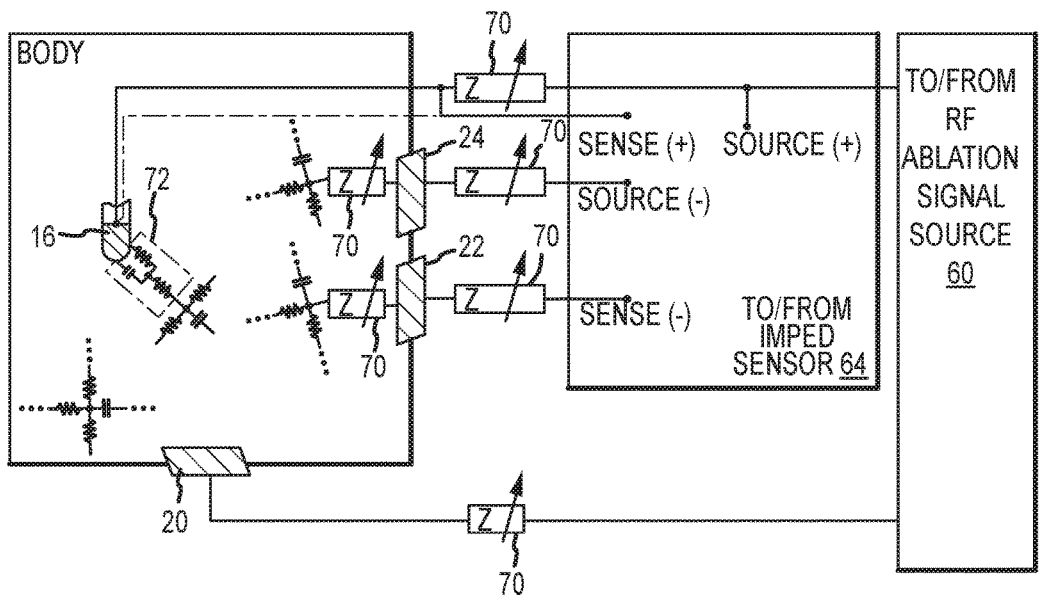
FIG. 3 is a diagrammatic and block diagram illustrating the approach in FIG. 2 in greater detail.

Referring now to FIG. 3, the concept illustrated in FIG. 2 is extended. FIG. 3 is a simplified schematic and block diagram of the three-terminal measurement arrangement of the invention. For clarity, it should be pointed out that the SOURCE (+) and SENSE (+) lines may be joined in the catheter connector or the handle (as in solid line) or may remain separate all the way to the tip electrode 16 (the SENSE (+) line being shown in phantom line from the handle to the tip electrode 16). FIG. 3 shows, in particular, several sources of complex impedance variations, shown generally as blocks 70, that are considered "noise" because such variations do not reflect the physiologic changes in the tissue whose complex impedance is being measured. For reference, the tissue 12 whose complex impedance is being measured is that near and around the tip electrode 16 and is enclosed generally by a phantom-line box 72 (and the tissue 12 is shown schematically, in simplified form, as a resistor/capacitor combination). One object of the present disclosure is to provide a measurement arrangement that is robust or immune to variations that are not due to changes in or around the box 72. For example, the variable complex impedance boxes 70 that are shown in series with the various cable connections (e.g., in the SOURCE (+) connection, in the SOURCE (−) and SENSE (−) connections, etc.) may involve resistive/inductive variations due to cable length changes, cable coiling and the like. The variable complex impedance boxes 70 that are near the patch electrodes 22, 24, may be more resistive/capacitive in nature, and may be due to body perspiration and the like over the course of a study. As will be seen, the various arrangements of the system 10 are relatively immune to the variations in the blocks 70, exhibiting a high signal-to-noise (S/N) ratio as to the complex impedance measurement for the block 72.

Although the SOURCE (−) and SENSE (−) returns are illustrated in FIG. 3 as patch electrodes 22, 24, it should be understood that other configurations are possible. In particular, the indifferent/dispersive return electrode 20 can be used as a return, as well as another electrode 52, 54 on the catheter 18, such as the ring electrode 52 as described in commonly assigned U.S. patent application Ser. No. 11/966,232 filed on Dec. 28, 2007 and titled "System and Method for Measurement of an Impedance using a Cather such as an Ablation Catheter," the entire disclosure of which is incorporated herein by reference.

The EP monitor 30 is provided to display electrophysiology data including, for example, an electrogram. The monitor 30 is conventional in the art and may comprise an LCD or CRT monitor or another conventional monitor. The monitor 30 may receive inputs from the ablation generator 26 as well as other conventional EP lab components not shown in the illustrated embodiment.

The system 32 is provided for visualization, mapping, and navigation of internal body structures. The system 32 may comprise the system having the model name EnSite NavX™ and commercially available from St. Jude Medical, Inc., and as generally shown with reference to commonly assigned U.S. Pat. No. 7,263,397 entitled "Method and Apparatus for Catheter Navigation and Location and Mapping in the Heart," the entire disclosure of which is incorporated herein by reference. Alternative systems may include, for example and without limitation, the Carto™ System available from Biosense Webster, and as generally shown with reference to U.S. Pat. No. 6,498,944 entitled "Intrabody Measurement" and U.S. Pat. No. 6,788,967 entitled "Medical Diagnosis, Treatment and Imaging Systems," both of which are incorporated herein by reference in their entireties; commonly available fluoroscopy systems; or a magnetic location system, such as, for example, the gMPS system from MediGuide Ltd., and as generally shown with reference to U.S. Pat. No. 7,386,339 entitled "Medical Imaging and Navigation System," the disclosure of which is incorporated herein by reference in its entirety. The system 32 may include the electronic control unit (ECU) 34 and the display device 36 among other components. In another exemplary embodiment, the ECU 34 and/or the display device 36 are separate and distinct components that are electrically connected to, and configured for communication with, the system 32.

Figure 4:
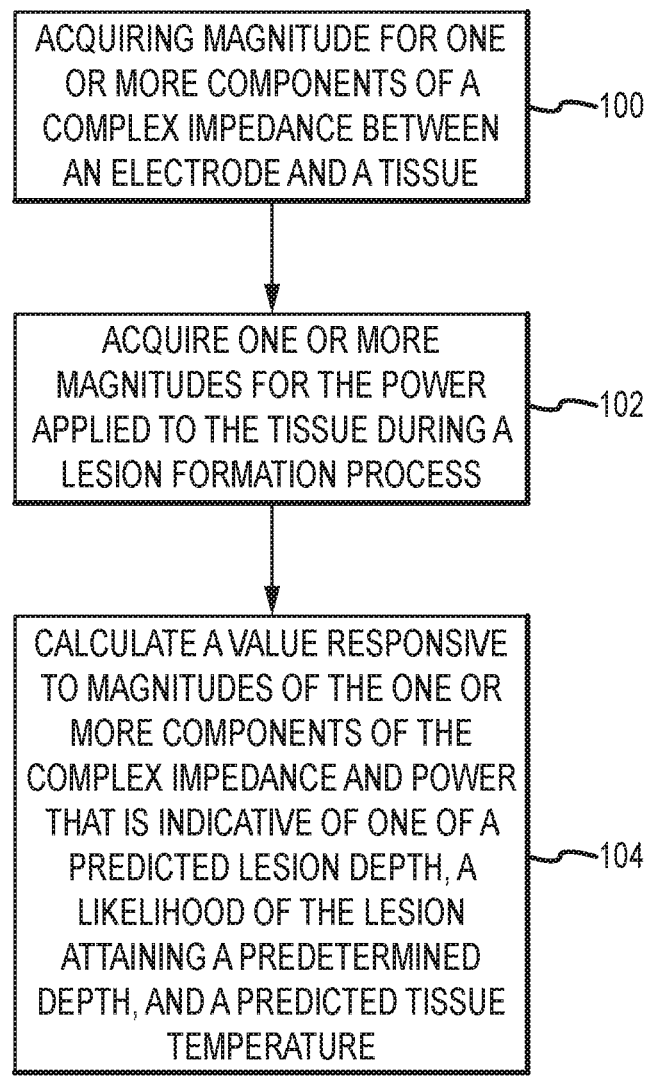
FIG. 4 is flow chart illustrative of an exemplary embodiment of a method for assessing the formation of a lesion in tissue during an ablation procedure performed on the tissue in accordance with the present teachings.

With reference to FIG. 4, the ECU 34 is configured to acquire a magnitude for one or more components of a complex impedance between the electrode 16 and the tissue 12 (i.e., the resistance (R) and reactance (X), or the impedance magnitude (|Z|) and phase angle (φ), or any combination of the foregoing or derivatives or functional equivalents thereof) (Step 100 in FIG. 4), as well as one or more magnitudes for the power or energy applied to the tissue 12 by the ablation generator 26 during the formation of a lesion in the tissue 12 (Step 102 in FIG. 4). The ECU 34 is further configured to calculate a value responsive to the magnitude(s) of the one or more components of the complex impedance and the magnitude of the applied power (Step 104 in FIG. 4), with the value being indicative of one of a predicted depth of the lesion formed in the tissue 12, a likelihood of the lesion in the tissue 12 reaching a predetermined depth, and a predicted temperature of the tissue 12. As will be described in greater detail below, in an embodiment wherein the value is indicative of the temperature of the tissue, the temperature is the temperature of the tissue a predetermined depth below the endocardial surface of the tissue 12. In one embodiment provided for exemplary purposes only, this predetermined depth is three millimeters (3 mm) below the endocardial surface.

In an embodiment of the system 10 such as that briefly described above wherein multiple excitation signals are utilized to determine multiple complex impedances, the ECU 34 may be configured to acquire one or more components of one or both of the complex impedances for calculating the value. For the sake of clarity and brevity, the following description will be limited to the calculation of the value using a single complex impedance. It should be understood, however, that the present disclosure is not meant to be limited to such an embodiment, but rather includes embodiments wherein components of multiple complex impedances are used in the calculation of the value.

In an exemplary embodiment, the ECU 34 comprises a programmable microprocessor or microcontroller, but may alternatively comprise an application specific integrated circuit (ASIC). The ECU 34 may include a central processing unit (CPU) and an input/output (I/O) interface through which the ECU 34 may receive a plurality of input signals including, for example and without limitation, signals from the complex impedance sensor 64 of the tissue sensing circuit 28 (for the magnitude(s) of the complex impedance component(s)), the ablation generator 26 or another recording system in communication with the ablation generator 26 (for the power level and/or the magnitude of the average power), and the temperature-sensing electrode or temperature sensor disposed at or near the distal end 50 of the catheter 18 either directly or through the ablation generator 26. The ECU 34 may further generate a plurality of output signals including those used to control the display device 36.

In accordance with one aspect of the present disclosure, the ECU 34 may be programmed with a computer program (i.e., software) encoded on a computer-readable storage medium for assessing the formation of a lesion in the tissue 12. More particularly, the computer program may be configured to assess the depth of a lesion being formed in the tissue 12 (e.g., predicting the depth of the lesion or determining the likelihood the lesion has reached a predetermined depth) and/or the temperature of the tissue 12 as a result of an ablation procedure being performed thereon. As illustrated in FIG. 4, and generally speaking, the program includes code for calculating a value responsive to magnitudes of one or more components of the complex impedance between the electrode 16 and the tissue 12, and the magnitude of the power or energy applied to the tissue 12 through the electrode 16, with the value being indicative of one of, for example, a predicted depth of a lesion formed in the tissue, a likelihood that the lesion has reached a predetermined depth, and a temperature of the tissue 12 in which the lesion is being formed. The program further includes code for performing or carrying out some or all of the functionality of the ECU 34 described in greater detail below.

Experimentation and analysis were performed to determine one or more equations based, at least in part, on complex impedance that could be used by the ECU 34 to assess the formation of a lesion being formed in the tissue 12 during an ablation procedure being performed thereon (i.e., an equation used to calculate a value that is indicative of a predicted depth of a lesion being formed in the tissue 12, a likelihood of the lesion having reached a predetermined depth, or a predicted temperature of the tissue 12 a predetermined depth below the surface of the tissue). Using controlled experimentation and one or both of multiple linear regression and binary logistic regression models performed using software sold under the registered trademark "MINITAB" by Minitab, Inc., algorithms for predicting lesion depth, determining the likelihood that the lesion has reached a predetermined depth (predicting whether a lesion has reached a predetermined depth), and predicting the temperature of the tissue at a given depth below the tissue surface were derived corresponding to the particular equipment and arrangement of the system 10 used in the experimentation and analysis, each of which will be described separately below. Factors that were evaluated in the testing and analysis for one or all of the algorithms included, but were not necessarily limited to: the magnitude of the instantaneous RF power applied to the tissue during lesion formation; the natural log of the applied power; the average power applied during the lesion formation process; the natural log of the average power applied during lesion formation; the duration of the lesion formation process; the natural log of the duration of the lesion formation process; the magnitude of the phase angle ($\phi$) prior to the onset of lesion formation in the tissue; the pre-ablation magnitude of the phase angle ($\phi$) both prior to and following contact between the catheter 18 and the tissue 12; the magnitude of the resistance (R), reactance (X), and impedance (Z) following lesion formation; the changes in R, X, and $\phi$ from the onset of lesion formation (i.e., just after the application of RF power) to the end of lesion formation, or to a point in time subsequent to the start of lesion formation and prior to the end of lesion formation; the magnitude of an electrical coupling index (ECI) of the tissue; the magnitude of the change in ECI from the onset of lesion formation to the end of lesion formation; the electrical current (I); and the catheter temperature (T). Regression models including some or all of the factors were created first, and then certain factors were eliminated. After the elimination of a factor, the models were re-run, and the process was repeated.

With respect to the lesion depth prediction algorithm, once this process was completed, it was generally determined that for predicting the depth of a lesion formed in the tissue 12 using the particular equipment and arrangement of the system 10 used in the experimentation and analysis (as opposed to, for example, predicting the temperature of the tissue, which will be described in greater detail below), the resistance (R) and phase angle ($\phi$) components of the complex impedance between the electrode 16 and the tissue 12; the average power applied to the tissue 12; and the duration of the lesion formation process, or change in time from the start of the lesion formation process to the point in time the lesion depth is assessed, were preferred factors to be considered in the algorithm. More specifically, it was determined that the natural log of the average power applied to the tissue during the lesion formation process; the change in time between the start of the lesion formation process and the point in time during or after the lesion formation process at which the predicted depth is calculated (dt); the phase angle prior to the onset of the lesion formation process (pre-ablation $\phi$); the change in resistance (dR) and phase angle (d$\phi$) from the start of the formation of a lesion (i.e., just after the application of RF power to the tissue 12) to the end of the lesion formation process, or at least a subsequent point in time in the formation process of the same lesion at which the predicted lesion depth is calculated, were the most significant factors to be considered in the context of the equipment used for testing.

It was further determined that various other factors would possibly have an impact on the accuracy of the prediction algorithm. These factors include, for example and without limitation, certain parameters and/or characteristics of the equipment and/or arrangement of the system 10 (such as, for example, the type of catheter and ablation generator being used, the irrigation flow rate, etc.).

Accordingly, it was determined that the most computationally efficient algorithm would be based on the "electrical" factors above (i.e., resistance, phase angle, power magnitudes, etc.), as well as certain predetermined coefficients and constants to account for design parameters or characteristics of the devices/equipment used in the ablation procedure. More specifically, it was determined that the best equation or algorithm was the equation (3):

$$\text{Predicted Depth} = a + b_1(\ln \text{Avg.}P) + b_2(dt) + b_3(\text{pre-ablation } \phi) + b_4(dR) + b_5(d\phi) \quad (3)$$

In this equation, the constant a and the coefficients $b_1$-$b_5$ are predetermined values that are intended to account for the various factors associated with, for example, the equipment used in the ablation procedure (i.e., type of catheter and/or ablation generator, irrigation flow rate, etc.). The constant and coefficients, which may be positive or negative values depending on the circumstances, can be determined in a number of ways, such as, for example, controlled experimentation or using analyses, such as, for example, a regression analysis. Once the constant and coefficients are determined, they may be stored or programmed into the ECU 34, or a memory/storage device 73 (best shown in FIG. 1) associated therewith or accessible thereby. Alternatively, the catheter 18 may itself include a memory such as an EEPROM that stores numerical values for the coefficients/constant corresponding to that particular type of catheter and/or other equipment of the system 10, or stores a memory address for accessing the numerical values in another memory location. The ECU 34 may retrieve these values or addresses directly or indirectly and factor them into the calculation accordingly.

It should be understood that while the coefficients and constant of the particular equation above may vary depending on, among other things, the specific catheter used, the ablation generator employed, the irrigation flow rate, potentially the patient, other equipment in the system, the species being treated, and the like, the value calculated using the particular equation above will always be responsive to components of the complex impedance and the RF power applied to the tissue in order to arrive at an optimal assessment of the predicted lesion depth in the tissue 12 during an ablation procedure performed thereon.

By way of example and illustration, employing the experimental testing and regression analysis described above, and using a RF ablation catheter available from St. Jude Medical, Inc. under the name "GEN3" and a 485 kHz RF ablation generator, the best prediction of lesion depth for a system employing those particular components was determined to be the following equation (4):

$$\text{Predicted Depth} = -12.1 + 1.92(\ln \text{Avg.}P) + 1.94(dt) - 0.454(\text{pre-ablation } \phi) + 0.0450(dR) + 0.384(d\phi) \quad (4)$$

Figure 5:
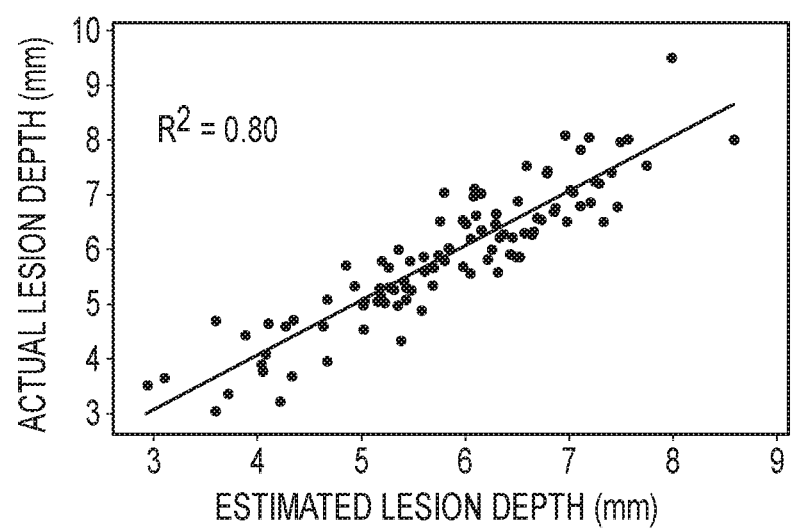
FIG. 5 is a chart illustrating results of validation testing of an exemplary lesion depth prediction algorithm.

This was determined by bench and/or animal testing that included testing on bovine myocardium, in-vivo testing in swine thighs, and in-vivo testing in the cardiac surfaces of swine. Data was collected and a regression model was performed to come to equation (4), and the values of the constant and coefficients thereof. With reference to FIG. 5, it was determined through testing that the algorithm represented by equation (4) accounted for 80% of the variability observed in lesion depth (i.e., $R^2 = 0.80$).

As briefly described above, the particular equipment being used impacts the form and composition of the lesion depth prediction algorithm. For example, using equipment different than that which was used to derive equations (3) and (4) above, it was determined that for the particular equipment used, the most computationally efficient algorithm would be based on the duration of the lesion formation process and the "electrical" factors of resistance (R), electrical current (I), and reactance (X), as well as certain predetermined coefficients and constants to account for design parameters or characteristics of the devices/equipment used in the ablation procedure. More specifically, it was determined that the natural log of the change in time between the start of the lesion formation process and the point in time during or after the lesion formation process at which the predicted depth is calculated (dt); the change in resistance (dR) and reactance (dX) from the start of the formation of a lesion (i.e., just after the application of RF power to the tissue 12) to the end of the lesion formation process, or at least a subsequent point in time in the formation process of the same lesion at which the predicted lesion depth is calculated, and an electrical current value calculated by taking the square root of the quotient of the division of the average power applied to the tissue 12 during the lesion formation process by the value of the resistance (R) between the electrode 16 and the tissue 12 just after the start of the lesion formation process $$\left(\text{i.e., } \sqrt{\frac{Avg.P}{R}}\right)$$

were the most significant factors to be considered in the algorithm.

As with equation (3) above, it was further determined that various other factors would possibly have an impact on the accuracy of the prediction algorithm. These factors include, for example and without limitation, certain parameters and/or characteristics of the equipment and/or arrangement of the system 10 (such as, for example, the type of catheter and ablation generator being used, the irrigation flow rate, etc.).

Accordingly, it was determined that the most computationally efficient algorithm would be based on the "electrical" factors above (i.e., resistance, reactance, electrical current, etc.), as well as certain predetermined coefficients and constants to account for design parameters or characteristics of the devices/equipment used in the ablation procedure. More specifically, it was determined that the best equation or algorithm was the equation (5):

Predicted Depth=$a+b_1(\ln dt)+b_2(dR)+b_3 I+b_4(dX)$ (5)

As with equation (3) above, in this equation, the constant a and the coefficients $b_1$-$b_4$ are predetermined values that are intended to account for the various factors associated with, for example, the equipment used in the ablation procedure (i.e., type of catheter and/or ablation generator, irrigation flow rate, etc.). The constant and coefficients, which may be positive or negative values depending on the circumstances, can be determined in a number of ways, such as, for example, controlled experimentation or using analyses, such as, for example, a regression analysis. Once the constant and coefficients are determined, they may be stored or programmed into the ECU 34, or a memory/storage device 73 (best shown in FIG. 1) associated therewith or accessible thereby. Alternatively, the catheter 18 may itself include a memory such as an EEPROM that stores numerical values for the coefficients/constant corresponding to that particular type of catheter and/or other equipment of the system 10, or stores a memory address for accessing the numerical values in another memory location. The ECU 34 may retrieve these values or addresses directly or indirectly and factor them into the calculation accordingly.

It should be understood that while the coefficients and constant of the particular equation above may vary depending on, among other things, the specific catheter used, the ablation generator employed, the irrigation flow rate, potentially the patient, other equipment in the system, the species being treated, and the like, the value calculated using the particular equation above will always be responsive to components of the complex impedance and the RF power applied to the tissue in order to arrive at an optimal assessment of the lesion depth in the tissue 12 during an ablation procedure performed thereon. It should be further noted that the constant and coefficients are determined and programmed as part of the manufacturing and/or setup process of the system 10, and thus, are not determined during the use of the system 10 in accordance with its intended purpose.

By way of example and illustration, employing the experimental testing and regression analysis described above, and using a RF ablation catheter available from St. Jude Medical, Inc. under the name "Cool Path" and a 485 kHz RF ablation generator, the best prediction of lesion depth for a system employing those particular components was determined to be the following equation (6):

Predicted Depth=$-5.03+1.07(\ln dt)+0.0721(dR)+7.06I+0.205(dX)$ (6)

Regardless of the particular equation or algorithm employed, once calculated, the predicted lesion depth may be used or displayed in a number of ways, as will be described in greater detail below. In view of the foregoing, it will be appreciated that while the specific composition or constituent components of the lesion depth prediction algorithm may change, the components of the complex impedance and the magnitude of the power applied during lesion formation are still determinative factors in predicting lesion depth.

It should be noted that although the equations above and the corresponding description above and below focus on the resistance (R), reactance (X), and phase angle ($\phi$) complex impedance components, it should be understood that the magnitude of impedance (|Z|) may be considered, or indeed any combination of the foregoing components of the complex impedance and derivatives or functional equivalents thereof, may be used in assessing lesion depth. For example, in addition to the values of the constant and coefficients of the predicted lesion depth equation above changing due to factors such as the type of catheter, the type of ablation generator, and other characteristics or parameters, these factors may also determine or impact which component or components of the complex impedance and/or aspects of the power are the most significant, and therefore, best for use in the equation for calculating the predicted lesion depth for lesion formation processes using certain equipment.

Further, while the equations set forth above are based on two components of the complex impedance (i.e., R and $\phi$ or R and X), in other exemplary embodiments the equation may be based on a single component, or more than two components of the complex impedance, and may include more or less terms than equations (3)-(6) above. Therefore, the present disclosure is not meant to be limited to the use of any particular complex impedance components, particular aspects of the RF power, or number of components. Rather, any equation used to calculate the predicted depth that is based on one or more components of one or more complex impedances, and one or more aspects of the power applied to the tissue 12 (e.g., average power, instantaneous power, etc.), remain within the spirit and scope of the present invention.

Once the particular complex impedance components to be used in the algorithm for a particular catheter or arrangement of the system 10 are determined and the form of the algorithm/equation is resolved, the components of the complex impedance (or an indication corresponding thereto), the equation to be used, and/or the specific terms of the equation (including, if appropriate, the constant(s) and/or coefficients for the equation terms) may be stored or programmed into the ECU 34, or a memory/storage device 73 (best shown in FIG. 1) associated therewith or accessible thereby. Alternatively, as described above, the catheter 18 or another component in the system 10 may include a memory, such as an EEPROM, that is configured to store the above identified information or a memory address for accessing the information stored in another memory location corresponding to that particular type of catheter and/or other equipment of the system 10. The ECU 34 may retrieve this information or addresses directly or indirectly and use it in the aforedescribed calculation.

Figure 6:
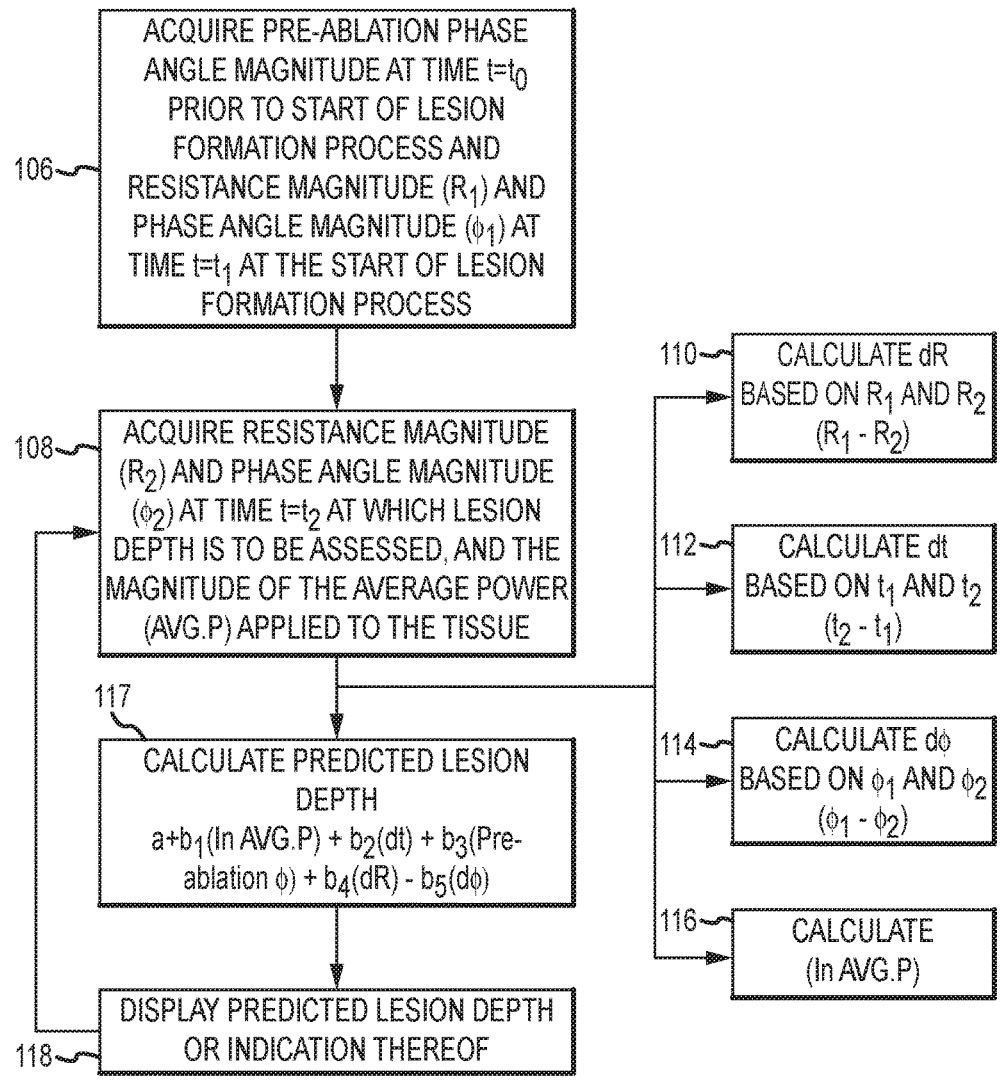
FIG. 6 is a flow chart illustrative of an exemplary embodiment of the methodology illustrated in FIG. 4 shown in greater detail.

With reference to FIG. 6, an exemplary lesion depth prediction calculation will be described. For purposes of clarity, brevity, and illustration, the description below has been limited to an embodiment wherein the lesion depth is calculated based using the equation (3) above. It will be appreciated in view of the above, however, that the present disclosure is not meant to be limited to such an embodiment.

As an initial matter, in addition to being configured to calculate the predicted lesion depth described above, in an exemplary embodiment the ECU 34 is also configured to acquire and/or calculate the terms used in the equation for making the calculation (i.e., average power, pre-ablation $\phi$, dt, dR, d$\phi$, etc.). As described above, and as illustrated in FIG. 4, in this embodiment, the ECU 34 is configured to acquire magnitudes for the first and second components of the complex impedance (i.e., R and $\phi$), the magnitude of power being applied to the tissue 12 during the lesion formation process (and, in this example, the magnitude of the average power applied, in particular), and the elapsed time of the lesion formation process. More particularly, with reference to FIG. 6, the ECU 34 is configured to acquire a magnitude for the pre-ablation phase angle $\phi_0$ between the electrode and tissue 12 at a point in time $t=t_0$ prior to the commencement of the lesion formation process. The ECU 34 is further configured to acquire magnitudes for the resistance $R_1$ and phase angle $\phi_1$ between the electrode 16 and the tissue 12 at a point in time $t=t_1$ at which the lesion formation process commences (i.e., just after initiation of RF power/energy delivery to the tissue 12). These values may be received from the complex impedance sensor 64, and may be correlated and/or stored along with the corresponding time (i.e., time $t=t_1$) in a temporary or permanent memory or storage medium that is either part of, or accessible by, the ECU 34, such as, for example, the memory 73.

The ECU 34 is further configured to acquire magnitudes for R and $\phi$ at a point in time $t=t_2$ at which the depth of a lesion formed or being formed is assessed ($R_2$, $\phi_2$), and the average RF power (Avg.P) applied to the tissue 12 from the start of the lesion formation process (i.e., time $t=t_1$) to when the lesion depth is assessed (i.e., time $t=t_2$). The R and $\phi$ magnitudes may be received from the complex impedance sensor 64, and the average power magnitude may be received from the ablation generator 26, a reporting system associated therewith, or may be calculated by the ECU 34. Each magnitude may then be correlated and/or stored along with the corresponding time (i.e., time $t=t_2$) in a memory or storage device such as that described above in the manner, for example, illustrated in FIG. 7.

Because the depth of a lesion may be assessed as it is being formed such that the lesion depth may be monitored in real-time, the ECU 34 is further configured to sample the magnitudes for R, $\phi$, and Avg.P throughout the formation of the lesion at one or more respective predetermined sampling rates in order to constantly and continuously monitor the predicted depth of the lesion. In an exemplary embodiment, a sampling rate on the order of 100 to 800 times per second may be used, however, the present disclosure is not meant to be limited to such a range of rates but rather a sampling rate that is greater than or less than 100 to 800 Hz may be used in different embodiments. Accordingly, the ECU 34 is configured to sample the signal received from the complex impedance sensor 64 at a predetermined rate and to store the corresponding R and $\phi$ values ($R_1$, $R_2$, . . . , $R_n$ and $\phi_1$, $\phi_2$, . . . , $\phi_n$) derived therefrom in the memory or storage medium described above along with the corresponding times (i.e., $t_1, t_2, \ldots, t_n$) at which the samples were taken (See FIG. 7). Similarly, the ECU 34 is configured to sample the signal received from the ablation generator 26, or an associated reporting system, at a predetermined rate and to store the corresponding power magnitudes and/or the magnitude of the average power (Avg.$P_1$, Avg.$P_2$, . . . , Avg.$P_n$) in a memory such as that described above along with the corresponding times (i.e., $t_1, t_2, \ldots, t_n$) at which the samples were taken (See FIG. 7). As briefly described above, in an exemplary embodiment, rather than the ablation generator 26 providing the magnitude of the average power applied, the ECU 34 may be configured to receive signals from the ablation generator 26 corresponding to the magnitude of the instantaneous power (P), and the ECU 34 may be configured to make the calculation to determine the average power (Avg.P) based on current and past power magnitudes.

In an exemplary embodiment, after a set of samples of R, $\phi$, and Avg.P is taken or acquired, the system 10 is configured to calculate the predicted lesion depth described above. Alternatively, rather than calculating the predicted depth after each set of samples, the ECU 34 may be configured to calculate the predicted depth at some other rate, such as after a certain number of sets of samples have been collected, after a certain amount of time has elapsed, upon receiving instructions from the user to do so, or after the lesion formation process has been completed. For the purposes of clarity and brevity alone, the description below will be directed to an embodiment wherein the predicted depth is calculated after a set of samples of each of the R, $\phi$, and Avg.P is collected at a particular point in time (i.e., time $t=t_2$). It will be appreciated, however that the present invention is not meant to be limited to such an embodiment.

Accordingly, after a set of samples of each of R, $\phi$, and Avg.P are collected, the ECU 34 is configured to perform a number of calculations. For example, and as illustrated in FIG. 6, the ECU 34 is configured to calculate a change in the resistance (dR) (Step 110), a change in the time (i.e., the elapsed time) represented by the time interval from the point in time that the lesion formation process commenced to the point in time that the current sample was taken (dt) (Step 112), a change in the phase angle (d$\phi$) (Step 114), and the natural log of the magnitude of the average power (Avg.P) applied to the tissue during the lesion formation process (Step 116).

With respect to the change in resistance, the ECU 34 is configured to calculate the change in resistance over the time interval beginning at the point in time at which the lesion formation process commences (i.e., just after initiation of RF power/energy delivery to the tissue 12) (time $t=t_1$), to the point in the time corresponding to the current resistance value (time $t=t_2$). Therefore, with reference to FIG. 6, if the predicted depth is being calculated using the values sampled at time $t=t_2$, the change in resistance is calculated by subtracting the resistance $R_2$ from the resistance $R_1$. Accordingly, the ECU 34 is configured to acquire resistance values $R_1$ and $R_2$ and to perform the calculation to determine the change in resistance. Similarly, if the index is being calculated at time $t=t_3$, the change in resistance is calculated by subtracting the resistance $R_3$ from the resistance $R_1$, and so on and so forth. Accordingly, regardless of the point in time of the lesion formation process at which the predicted depth is being calculated, the current resistance value is processed with resistance value $R_1$ to determine the change in resistance (dR).

With respect to the change in time, the ECU 34 is configured to calculate the change in time or the elapsed time represented by the time interval from the point in time that the lesion formation process commenced (time $t=t_1$) to the point in time that the current samples were taken, and therefore, the point in time that the predicted depth is being calculated. Accordingly, if the predicted depth is being calculated using the values sampled at time $t=t_2$, the change in time is calculated by subtracting the time $t_1$ from the time $t_2$ to determine the elapsed time of the procedure thus far. Accordingly, the ECU 34 is configured to acquire the times corresponding to $t_1$ and $t_2$ and to perform the calculation to determine the change in time or the amount of elapsed time. Similarly, if the predicted depth is being calculated at time $t_3$, the change in time is calculated by subtracting the time $t_1$ from the time $t_3$, and so on and so forth. Accordingly, regardless of the point in time of the lesion formation process at which the predicted depth is being calculated, the current time value is always processed with the time value $t_1$ to determine the change in time (dt).

With respect to the change in phase angle, the ECU 34 is configured to calculate the change in phase angle over the time interval beginning at the point in time at which the lesion formation process commences (i.e., just after RF power is applied to the tissue 12) (time $t=t_1$), to the point in the time corresponding to the current phase angle magnitude. Therefore, if the predicted depth is being calculated using the magnitudes sampled at time $t=t_2$, the change in phase angle is calculated by subtracting the phase angle $\phi_2$ from the phase angle $\phi_1$. Accordingly, the ECU 34 is configured to acquire phase angle magnitudes $\phi_1$ and $\phi_2$ and to perform the calculation to determine the change in phase angle. Similarly, if the predicted depth is being calculated at time $t=t_3$, the change in phase angle is calculated by subtracting the phase angle $\phi_3$ from the phase angle $\phi_1$, and so on and so forth. Accordingly, regardless of the point in time of the lesion formation process at which the predicted lesion depth is being calculated, the current phase angle magnitude is processed with phase angle magnitude $\phi_1$ to determine the change in phase angle (d$\phi$).

Once all of the terms above are calculated, the ECU 34 is configured and able to calculate the predicted depth of the lesion at that point in time (Step 117). Accordingly, using equation (3) above as an example, the ECU 34 is configured to acquire the correct or appropriate values for the constant a and the coefficients $b_1$-$b_5$, and to process these values with the terms described above to come to a predicted lesion depth. Accordingly, the computer program stored or accessible by the ECU 34 includes code for carrying out the execution of the predicted depth equation. Once the predicted lesion depth is calculated, it may be used in a number of ways.

In an exemplary embodiment, once the predicted lesion depth is calculated, it may be displayed (Step 118) in visual form for the user of the system 10 to see. In one exemplary embodiment illustrated, for example, in FIG. 8a, the predicted lesion depth may be displayed in numerical form (e.g., a digital readout) on the display 36 of the visualization, mapping, and navigation system 32. The display 36 may be provided to present information regarding the predicted lesion depth in a format useful to the user (e.g., clinician) of the system 10. By using the display 36 of the visualization, mapping, and navigation system 32, information regarding the predicted lesion depth may be displayed and communicated to the user (i.e., physician or clinician using the system 10) in a concise, succinct, and easily understandable format. Moreover, by using the display 36 of the visualization, mapping, and navigation system 32, the number of monitors and/or amount of equipment is minimized and the user (i.e., physician or clinician using the system 10) is not defocused from the information provided by the visualization, mapping, and navigation system 32, such as catheter manipulation and placement in the cardiac anatomy. In an embodiment of the invention, the information regarding the predicted lesion depth may be displayed and communicated as an inset and/or sub window on the display device 36 of the visualization, mapping, and navigation system 32. Although the display 36 of the visualization, mapping, and navigation system 32 may be used to display information regarding the predicted lesion depth, other display devices may be used in accordance with other embodiments of the system 10. For example and without limitation, the display device may comprise a separate LCD monitor or any other conventional display device known to those of ordinary skill in the art.

Figure 8A:
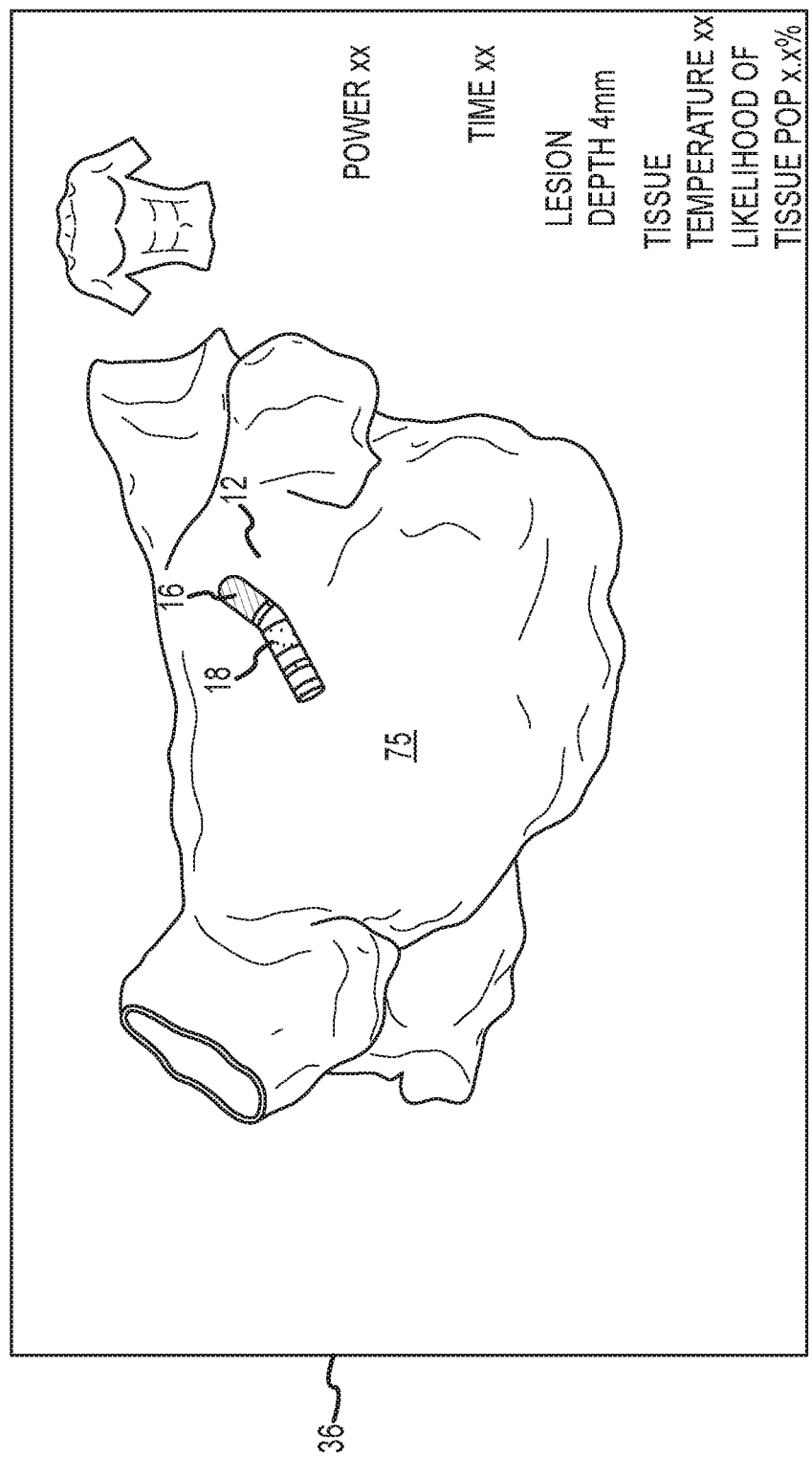
FIGS. 8a-8n are exemplary embodiments of screen displays illustrating possible formats for presenting predicted lesion depths calculated using the methodology of FIG. 6.
Figure 8B:
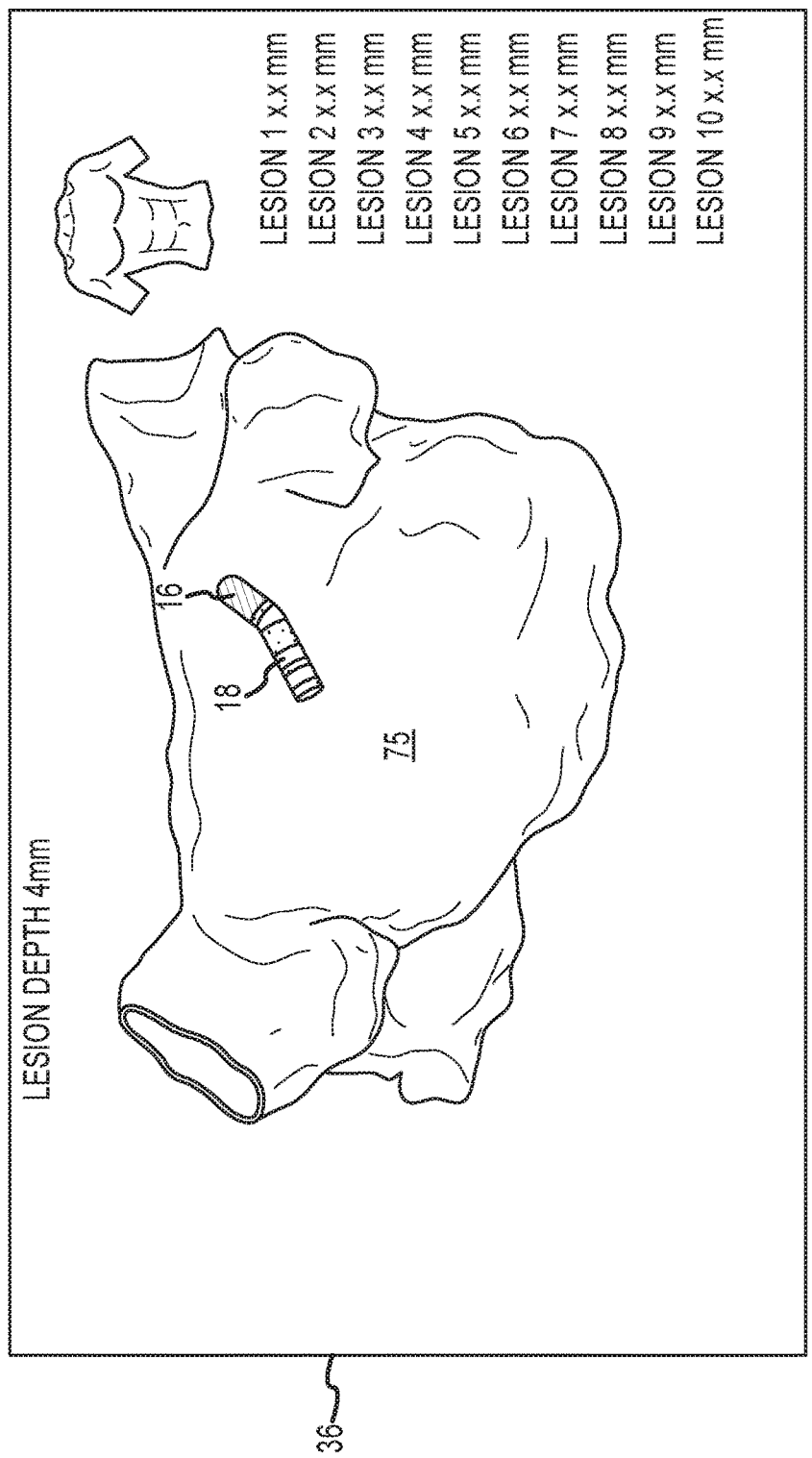

This embodiment in which information regarding the predicted lesion depth is displayed provides the user (i.e., physician or clinician using the system 10) with a real-time indication of lesion depth. In particular, the ECU 34 of the system 10 may receive a plurality of input signals for a time period. The system 10 may be configured to display information regarding the predicted lesion depth based on the input signals for the time period during the time period, so as to provide real-time information regarding lesion depth. Accordingly, if the ECU calculates the predicted lesion depth to be 4 mm, a reading of "4 mm" will be displayed on the display 36. Additionally, as illustrated in FIG. 8b, in an exemplary embodiment, the current calculated predicted lesion depth may be displayed along with a log of previously calculated predicted depths so as to provide the user of the system 10 with a history of calculated depths. For example, each of the previously calculated predicted lesion depths may be stored along with the corresponding time (i.e., $t_2$, $t_3$, . . . , $t_n$) in a temporary or permanent memory or storage medium that is either part of, or accessible by, the ECU 34, such as, for example, the memory 73. The ECU 34 may then be configured to retrieve one or more of the previously calculated predicted lesion depths for display on the display 36.

Figure 8C:
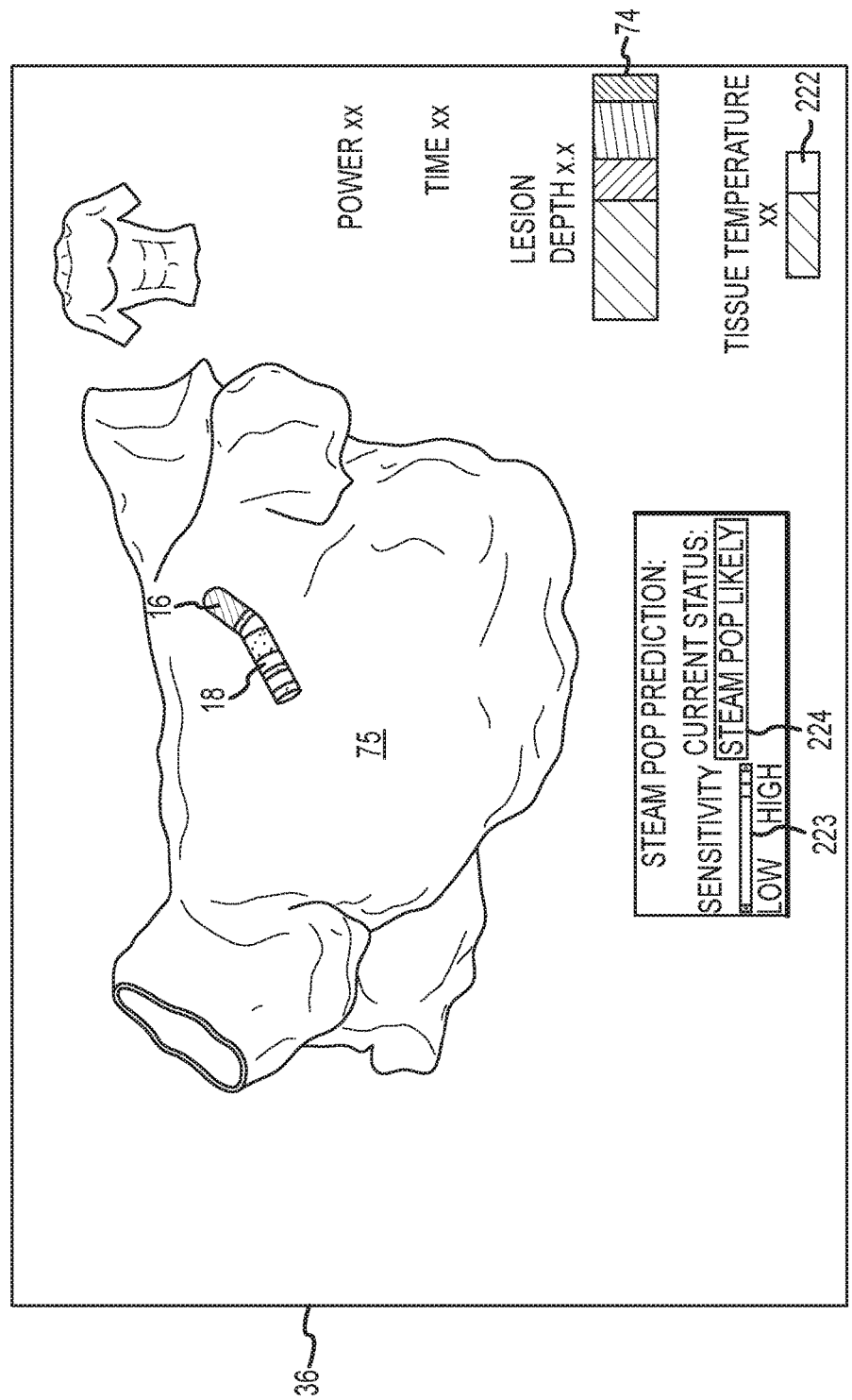

In another exemplary embodiment illustrated, for example, in FIG. 8c, the numeric representation of the calculated predicted lesion depth may be displayed on a display, such as, for example, the display 36, along with a visual representation 74 indicative of the calculated predicted lesion depth. Although FIG. 8c includes both the numeric representation of the calculated predicted lesion depth along with the visual representation 74, only the visual representation 74 may be displayed in accordance with other embodiments of the system 10. As illustrated in FIG. 8c, the visual representation 74 may comprise a graph. Although a bar graph is illustrated in detail, the visual representation 74 may comprise any number of other visual representations. The visual representation 74 may be configured to provide a visual indication as to where the predicted depth falls within a spectrum of one or more predetermined targets or thresholds. For example, in one exemplary embodiment, the system 10 may be preprogrammed with one or more predetermined depth targets or thresholds to which the predicted depth is compared. Alternatively, the user of the system 10 may set or adjust these targets. For example, one predetermined depth target or threshold to which the predicted depth may be compared is the thickness of the target tissue. The thickness of the target tissue may be obtained using any number of techniques and methods known to those of ordinary skill in the art. For example, tissue thickness of the target tissue may be obtained using imaging techniques, such as magnetic resonance imaging (MRI), prior to the ablation procedure being performed on the target tissue. Tissue thickness of the target tissue may also be obtained using intracardiac echocardiography (ICE) using, for example, A mode or B mode ultrasonographic technology. For another example, tissue thickness of the target tissue may be estimated by a clinician based on previous experience, published anatomical data, and the like. Although particular methods for obtaining information regarding tissue thickness are described in detail, there are a number of other methods to obtain tissue thickness known to those of ordinary skill in the art and any of these methods can be used in accordance with other embodiments of the invention. The information regarding tissue thickness of the target tissue may be input into ECU 34 through the input interface of the ECU 34. The input interface may comprise a keyboard and/or a graphical pointing device, such as a mouse, in accordance with an embodiment of the invention. The input interface may thus be configured to allow a user (e.g., clinician) of the system 10 to input, set, and/or adjust the information regarding tissue thickness of the target tissue in the ECU 34. In accordance with another embodiment of the system 10, the system 32 for visualization, mapping, and navigation of internal body structures may include software configured to import images obtained through Mill and/or computed tomography (CT). The software may comprise software sold under the name EnSite Fusion™ and commercially available from St. Jude Medical, Inc. It may be possible for information regarding tissue thickness of the target tissue to be input into ECU 34, for example, by direct importation of the images obtained through MM and/or CT using software or by a direct measurement method (e.g., using an ICE catheter).

Figure 8D:
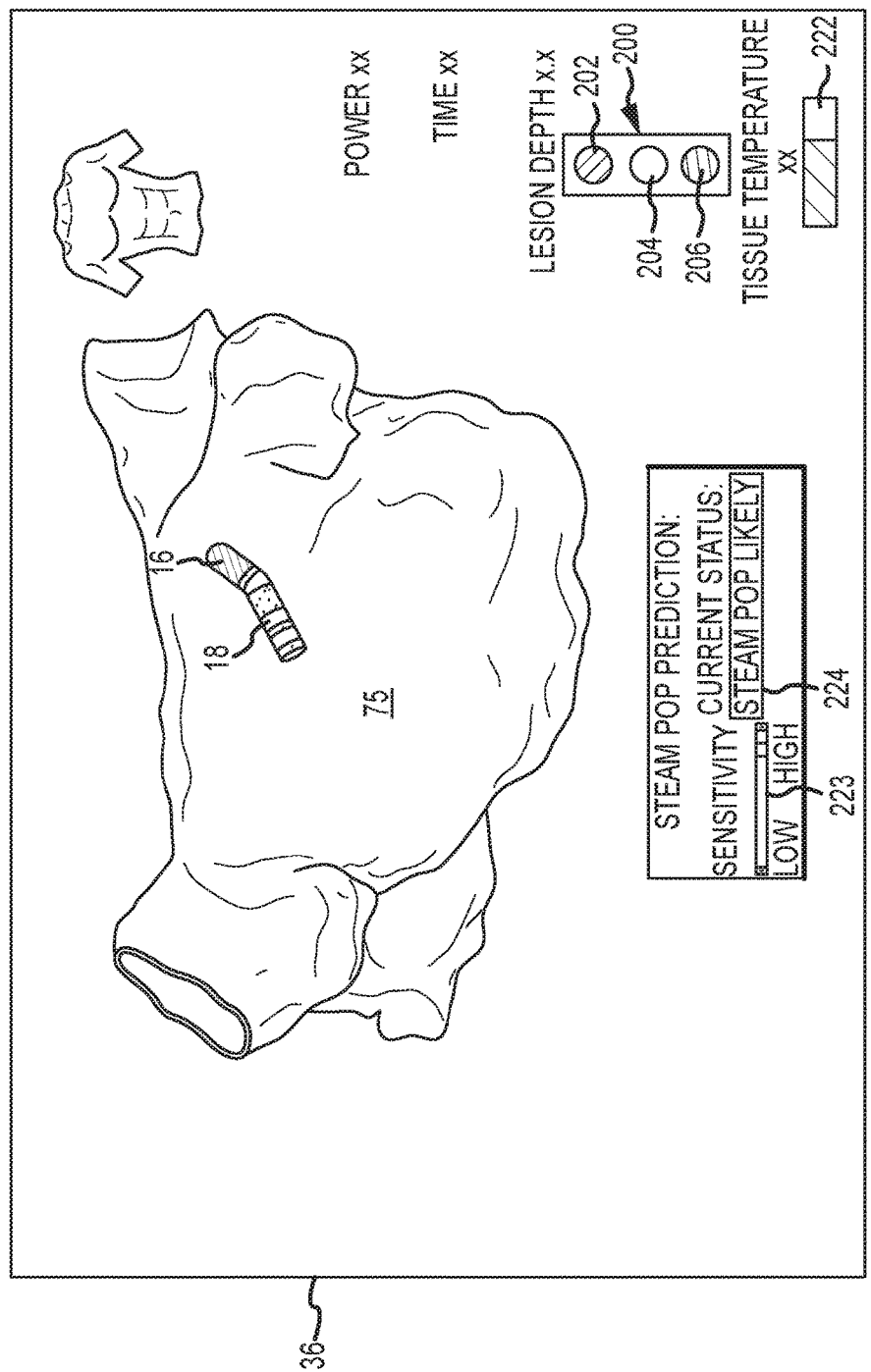

For each target/threshold, a color or some other indicator may be assigned. For example, if there are three targets, a first may be deemed to be an insufficient depth and be assigned the color green, a second may be deemed to be a sufficient or desired depth and be assigned the color yellow, and a third may be deemed to be an excessive depth and be assigned the color red. As a predicted depth is calculated, it may be compared to the predetermined thresholds/targets and then the visual representation (e.g., graph) 74 may present the appropriate color. Accordingly, as the lesion formation process progresses, the graph changes to illustrate where the current lesion is on the spectrum. In an embodiment, the information regarding the calculated predicted lesion depth may be displayed in a visual representation 200 comprising three, vertically stacked, circular images 202, 204, 206 resembling a "stop light" design in which a different color is displayed on the display 36 in the corresponding circular image 202, 204, 206, depending upon the calculated predicted lesion depth as generally illustrated in FIG. 8d. For example, the system 10 may be programmed with a first color (e.g., red) associated with a first range of measurements for the calculated predicted lesion depth; a second color (e.g., yellow) associated with a second range of measurements for the calculated predicted lesion depth; and a third color (e.g., green) associated with a third range of measurements for the calculated predicted lesion depth. In other embodiments, the user of the system 10 may set or adjust these colors and/or ranges of measurements. The color associated with the calculated predicted lesion depth may then be displayed and/or illuminated on the display 36 in the "stop light" design in one of the corresponding circular images 202, 204, 206. Although three colors (i.e., red, yellow, and green) and vertically stacked, circular images are used in accordance with a "stop light" design, the number of colors and the specific colors, as well as the configuration of the design may vary in accordance with other embodiments of the invention.

Figure 8E:
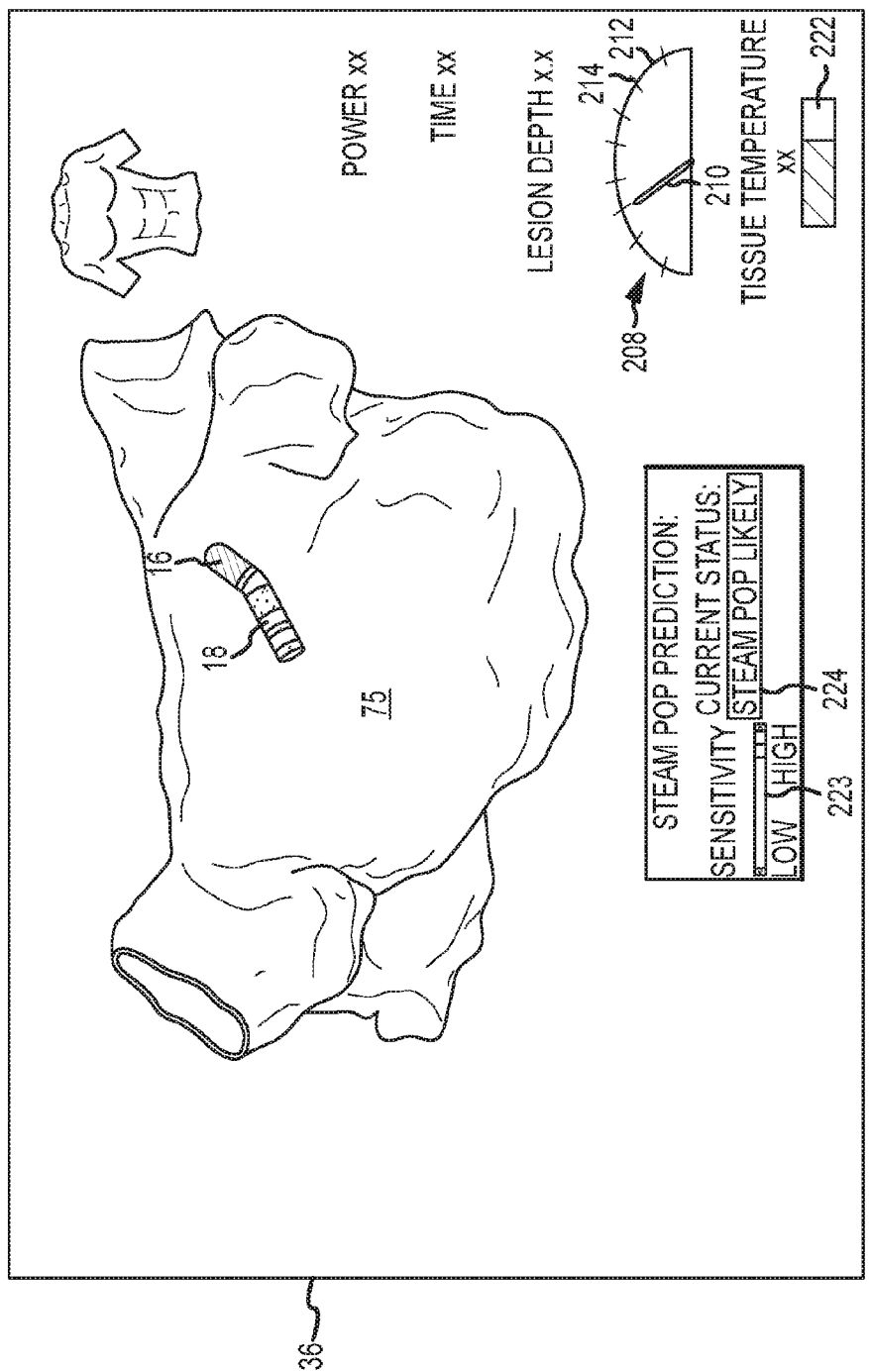
Figure 8F:
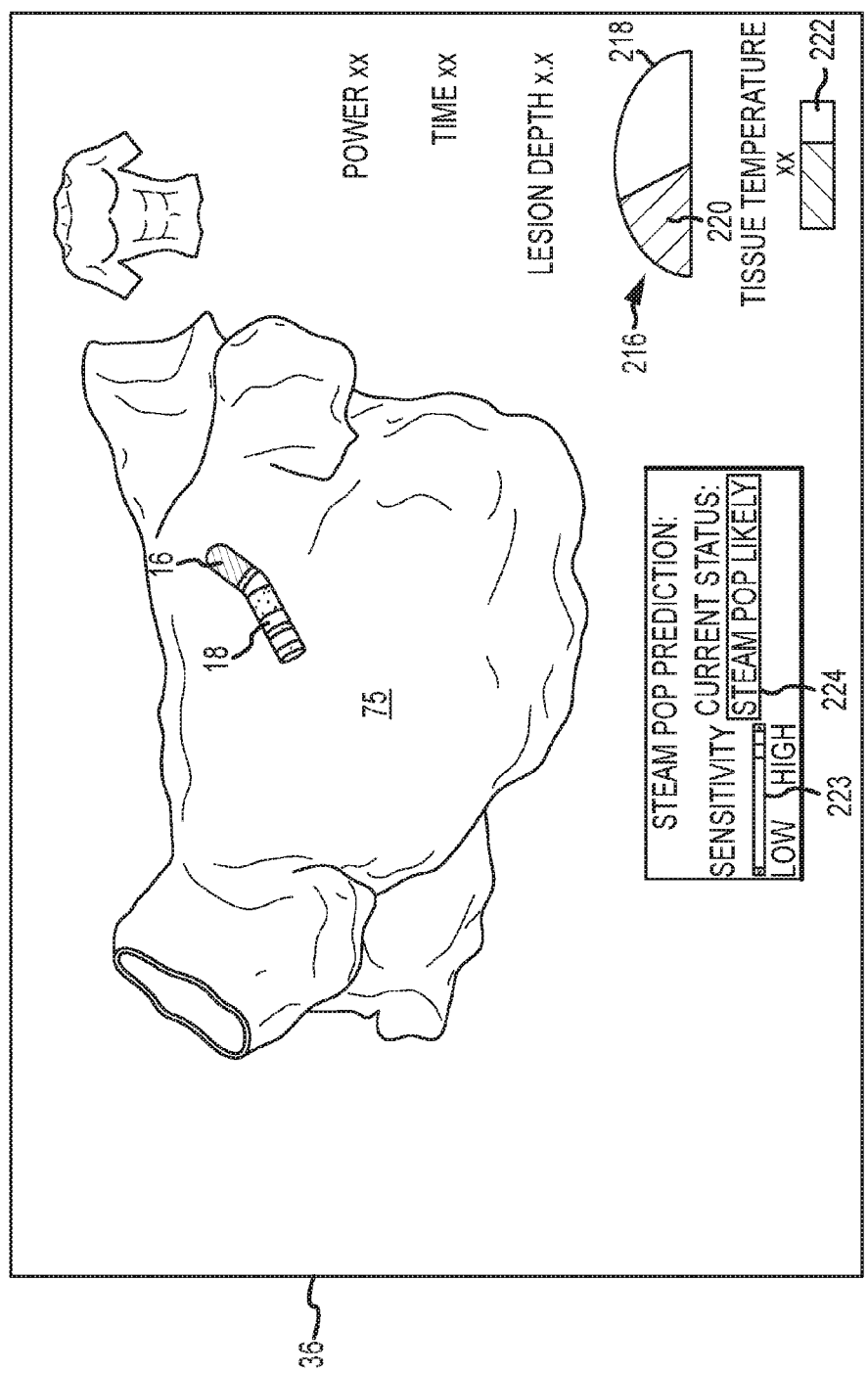

In another exemplary embodiment, an indicator needle displayed on the display device 36 may be used to indicate the current status of the lesion relative to the spectrum. For example, as generally illustrated in FIG. 8e, a visual representation 208 may comprise an indicator needle 210 that may be movable along a scale 212. Scale 212 may include hash marks 214 corresponding to the calculated predicted lesion depth in accordance with an embodiment of the invention. However, hash marks 214 may be removed in other embodiments of the invention. Visual representation 208 may generally resemble a "gas tank gauge." In this embodiment, the indicator needle 210 may read "empty" when the depth of the calculated predicted lesion is zero or low. As the depth of the calculated predicted lesion increases, the indicator needle 210 may read "full." The indicator needle 210 may read 'full" once the depth of the calculated predicted lesion depth substantially equals the tissue thickness of the target tissue in accordance with an embodiment of the invention. The calculated predicted lesion depth may also be shown by the scale 212 changing appearance, color, shape, and/or size in accordance with various embodiments of the invention. Referring now to FIG. 8f, the visual representation 216 may comprise a scale 218 in which colors and/or shading 220 may be used to indicate the depth of the calculated predicted lesion depth. Multiple colors and/or shading could be used in connection with scale 218 in accordance with other embodiments of the invention, and again, the calculated predicted lesion depth may also be shown by the scale 218 changing appearance, color, shape, and/or size in accordance with various embodiments of the invention.

As described hereinabove, one predetermined depth target or threshold to which the predicted depth may be compared is the thickness of the target tissue, which may be input into ECU 34 in any manner that is known to those of ordinary skill in the art. In an exemplary embodiment of a screen display, one possible format for presenting predicted lesion depth is a visual representation 222 comprising a graph and/or meter 224. The graph and/or meter 224 may be an expanding bar graph that increases in size as the predicted calculated depth of the lesion increases. Although the graph and/or meter 224 is shown as an expanding rectangular bar graph in FIGS. 8g-8j, the graph and/or meter 224 may be any number of other shapes or formats in other embodiments of the invention. For example, lesion progression could be more complex based on the algorithm and/or methodology used in connection with system 10, and the graph and/or meter 224 could be, for example and without limitation, ellipsoidal in shape. Although an ellipsoidal shape is mentioned in detail, the graph and/or meter 224 could be any number of other shapes in accordance with other embodiments of the invention.

Figures 8G, 8H, 8I, 8J:
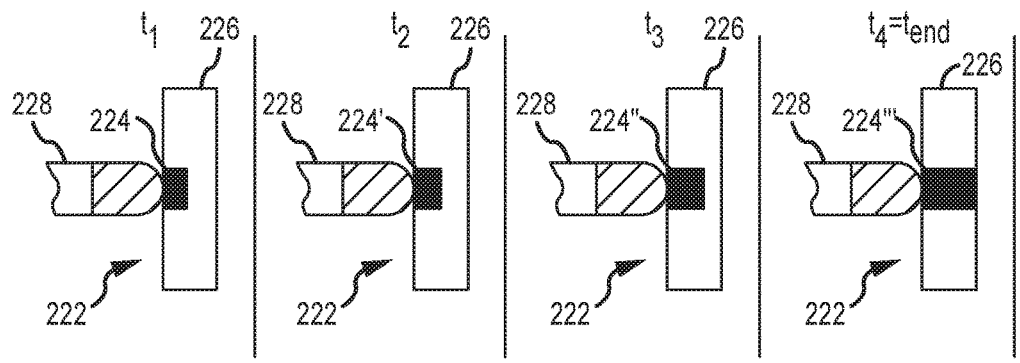

In accordance with an embodiment of the invention, the graph and/or meter 224 may be overlaid on a visual representation 226 of the target tissue or anatomy. In particular, the visual representation 226 of the target tissue or anatomy may be indicative of the thickness of the target tissue (e.g., the visual representation 226 of the target tissue may be thicker if the target tissue is thicker and the visual representation 226 of the target tissue may be less thick if the target tissue is less thick). The graph and/or meter 224 may be overlaid on the visual representation 226 of the target tissue and the length and/or size of the graph and/or meter may expand over the visual representation 226 of the target tissue as the calculated predicted depth of the lesion increases. Accordingly, the visual representation 222 may indicate the calculated predicted depth of the lesion relative to the thickness of the target tissue. Examples of display of lesion progression are shown in FIGS. 8g-8j. In particular, at time $t_1$, the graph and/or meter 224 shows that the lesion is a smaller percentage of the thickness of the target tissue as represented by visual representation 226. At time $t_2$, the graph and/or meter 224' shows that the lesion is a slightly larger percentage of the thickness of the target tissue as represented by visual representation 226. At time $t_3$, the graph and/or meter 224" shows that the lesion is an even slightly larger percentage of the thickness of the target tissue as represented by visual representation 226. At time $t_4$, the graph and/or meter 224''' shows that the lesion depth is substantially equal to the thickness of the target tissue as represented by visual representation 226. Thus, the lesion depth corresponds to substantially 100% of the thickness of the target tissue at time $t_4$. FIG. 8j thus presents a visual representation indicative of the transmurality of the lesion.

In addition to the visual representation indicative of the transmurality of the lesion as generally shown in FIG. 8j, there may be other visual indications of the transmurality of the lesion such as an alert or warning message on the display 36 indicating, for example, the words "Transmural Lesion", a light, a color change, blinking, any specialized image, and/or any of numerous other visual indications known to those of ordinary skill in the art used to indicate the transmurality of the lesion in the target tissue. In addition to and/or instead of the visual representation indicative of the transmurality of the lesion as generally shown in FIG. 8j (or other visual indications of the transmurality of the lesion), there may also be at least one of an audible indication (e.g., buzzer, alarm, audible message, etc.), a tactile indication, and/or a vibrational indication of the transmurality of the lesion. The audible indication, tactile indication, and/or vibrational indication may be used in connection with the catheter 18 (e.g., handle 44) in order to provide feedback to the user (e.g., clinician or physician) of the system 10.

As generally illustrated in FIGS. 8g-8j, the predicted lesion depth as a percentage of thickness of the target tissue may be displayed in concert with a visual representation 228 indicative of catheter 18. The visual representation 228 indicative of catheter 18 may be proximate one or both of the graph and/or meter 224 and the visual representation 226 indicative of the thickness of the target tissue in accordance with embodiments of the invention.

Figure 8K:
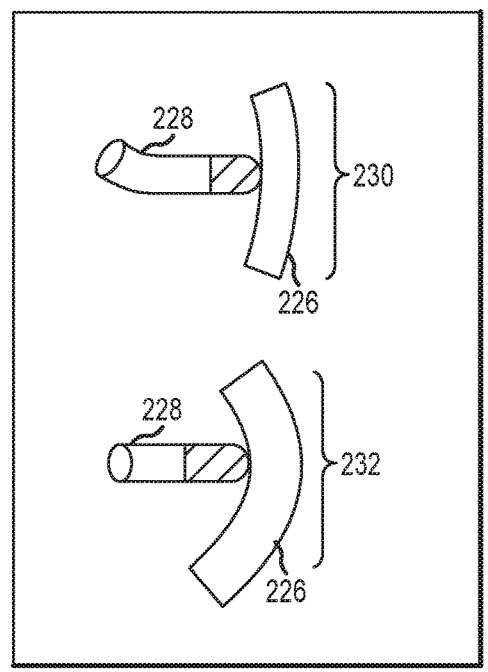
Figure 8I:
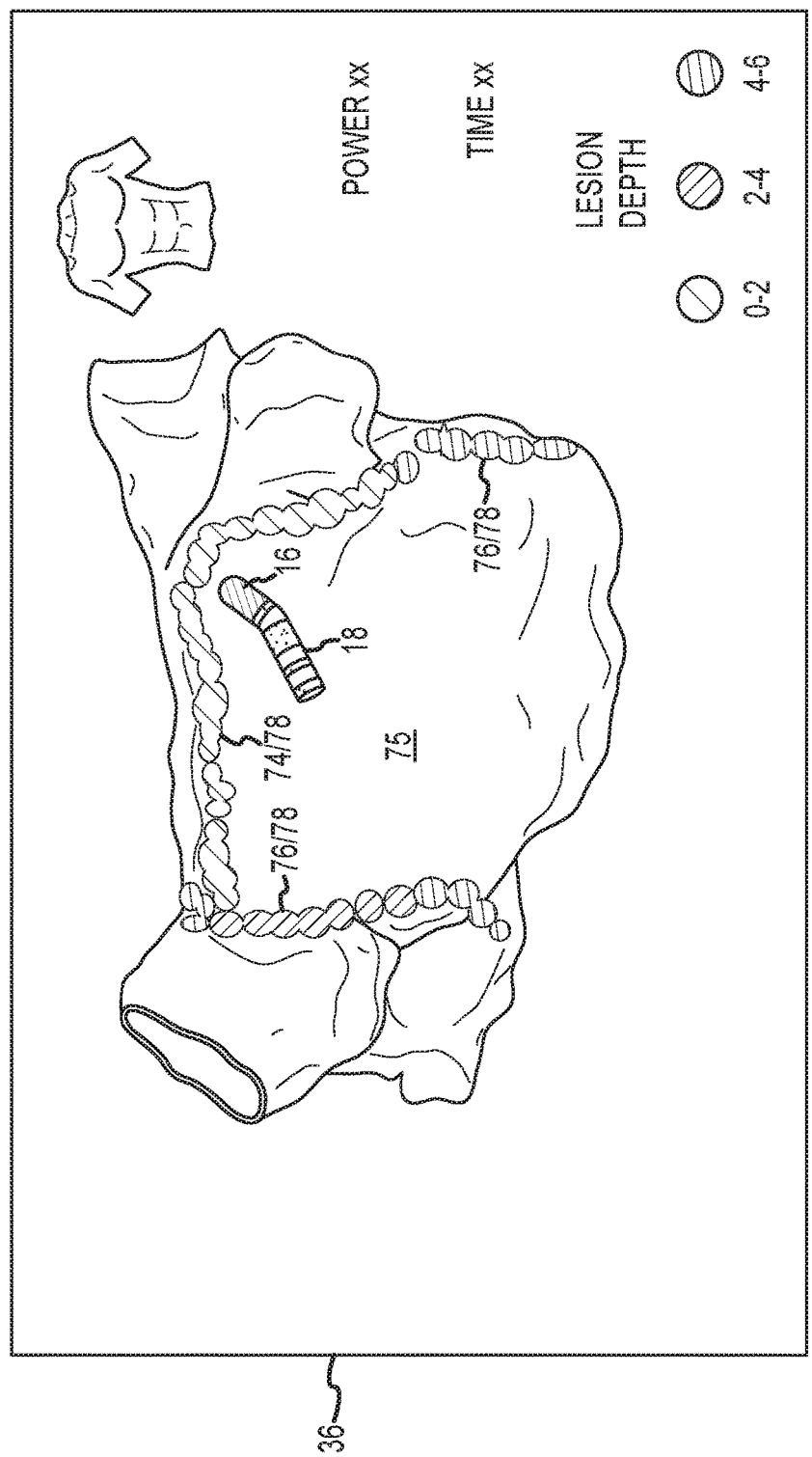

Referring now to FIG. 8k, the visual representation 226 of the target tissue or anatomy and the visual representation 228 indicative of catheter 18 may be displayed in multiple views along different axes. For example, the visual representations 226, 228 may be displayed in a first view 230 that is an axial view. The axial view may generally depict the visual representations 226, 228 along a head-to-toe axis of a body. Moreover, the visual representations 226, 288 may be displayed in a second view 232 that is a sagittal view. The sagittal view may generally depict the visual representations 226, 228 along a left-right axis of a body. Multiple views along multiple axes may assist the user (e.g., clinician or physician) with respect to maintaining the stability of the catheter 18.

As illustrated in FIGS. 8a-8f and 8l-8m, the predicted lesion depth calculation(s) may be displayed in concert with a model or image 75 (e.g., 2D or 3D image/model) of the anatomical structure that is being ablated (e.g., the heart or a portion thereof), as well as a real-time representation of the ablation catheter 18 on the model or image 75. In an exemplary embodiment, both the representation of the catheter 18 and the image/model 75 may be generated by, for example, the visualization, mapping, and navigation system 32. In another exemplary embodiment, each may be generated by separate and distinct systems that are configured for use in conjunction with each other.

Accordingly, in yet another exemplary embodiment illustrated, for example, in FIG. 8l, in addition to, or instead of, displaying the calculated predicted lesion depth on the display 36, the ECU 34, or another component of the system 10, may be configured to superimpose one or more markers 76 on the image/model 75 that are indicative of the predicted lesion depth calculated for the corresponding location on the anatomical structure. In one exemplary embodiment these markers 76 may be color coded such that a first color represents a lesion depth of a first magnitude or within a predetermined range, a second color represents a lesion depth of a second magnitude or within a second predetermined range, and so on. In another exemplary embodiment, rather than color coding the markers 76, different markers (e.g., different shapes, sizes, etc.) are used to differentiate between different predicted depths or depth ranges.

By placing markers 76 on the image/model 75, a lesion depth map may be created and presented to the user of the system 10 on the display 36 to evaluate the depth of the lesion(s) formed in the tissue 12. In order to place the markers 76 in the correct location(s), the system 10 must correlate each calculated predicted lesion depth with the location on the anatomical structure at which the measurements corresponding to the calculated predicted depth were taken.

One exemplary method by which this may be done is as described in U.S. Pat. No. 7,263,397 entitled "Method and Apparatus for Catheter Navigation and Location and Mapping in the Heart," which was incorporated by reference above. In general terms, however, an electric field is generated in the area in which the tissue being ablated is disposed. As the electrode 16 of the catheter 18 is moved along the tissue 12 within the electric field, the location of electrode 16 is monitored by the system 32 and using various known algorithms, the position of electrode 16 is determined and recorded by system 32 as a location point 78. A location point may be determined for each location at which a predicted depth calculation is made, and the location point 78 and the corresponding depth calculation may be correlated together and stored in a memory, such as, for example, the memory 73. The ECU 34 may then use the location point(s) 78 to superimpose a marker(s) 76 onto the image/model 75 in the correct position(s) wherein each marker corresponds to, and is representative of, the calculated predicted depth (e.g., the marker may be of a predetermined color or take a predetermined form corresponding to the calculated predicted depth, for example). It will be appreciated that while the description above is limited to an electric-field based location system, those of ordinary skill in the art will appreciate that other systems, such as, for example, magnetic field-based location systems, may be used, and therefore, remain within the spirit and scope of the present disclosure.

Figure 8M:
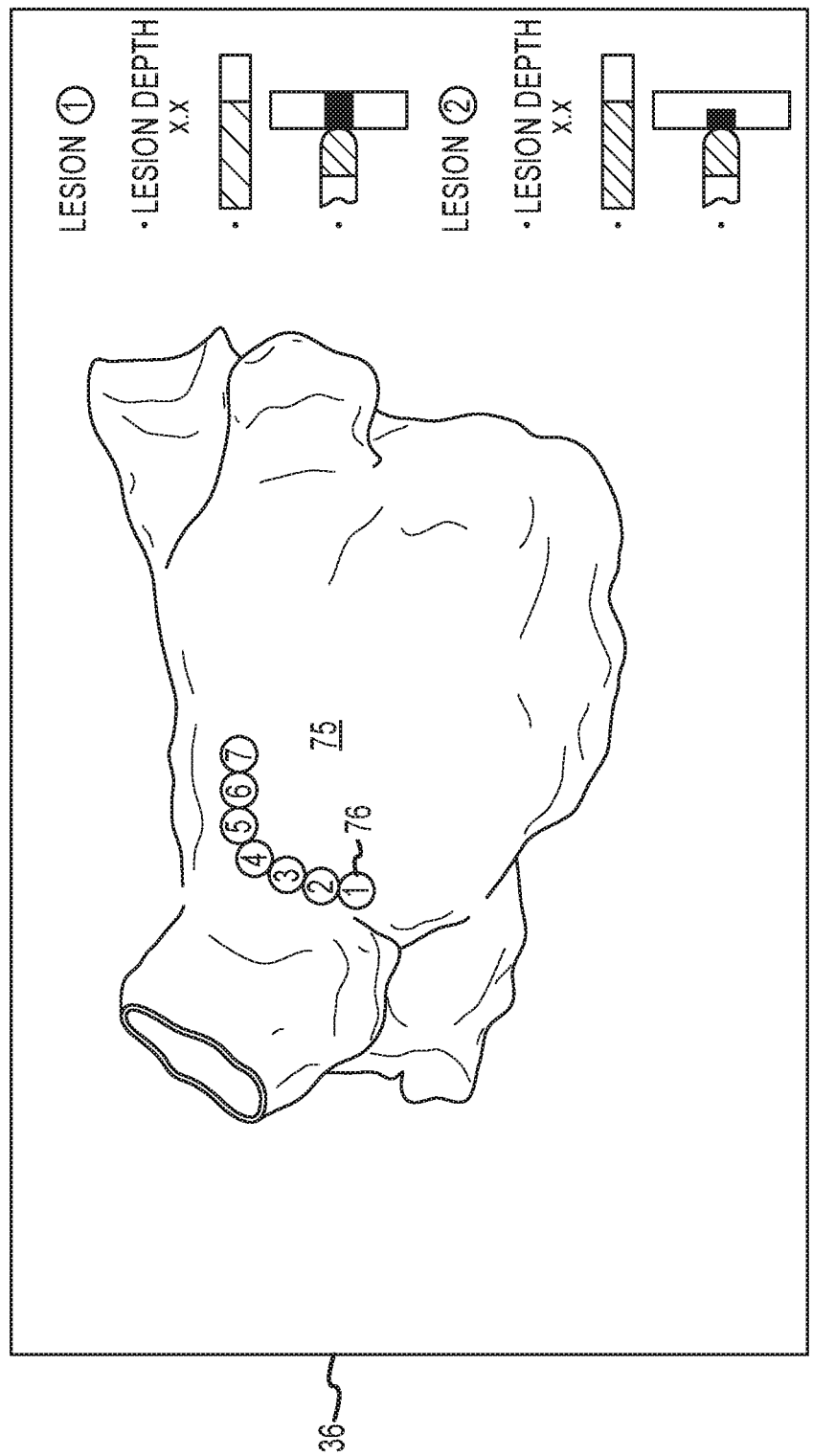
Figure 8N:
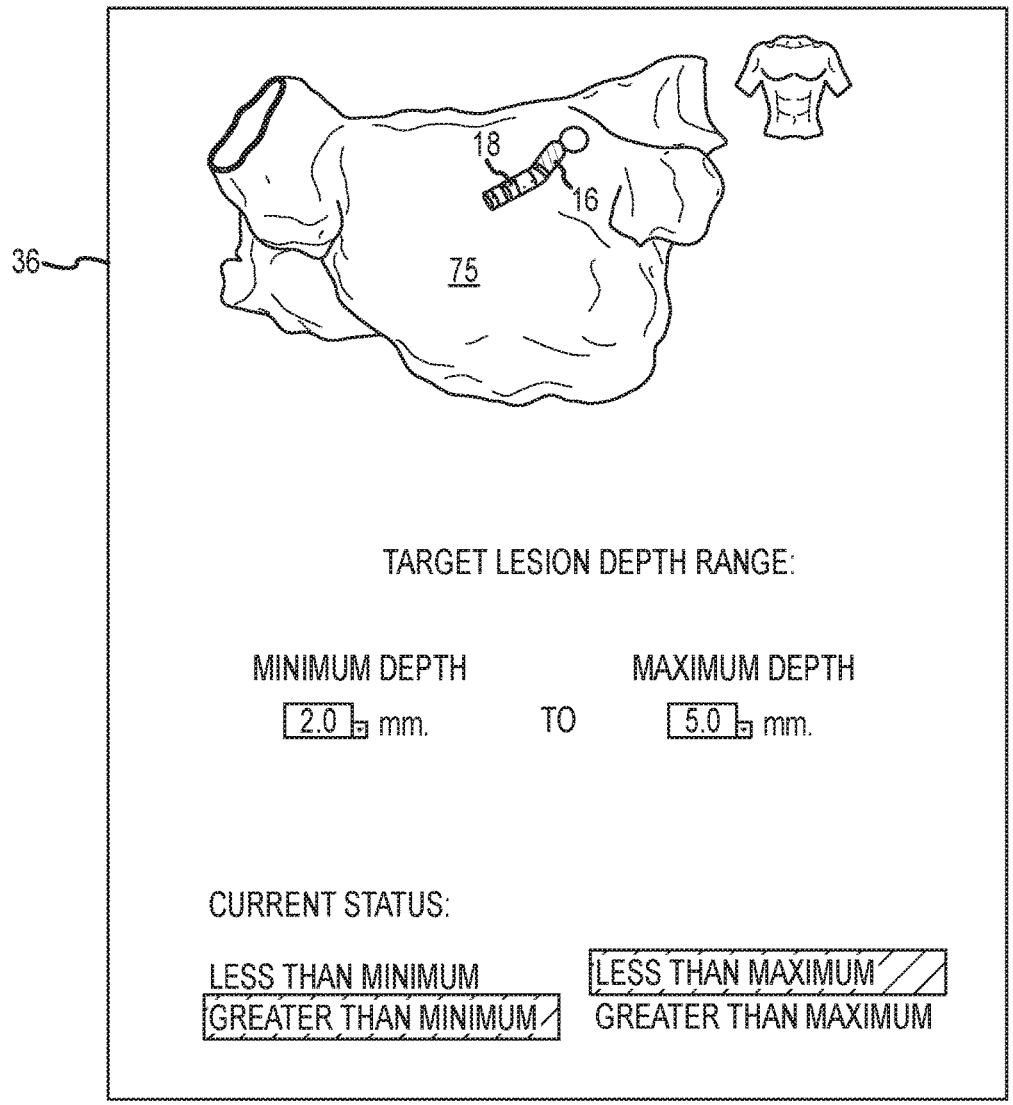

In yet another exemplary embodiment illustrated, for example, in FIG. 8m, the ECU 34 may be configured to superimpose one or more markers 76 corresponding to a lesion created by the application of RF energy using system 10. The markers 76 may be superimposed on the image/model 75 for the corresponding location on the anatomical structure. Each marker may be numbered or otherwise identified (e.g., different shapes, sizes, etc.) so as to provide a unique marker for each lesion (i.e., to differentiate between different lesions). The system 10 may be configured to store information regarding a particular lesion (e.g., calculated predicted lesion depth, transmurality of the lesion, etc.) along with the number or other identifier for the lesion in a temporary or permanent memory or storage medium that is either part of, or accessible by, the ECU 34, such as, for example, the memory 73. The system 10 may be further configured to correlate each lesion with its location on the anatomical structure at which the measurements corresponding to the calculated predicted lesion depth were taken. One exemplary method by which this may be done is described in U.S. Pat. No. 7,263,397 entitled "Method and Apparatus for Catheter Navigation and Location and Mapping in the Heart," which was incorporated by reference and described above.

The ECU 34 may be further configured to retrieve one or more of the numbers or other identifiers for the lesions, along with one or more items of information regarding the corresponding lesion (e.g., calculated predicted lesion depth, transmurality of the lesion, etc.). The ECU may be further configured to display on the display 36 one or more of the numbers or other identifiers for the lesions, along with one or more items of information regarding the corresponding lesion. Although FIG. 8m generally illustrates a display including at least two of the numbers or other identifiers for the lesions, along with information regarding the lesion, fewer or more lesions may be displayed. In addition, information regarding multiple lesions may be displayed sequentially, simultaneously, and/or in any other format or layout in other embodiments of the invention. The system 10 may be configured to allow for the display of additional information regarding a lesion in other embodiments of the invention. The system 10 may be configured to allow for a user of the system 10 to select one or more particular lesions for which the user desires information to be displayed. Accordingly, the system 10 may be configured to retrieve any information regarding one or more previously created lesions that has been stored in the temporary or permanent memory or storage medium that is either part of, or accessible by, the ECU 34, such as, for example, the memory 73. The system may be further configured to display the information on display 36. Accordingly, information regarding any previously created lesions may be recalled by the system 10 and displayed to the user at a later time.

In another exemplary embodiment illustrated, for example, in FIGS. 8n-9b, in addition to or instead of displaying the calculated predicted depth on the display 36 in numeric form, the calculated predicted depth may be compared to a predetermined target and then an indication may be provided based on whether the calculated predicted depth meets, exceeds, or falls short of the target. More particularly, with reference to FIG. 9a, in one exemplary embodiment, the system 10 may be programmed with a target that corresponds to a maximum lesion depth. This target may be preprogrammed into the system 10 during the manufacturing process, or may be set by the user. Additionally, the target may be fixed or, alternatively, may be adjustable by the user of the system 10. In an instance wherein the user can either program the target into the system 10 and/or adjust the target, the system 10 may include a user interface 80 (shown in FIG. 1), such as, for example, a touch screen, a keyboard, a keypad, a slider control, or some other user-controllable input device that is electrically connected to the ECU 34 to allow the user to adjust the target.

Once the target is set (Step 120), as each predicted depth calculation is made, it is compared to the target (Step 122). Depending on whether the calculated predicted depth is above, at, or below the target, an indication may be provided to the user (Step 118). For example, if the calculated depth is at or above the target, an indication in the form of a visual indicator such as a light or a message may be displayed on, for example, the display 36, and/or an audio alert in the form of a buzzer, alarm, audible message, or other similar indicator may be activated. If the calculated depth is below the target, no indication may be provided, or an indication in the form of a visual indicator different from that indicating the target has been met or exceeded, such as a light or a message, may be displayed on, for example, the display 36, and/or an audio alert in the form of a buzzer or other similar indicator may be activated.

Figure 9A:
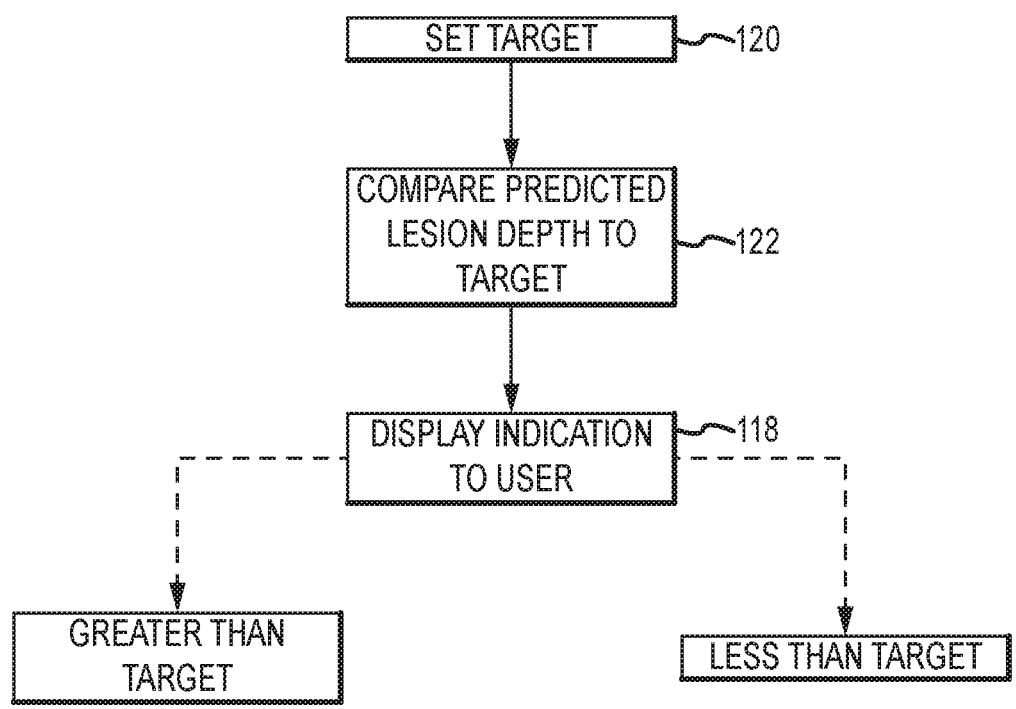
FIGS. 9a-9b are flow charts illustrative of exemplary embodiments of methodologies for using predicted lesion depths calculated using the methodology of FIG. 6.
Figure 9B:
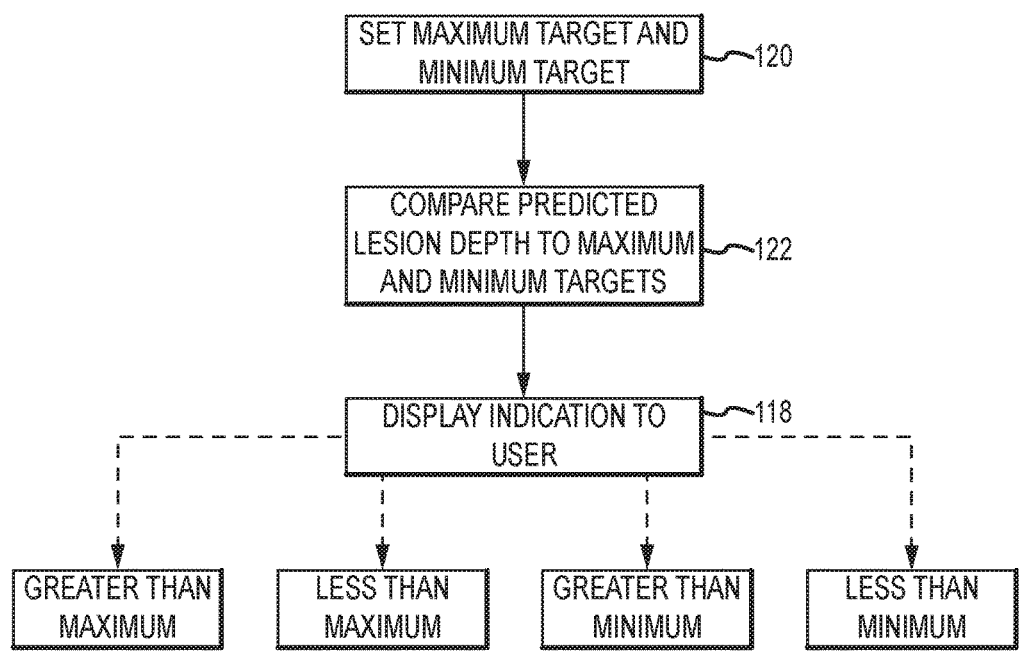

In another exemplary embodiment illustrated, for example, in FIGS. 8e and 9b, the system 10 may be configured to have more than one target. For example, the system 10 may have a first target that, as described above, corresponds to a maximum lesion depth, and a second target that corresponds to a minimum lesion depth. As described above, these targets may be preprogrammed into the system during manufacturing, or may be set by the user. Similarly, the targets may be adjustable or fixed. In the instance where the user may set or adjust the targets, the description above relating to a user interface applies here with equal force. Additionally, the respective targets may be displayed on the display 36, or alternatively, may be stored in the system 10 and not displayed.

As described above, as each predicted depth calculation is made, it is compared to both targets (Step 122). Depending on whether the calculated predicted depth is above, at, or below the two targets, one or more an indications may be provided to the user (e.g., lights, visual or audio messages, audio alerts, etc.) (Step 118). For example, in one exemplary embodiment, the system 10 includes two indicators corresponding to each target—"less than maximum," "greater than maximum," "less than minimum," and "greater than minimum." Accordingly, as a predicted depth calculation is made, it is compared to each target. In one embodiment, if the calculation falls below both the minimum and maximum targets, the display will provide the indicators "less than minimum" and "less than maximum." If the calculation falls between the two targets, the display will provide the indicators "greater than minimum" and "less than maximum." Further, if the calculation is greater than the maximum, the display will provide the indicators "greater than minimum"

and "greater than maximum." It will be appreciated that rather than the specific indicators described here, other indicators, such as those described above with respect to the embodiment having a single target, may be used, and therefore, remain within the spirit and scope of the present disclosure.

Regardless of how the calculated predicted depth is processed and/or displayed, once the predicted depth has been calculated and evaluated for a set of samples taken at a predetermined point in time, in an exemplary embodiment, the system 10 is configured to repeat the above-described process for a set of subsequent samples taken at a subsequent point in time in accordance with a predetermined rate of calculating the predicted depth (i.e., for each set of samples taken for R, $\phi$, and Avg.P; after a predetermined number of sets of samples are taken; after predetermined amount of time has elapsed, etc.). The process may be continuously repeated at a given rate until, for example, the lesion has been acceptably formed (i.e., the lesion has reached a certain depth), or the formation process has been otherwise stopped.

As described above, rather than predicting the depth of a lesion, the formation of a lesion may be assessed by determining the likelihood that the lesion has reached a predetermined depth, or in other words, predicting whether a lesion has reached or attained a predetermined depth. The predetermined depth may be, for example but is not limited to, a depth corresponding to the thickness of the target tissue. Based on the experimentation and analysis described above, and a binary logistic regression analysis, in particular, it was generally determined that for the particular equipment and arrangement of the system used in the experimentation, and for a particular target depth (which, in this example, is 2 mm), the resistance (R) and reactance (X) components of the complex impedance between the electrode 16 and the tissue 12, the duration of the lesion formation process, or change in time from the start of the lesion formation process to the point in time the depth is assessed, and the power applied to the tissue 12 during the lesion formation process were significant factors to be considered in the algorithm. More specifically, it was determined that the ECI of the tissue 12 derived, for example, from the resistance and reactance components of the complex impedance (R and X), the duration of the lesion formation process (dt), and the average power (Avg.P) applied to the tissue during the lesion formation process were the most significant factors to be considered.

The ECI of the tissue 12 may be calculated or derived as described in U.S. patent application Ser. No. 12/253,637 filed Oct. 17, 2008 and entitled "System and Method for Assessing Coupling Between an Electrode and Tissue," which is incorporated herein by reference in its entirety. Generally speaking, however, in an exemplary embodiment provided for illustrative purposes only, the ECI may be based on mean values of the resistance (R) and reactance (X), and more specifically, the equation: ECI=a*Rmean+b*Xmean+c. In one exemplary embodiment, this equation was further resolved into the following equation: ECI=Rmean−5.1Xmean. Accordingly, using this equation, for example, the ECU 34 may calculate the ECI of the tissue 12.

It was further determined that various other factors would possibly have an impact on the accuracy of the algorithm. These factors include, for example and without limitation, parameters or characteristics of the equipment and/or arrangement of the system 10 (such as, for example, the type of catheter and ablation generator being used, the irrigation flow rate, etc.), the target depth being assessed and to which the algorithm corresponds, and the like. Accordingly, it was determined that the most computationally efficient index would be based on the "electrical" factors above (i.e., Avg.P, dt, ECI), as well as certain predetermined constants and coefficients to account for design parameters or characteristics of the devices/equipment used in the procedure and for the target depth. More specifically, it was determined that the best equation or algorithm was the equation (7):

$$\text{Index (2 mm)}=a+b_1\text{Avg.}P+b_2(\ln dt)+b_3(dECI) \tag{7}$$

In this equation, the constant a and the coefficients $b_1$-$b_3$ are predetermined values that are intended to account for the various factors described above. The constant and coefficients can be determined in a number of ways, such as, for example, controlled experimentation or using analyses, such as, for example, a regression analysis. Once the constant and coefficients are determined, they may be stored or programmed into the ECU 34, or a memory storage device 73 (best shown in FIG. 1) associated therewith or accessible thereby. Alternatively, the catheter 18 may itself include a memory such as an EEPROM that stores numerical values for the coefficients and constant corresponding to that particular type of catheter and/or other equipment of the system 10, or stores a memory address for accessing the numerical values in another memory location. The ECU 34 may retrieve these values or addresses directly or indirectly and factor them into the calculation accordingly. It should be noted that in any of the aforementioned arrangements or configurations, the coefficient/constant values may also be correlated or associated in the memory with the particular target depth to which they correspond. For example, if the coefficients/constant have been determined for a depth of 2 mm, then they may be stored such that the coefficient/constant values are associated with a depth of 2 mm. Accordingly, as will be described in greater detail below, algorithms and/or coefficient and constant values for different depths may be stored and accessed by the ECU 34.

It should be understood that while the coefficients and constant of the particular equation above may vary depending on, among other things, the specific catheter used, the ablation generator employed, the target depth, the irrigation flow rate, potentially the patient, other equipment in the system, the species being treated, and the like, the value calculated using the particular equation above will always be responsive to components of the complex impedance and the RF power applied to the tissue in order to arrive at an optimal assessment of the predicted lesion depth in the tissue 12 during an ablation procedure performed thereon. It should be further noted that the constant and coefficients are determined and programmed as part of the manufacturing and/or setup process of the system 10, and thus, are not determined during the use of the system 10 in accordance with its intended purpose.

By way of example and illustration, employing the experimental testing and regression analysis described above, and using a RF ablation catheter available from St. Jude Medical, Inc. under the name "CoolPath" and a 485 kHz RF ablation generator, the best algorithm for determining the likelihood of a lesion reaching a target depth of 2 mm for a system employing those particular components was determined to be the following equation (8):

$$\text{Index (2 mm)}=-12.2+0.23\text{Avg.}P+1.94(\ln dt)+0.11(dECI) \tag{8}$$

This was determined by data collected for lesions created in vitro in non-perfused bovine cardiac tissue. Data was collected and a regression model was performed to come to equation (8), and the values of the constant and coefficients thereof. The solution to the equation represents the natural log of the odds that a lesion attained or reached a target depth (i.e., 2 mm for this particular equation). As will be described in greater detail below, in an exemplary embodiment, once the value or index is calculated, it is compared to a predetermined threshold. The user of the system 10 may then be provided with an indication as to the likelihood that the lesion has attained the target depth depending on whether the calculated value or "index" exceeds or is below the predetermined threshold. The threshold may be determined by testing or other analyses.

It should be noted that although equations (7) and (8) and the corresponding description above and below focus on the use of ECI, it should be understood that the value or index could also be based (in addition or alternatively) on values associated with the rectangular coordinates of the complex impedance, the polar coordinates of impedance magnitude (|Z|) and phase angle ($\phi$), or indeed any combination of the foregoing components of the complex impedance, power, and derivatives or functional equivalents thereof. For example, in addition to the values of the constant and coefficients of the index equation above changing due to factors such as the type of catheter, the type of ablation generator, the target depth, and other characteristics or parameters, these factors may also determine or impact which component or components of the complex impedance and/or aspects of the power are the most significant, and therefore, best for use in the equation for calculating the value or index for certain equipment and/or target depths.

Further, while the equations set forth above are based on two components of the complex impedance (ECI=Rmean−5.1Xmean), in other exemplary embodiments the equation may be based on a single component, or more than two components of the complex impedance, and may include more or less terms than equations (7) and (8). Additionally, while the equations (7) and (8) include a term based on the magnitude of the average power applied to the tissue 12, in other embodiments one or more other aspects of the RF power, such as, for example, the natural log of the RF power, the instantaneous power, and the like may be used in addition to or instead of the average power magnitude. Therefore, it will be appreciated that the form of the equation to be used for calculating the value or index may be highly dependent on the type or types of the equipment used in the ablation procedure and the target depth. Therefore, the present invention is not meant to be limited to the use of any particular complex impedance components, particular aspects of the RF power, or number of components. Rather, equations used to calculate the value or index that are based on one or more values or one or more components of one or more complex impedances, and one or more values of aspects of the power applied to the tissue 12 remain within the spirit and scope of the present invention.

Once the particular complex impedance components to be used in calculating the value for a particular catheter or arrangement of the system 10 and for a particular depth are determined and the form of the equation is resolved, the components of the complex impedance (or an indication corresponding thereto), the equation to be used, and/or the specific terms of the equation (including, if appropriate, the constant(s) and/or coefficients for the equation terms) may be stored or programmed into the ECU 34, or a memory/storage device 73 (best shown in FIG. 1) associated therewith or accessible thereby. Alternatively, the catheter 18 or another component in the system 10 may include a memory, such as an EEPROM, that is configured to store the above identified information or a memory address for accessing the information stored in another memory location corresponding to that particular type of catheter and/or other equipment of the system 10. The ECU 34 may retrieve this information or addresses directly or indirectly and use it to calculate the value or index. As will be described below, in an exemplary embodiment, the memory in which the equations are stored may have a number of equations stored therein. For example, different equations for different catheters/equipment may be stored in the memory, as well as multiple equations for the same equipment but corresponding to different depths. Accordingly, depending on the equipment used and/or the target depth being assessed, the ECU 34 may obtain or acquire the correct equation/algorithm.

Figure 10:
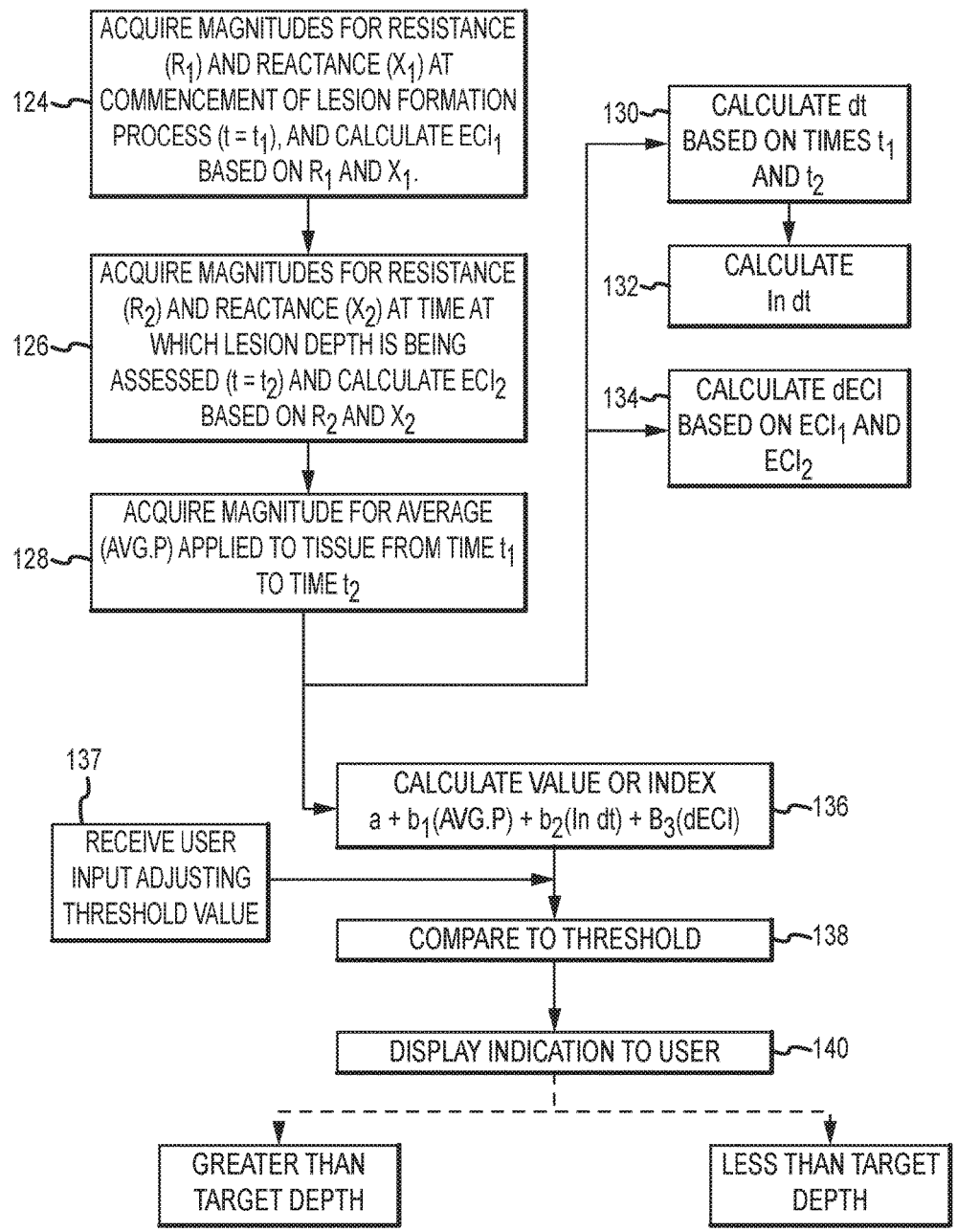
FIG. 10 is a flow chart illustrative of another exemplary embodiment of the methodology illustrated in FIG. 4 shown in greater detail.

With reference to FIG. 10, an exemplary calculation will be described for determining the likelihood that a lesion has reached a predetermined depth will be described. For purposes of clarity, brevity, and illustration, the description below of an exemplary calculation has been limited to an embodiment wherein the value or index is calculated based, in part, on the ECI of the tissue 12, the magnitude of the average power applied to the tissue 12, and the magnitude of duration of the lesion formation process (i.e., using the equation (7) above). It has further been limited to an equation corresponding to a depth of 2 mm. It will be appreciated in view of the above, however, that the present disclosure is not meant to be limited to such an embodiment.

As an initial matter, in addition to being configured to calculate the value or index described above, in an exemplary embodiment, the ECU 34 is also configured to acquire and/or calculate the terms used in the equation for calculating the value (i.e., Avg.P, dt, dECI, etc.). As described above, and as illustrated in FIG. 4, in this embodiment, the ECU 34 is configured to acquire magnitudes for first and second components of the complex impedance (i.e., R and X), the magnitude of power being applied to the tissue 12 during the ablation procedure (and more particularly, the magnitude of the average power applied), and the elapsed time of the lesion formation process. More particularly, with reference to FIG. 10, the ECU 34 is configured to acquire magnitudes for the resistance $R_1$ and reactance $X_1$ between the electrode 16 and the tissue 12 at a point in time $t=t_1$ at which the lesion formation process commenced (i.e., just after initiation of RF power/energy delivery to the tissue 12), and to calculate an ECI ($ECI_1$) based on the magnitudes of $R_1$ and $X_1$ (Step 124). The magnitudes of $R_1$ and $X_1$ may be received from the complex impedance sensor 64, and may stored along with the corresponding time (i.e., $t=t_1$) in a temporary or permanent memory or storage medium that is either part of, or accessible by, the ECU 34, such as, for example, the memory 73.

The ECU 34 is further configured to acquire magnitudes for R and X at a point in time $t=t_2$ at which the depth of a lesion formed or being formed is assessed ($R_2$ and $X_2$), and to calculate an ECI ($ECI_2$) based on the magnitudes of $R_2$ and $X_2$ (Step 126). The ECU 34 is still further configured to acquire the magnitude of the average RF power (Avg.P) applied to the tissue 12 from the start of the lesion formation process (i.e., time $t=t_1$) to when the lesion depth is assessed (i.e., time $t=t_2$) (Step 128). The R and X magnitudes may be received from the complex impedance sensor 64, and the average power magnitude may be received from the ablation generator 26, a reporting system associated therewith, or may be calculated by the ECU 34. Each magnitude may be correlated and/or stored along with the corresponding time (i.e., t=$t_2$) in a memory or storage device, such as that described above, in the manner illustrated, for example, in FIG. 11.

Because the depth of a lesion may be assessed as it is being formed such that the lesion depth may be monitored in real-time, the ECU is further configured to sample the magnitudes of R, X, and Avg.P throughout the formation of the lesion at one or more respective predetermined sampling rates in order to constantly and continuously monitor the formation of the lesion. In an exemplary embodiment, a sampling rate on the order of 100 to 800 times per second may be used, however, the present disclosure is not meant to be limited to such a range of rates but rather sampling rates that are greater or less than 100 to 800 Hz may be used in different embodiments. Accordingly, the ECU 34 is configured to sample the signal received from the complex impedance sensor 64 at a predetermined rate and to store the corresponding R and X values ($R_1$, $R_2$, ..., $R_n$ and $X_1$, $X_2$, ..., $X_n$) derived therefrom in the memory or storage medium described above along with the corresponding times (i.e., $t_1$, $t_2$, ..., $t_n$) at which the samples were taken (See FIG. 11). The ECU 34 is further configured to calculate an ECI for each corresponding R and X values, and to store each ECI in the memory or storage medium as well, Similarly, the ECU 34 is configured to sample the signal received from the ablation generator 26, or an associated reporting system, at a predetermined rate and to store the corresponding average power magnitudes (Avg.$P_1$, Avg.$P_2$, ..., $P_n$) in a memory such as that described above along with the corresponding times (i.e., $t_1$, $t_2$, ..., $t_n$) at which the samples were taken (See FIG. 11). As briefly described above, in an exemplary embodiment, rather than the ablation generator 26 providing the magnitude of the average power applied, the ECU 34 may be configured to receive signals from the ablation generator 26 corresponding to the magnitude of the instantaneous power (P), and the ECU 34 may be configured to make the calculation to determine the average power (Avg.P) based on current and past power magnitudes.

In an exemplary embodiment, after each sample of R, X, and Avg.P is taken, and an ECI based on the R and X samples is calculated, the system 10 is configured to calculate the value or index described above. Alternatively, rather than calculating the value or index after each sample, the ECU 34 may be configured to perform the calculation at some other rate, such as after a certain number of samples have been collected or after a certain amount of time has elapsed. For the purposes of clarity and brevity alone, the description below will be directed to an embodiment wherein the calculation is made after a sample of each of the R, X, and Avg.P is collected at a particular point in time (i.e., time t=$t_2$). It will be appreciated, however that the present disclosure is not meant to be limited to such an embodiment.

Accordingly, after a set of samples of each of R, X, and Avg.P are collected, and an ECI based on the values of R and X is calculated (Steps 124-128), the ECU 34 is configured to perform a number of calculations. For example, and as illustrated in FIG. 10, the ECU 34 is configured to calculate a change in the time, or the elapsed time, represented by the time interval from the point in time that the lesion formation process commenced to the point in time that the current sample was taken (dt) (Step 130), and to calculate the natural log of the magnitude of the change in time (Step 132). The ECU 34 is further configured to calculate a change in ECI (dECI) of the tissue 12 between the ECI of the tissue 12 at the onset of the lesion formation process and the ECI at the point in time at which the lesion depth is being assessed (Step 134).

With respect to the change in time, the ECU 34 is configured to calculate the change in time or the elapsed time represented by the time interval from the point in time that the lesion formation process commenced (i.e., time t=$t_1$) to the point in time that the current samples were taken, and therefore, the point in time that the lesion depth is being assessed. Accordingly, if the value or index is being calculated using the values sampled at time t=$t_2$, the change in time is calculated by subtracting the time $t_1$ from the time $t_2$ to determine the elapsed time of the procedure thus far. Accordingly, the ECU 34 is configured to acquire the times corresponding to $t_1$ and $t_2$ and to perform the calculation to determine the magnitude of the change in time or the amount of elapsed time. Similarly, if the value or index is being calculated at time $t_3$, the change in time is calculated by subtracting the time $t_1$ from the time $t_3$, and so on and so forth. Accordingly, regardless of the point in time of the lesion formation process at which the index is being calculated, the current time value is always processed with the time value $t_1$ to determine the change in time. Once the change in time magnitude is determined, the ECU 34 is configured to calculate the natural log of the change in time magnitude (ln dt).

With respect to the change in ECI (dECI), the ECU 34 is configured to calculate the change in the ECI over the time interval beginning at the point in time the lesion formation process commences (i.e., just after initiation of RF power/energy delivery to the tissue 12) (i.e., time t=$t_1$), to the point in time at which the lesion depth is assessed. Accordingly, if the calculation is being made for the samples of R, X, and Avg.P taken at time t=$t_2$, dECI is calculated by subtracting $ECI_2$ from $ECI_1$. Accordingly, the ECU 34 is configured to calculate or acquire ECI magnitudes $ECI_1$ and $ECI_2$ and to perform the calculation to determine the change in ECI. Similarly, if the value or index is being calculated at time $t_3$, the change in ECI is calculated by subtracting the $ECI_3$ from the $ECI_1$, and so on and so forth. Accordingly, regardless of the point in time of the lesion formation process at which the value or index is being calculated, the current ECI magnitude is always processed with the $ECI_1$ to determine the change in ECI.

Once all of the terms above are calculated, the ECU 34 is configured and able to calculate the value or index in order to determine the likelihood that the lesion has reached or achieved a predetermined depth (i.e., 2 mm in this exemplary embodiment) or to predict whether the lesion has reached the predetermined depth (Step 136). Accordingly, the ECU 34 is configured to acquire the correct or appropriate values for the constant a and the coefficients $b_1$-$b_3$, and, using the appropriate equation, to process these values with the terms described above to come to a value or index. Accordingly, the computer program stored or accessible by the ECU 34 includes code for carrying out the execution of the equation. Once the value or index is calculated, it may be used in a number of ways.

In an exemplary embodiment, such as that illustrated in FIG. 10, the system 10, and the ECU 34, in particular, is programmed with, or configured to access, a threshold value to which the index or value calculated by the equation is compared to determine or predict whether the lesion has achieved a certain depth. The threshold is determined by experimentation and/or analysis performed prior to use of the system 10 (i.e., as part of the manufacturing or set up process, for example), and may be impacted by the factors described above, such as, for example, the type of catheter, the type of ablation generator, and other characteristics relating, for example, the equipment of the system 10. In such an embodiment, the calculated index or value is compared to the threshold value (Step 138) and, based on that comparison, the ECU 34 is configured to generate a signal representative of a prediction that the lesion depth has exceeded or is greater than a predetermined depth (e.g., the index or value meets or exceeds the threshold), or that is predicted that the lesion depth is less than the predetermined depth (e.g., the index or value does not meet and is below the threshold). The ECU 34 may be further configured to then control a display device, such as, for example, the display 36, to display the prediction represented by the signal generated by the ECU 34 (Step 140).

In an exemplary embodiment, the threshold is set prior to the system 10 being used and is not adjustable. Alternatively, in another exemplary embodiment, the threshold may be adjustable by the user to change, for example, the sensitivity of the system. In the latter embodiment, the system 10 may include a user interface, such as for example, user input device 80, which may comprise a touch screen, a keyboard, a keypad, a slider control, or some other user-controllable input device that is electrically connected to the ECU 34, to allow the user to adjust the threshold value (Step 137).

More particularly, the system 10 may be programmed with multiple threshold values corresponding to the same target depth, but that represent varying levels of sensitivity. These threshold values may be stored in a memory associated with, or accessible by, the ECU 34 (e.g., the sensitivity levels and corresponding threshold values may be stored in a look-up table, for example). In an exemplary embodiment provided for illustrative purposes only, the system 10 may have three threshold values that correspond to the target depth—one for high sensitivity, one for medium sensitivity, and one for low sensitivity. In one exemplary embodiment, the threshold for the medium sensitivity may be the default threshold that is used unless the user adjusts the sensitivity of the system. In another exemplary embodiment, the user may have to set the desired sensitivity when the system 10 is initialized. In another embodiment, rather than adjusting the sensitivity level of the system, and therefore, the threshold, the value of the threshold may be adjustable by the user inputting a value for the threshold, or otherwise adjusting the threshold value (as opposed to indirectly adjusting the threshold by adjusting the sensitivity). In any case, the user has a measure of control over the sensitivity of the system 10.

Figure 12:
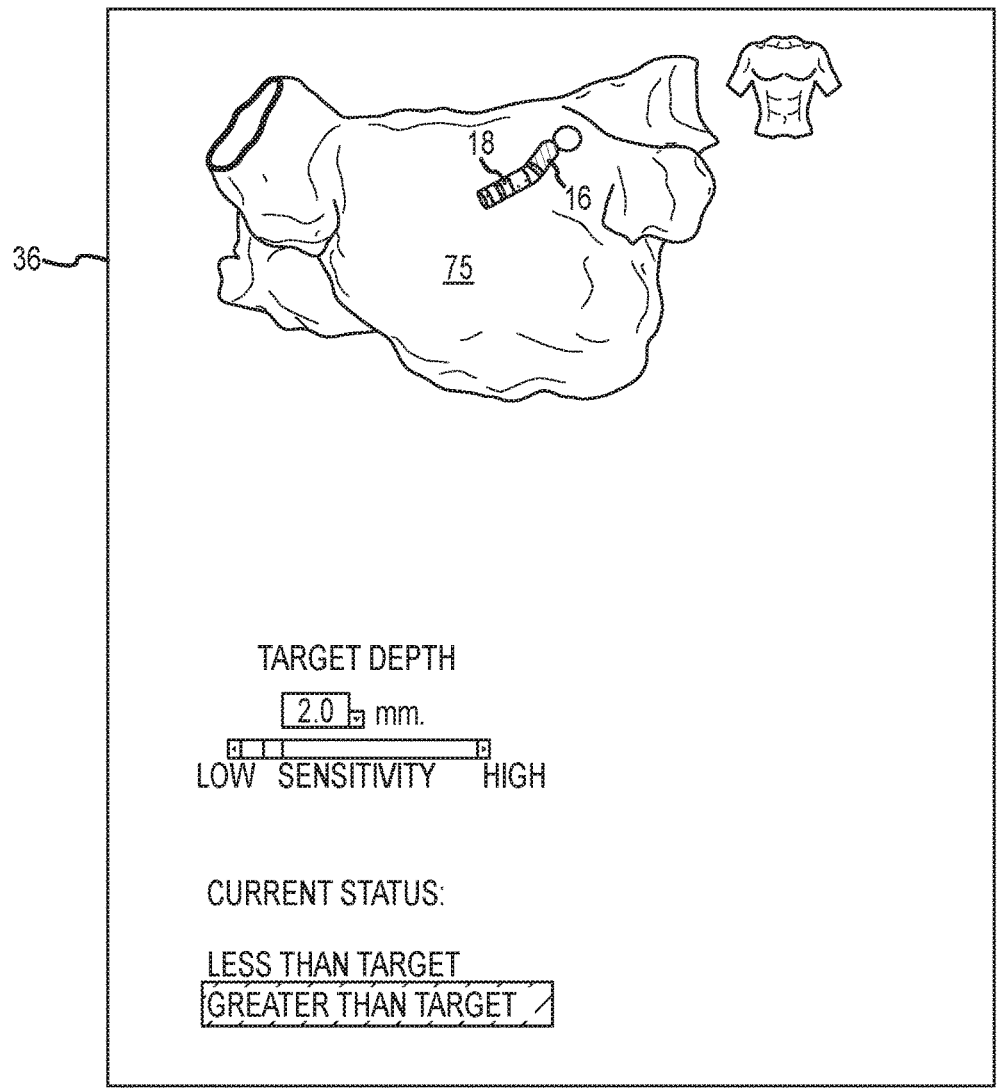
FIGS. 12 and 13 are exemplary embodiments of screen displays illustrating possible formats for presenting a prediction or likelihood of whether a lesion has attained a predetermined depth calculated using the methodology of FIG. 10.

In an exemplary embodiment, in addition to, or instead of, the threshold being adjustable, the target depth may be adjusted. For example, while the description above has generally been with respect to a target depth of 2 mm, in an exemplary embodiment of the system 10, the user is able to adjust the target depth using, for example, the user input device 80. In such an embodiment, the system 10, and the ECU 34, in particular, is configured to have a plurality of equations or algorithms stored therein or in a memory accessible thereby, that correspond to different depths (e.g., in an exemplary embodiment, the depths and corresponding algorithms may be stored in a look-up table that may be accessed by the ECU 34). Alternatively, the catheter 18 may be configured to store the various equations or algorithms in the same manner described above. Accordingly, the user may input the desired target depth into the system 10, and the ECU 34 is configured to obtain the corresponding algorithm and to perform the calculations and comparisons accordingly. FIG. 12 illustrates and exemplary embodiment of a display 36 that includes a means by which the target depth may be adjusted. Accordingly, the system 10 is not limited to assessing the odds of a lesion reaching any particular depth, but rather may have the flexibility to assess more than one depth.

In an exemplary embodiment, once the value or index is calculated and it is compared to the threshold value, the system 10 may be configured to cause an appropriate indicator to be given to the user of the system 10 relating to the prediction of whether the target depth has been met. The indicator generated by the ECU 34 may take many forms. For example, with reference to FIG. 12, the indicator may be displayed on the display monitor 36. Such a displayed indicator may include, for exemplary purposes only, displaying an alert or warning message on the monitor 36. In the illustrated embodiment, an indicator may be provided as to whether the lesion depth is "less than" the target depth, or "greater than" the target depth. The indicator may also be in the form of a lesion marker on a map of the target tissue. The lesion marker may vary in color and/or size depending on the nature of the lesion predicted, for example, a deep lesion may be red, a shallow lesion may be green, and an intermediate lesion may be yellow. The system may allow the user to set the ranges for particular colors. In another embodiment, the system may consider the tissue depth at a particular target location and use a particular color marker color to indicate when the lesion is at a depth that is considered transmural for the target location. In other exemplary embodiments, the indicator may take the form of an audible alert, a visible indication on the catheter handle or another device of the system 10, haptic feedback, a binary type output (e.g., "light on"/"light off"), a gas gauge type of output, or any other indicators described above with respect to FIGS. 8*a*-8*f*, or as known in the art. Based on the indicator provided to the user, the user may take corrective measures, such as, for example and without limitation, moving the electrode 16 away from the tissue or toward a new tissue section, reducing the RF power being applied to tissue, and/or other the like measures.

Figure 13:
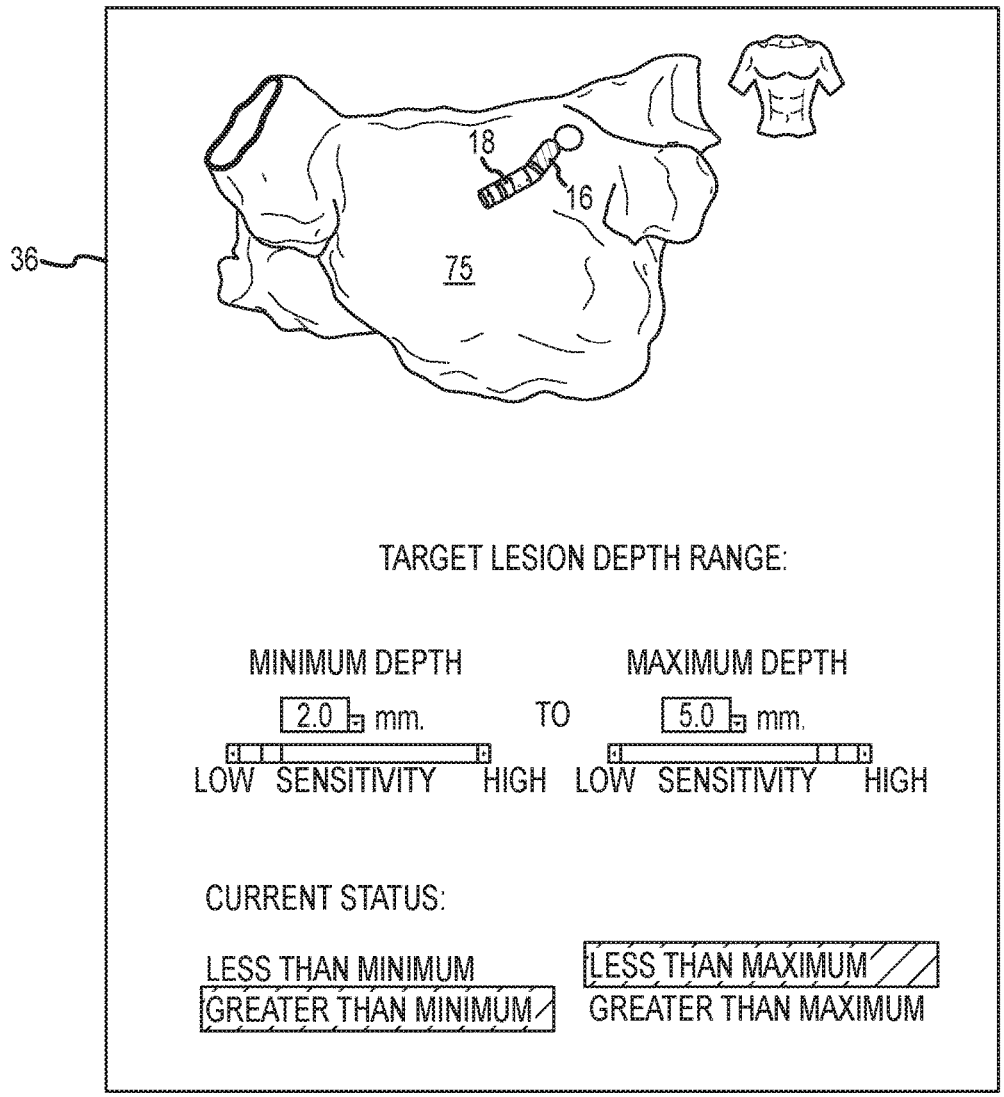

In an exemplary embodiment, rather than assessing the depth of the lesion with respect to a single target depth, the system 10, and the ECU 34, in particular, is configured to assess the depth of the lesion with respect to multiple target depths. For example, a user may want to form a lesion in the tissue 12 that exceeds a minimum depth, but that is less than a maximum depth. A minimum depth may be set to maximize the efficacy of the ablation procedure, while the maximum depth may be set to maximize the safety of the ablation procedure. Accordingly, in such an embodiment, the system 10 is configured to access or obtain the algorithms (which are created or determined in the manner described above) corresponding to the minimum and maximum depths. In the same manner described above wherein a single target depth is assessed, the ECU 34 is further configured to calculate a value or index for each algorithm simultaneously. The resulting values or indices are then compared to the respective thresholds, and, as illustrated in FIG. 13, corresponding indicators are provided to the user for each target depth in the same manner described above. It will be appreciated that the algorithms may include the same or different terms (i.e., the algorithms may be derived from the same or different electrical characteristics or factors and/or have the same or different number of terms), and may have the same or different values for the constants and coefficients (i.e., the same or different values and/or number of constants and coefficients).

As with the single-target embodiment, in an exemplary embodiment, the sensitivity of the system may be adjusted in the same manner described above for each target depth.

Additionally, each target depth may be adjusted in the same manner described above. Accordingly, the system 10 is not limited to assessing the depth of a lesion with respect to a single target depth, but rather may be used to assess multiple depths or ranges of depths.

Whether one or more target depths are being assessed, once the corresponding value(s) have been calculated and processed for a set of samples taken at a predetermined point in time, the process repeats itself for a set of subsequent samples taken at a subsequent point in time in accordance with a predetermined rate of performing the calculation (i.e., for each set of samples taken for R, X, and Avg.P; after a predetermined number of samples are taken; after predetermined amount of time has elapsed, etc.). The process may be continuously repeated at a given rate until, for example, the lesion has been acceptably formed, or the formation process has been otherwise stopped.

As described above, rather than assessing the formation of a lesion by calculating a predicted lesion depth in the tissue 12 resulting from an ablation procedure being performed thereon, or by predicting whether the lesion has attained a predetermined depth, in another exemplary embodiment, the temperature of the tissue as a result of an ablation procedure may be predicted and then used, for example, to assess the depth of the lesion.

Using the experimentation and analysis described above, it was generally determined that for predicting the temperature of the tissue 12 a predetermined depth below the surface (which, in this example, was 3 mm) using the particular equipment and arrangement of the system 10 used in the experimentation and analysis, the reactance (X), the resistance (R), the impedance (Z), and the phase angle ($\phi$) components of the complex impedance between the electrode 16 and the tissue 12, the instantaneous power applied to the tissue 12 (P) at the point in time for which the calculation is made, the duration of the lesion formation process (dt), and the temperature of the tip of the catheter (T) were significant factors to be considered in the algorithm. More specifically, it was determined that the reactance (X), resistance (R), power (P), catheter temperature (T), and impedance (Z) at the time of the calculation, the product of the power (P) and the duration (dt) of the lesion formation process, the pre-ablation change in the phase angle $\phi$ between when the electrode 16 contacts the tissue 12 and prior to the electrode 16 contacting the tissue (d$\phi$) (i.e., when the electrode 16 is in the chamber but not in contact with the tissue, for example), the natural log of the duration (dt), and the natural log of the instantaneous power (P) were the most significant factors to be considered.

As with the depth prediction algorithm described above, it was further determined that various other factors would possibly have an impact on the accuracy of the temperature prediction algorithm. These factors include, for example and without limitation, certain parameters and/or characteristics of the equipment and/or arrangement of the system 10 (such as, for example, the type of catheter and ablation generator being used, the irrigation flow rate, etc.), as well as the depth below the surface (e.g., endocardial surface) of the tissue 12 for which the temperature is being predicted. Accordingly, it was determined that for the equipment used in the testing and for a depth of three millimeters (3 mm) below the tissue surface (which is provided for exemplary purposes only) the most computationally efficient algorithm would be based on the factors above (e.g., X, R, P, T, Z, d$\phi$, dt, etc.), as well as certain predetermined coefficients and constants to account for design parameters or characteristics of the devices/equipment used in the ablation procedure, for example.

More specifically, it was determined that the best equation or algorithm was the equation (9):

$$\text{Predicted Temperature} = a + b_1 X + b_2 R + b_3 P + b_4 T + b_5 Z + b_6(P^*(dt)) + b_7(d\phi) + b_8(\ln dt) + b_9(\ln P) \quad (9)$$

In this equation, the constant a and the coefficients $b_1$-$b_9$ are predetermined values that are intended to account for the various factors associated with, for example, the equipment used in the ablation procedure (i.e., type of catheter and/or ablation generator, irrigation flow rate, etc.). The constant and coefficients, which may be positive or negative values depending on the circumstances, can be determined in a number of ways, such as, for example, controlled experimentation or using analyses, such as, for example, a regression analysis. Once the constant and coefficients are determined, they may be stored or programmed into the ECU 34, or a memory/storage device 73 (best shown in FIG. 1) associated therewith or accessible thereby. Alternatively, the catheter 18 may itself include a memory such as an EEPROM that stores numerical values for the coefficients/constant corresponding to that particular type of catheter and/or other equipment of the system 10, or stores a memory address for accessing the numerical values in another memory location. The ECU 34 may retrieve these values or addresses directly or indirectly and factor them into the calculation accordingly.

It should be understood that while the coefficients and constant of the particular equation above may vary depending on, among other things, the specific catheter used, the ablation generator employed, the irrigation flow rate, potentially the patient, other equipment in the system, the species being treated, the depth for which the temperature is being predicted, and the like, the value calculated using the particular equation above will always be responsive to components of the complex impedance and the RF power applied to the tissue (e.g., instantaneous power) in order to arrive at an optimal assessment of the predicted temperature of the tissue 12 a predetermined depth below the surface thereof. It should be further noted that the constant and coefficients are determined and programmed as part of the manufacturing and/or setup process of the system 10, and thus, are not determined during the use of the system 10 in accordance with its intended purpose.

By way of example and illustration, employing the experimental testing and regression analysis described above, and using a RF ablation catheter available from St. Jude Medical, Inc. under the name "CoolPath" and a 485 kHz RF ablation generator, the best prediction of the temperature of the tissue three millimeters (3 mm) below the surface of the endocardial surface of the tissue 12 for a system employing those particular components was determined to be the following equation (10):

$$\text{Predicted Temperature} = -557 - 2.44X - 1.37R - 6.88P + 3.05T + 3.29Z + 0.0377(P^*(dt)) + 21.1(d\phi) - 14.1(\ln dt) + 167(\ln P) \quad (10)$$

As with the lesion depth prediction algorithm described above, this was determined by bench and/or animal testing that included testing on bovine myocardium. Data was collected and a regression model was performed to come to equation (10), and the values of the constant and coefficients thereof.

As set forth in equations (9) and (10), the temperature of the tip of the catheter 18 (T) and the pre-ablation phase angle both prior to and following the electrode 16 contacting the tissue 12 are evaluated in predicting the temperature of the tissue. Accordingly, the system 10 must include components to both sense the temperature of the tip of the catheter 18, and sense contact, or lack thereof, between the catheter 18 and the tissue 12.

With respect to the temperature of the tip of the catheter 18 (T), in an exemplary embodiment the system 10 includes a temperature-sensing electrode or temperature sensor disposed at the tip of the catheter 18. In one exemplary embodiment, the temperature sensor comprises a thermocouple disposed at the distal end 50 of the catheter and configured to generate an electrical signal representative of the temperature sensed at the tip of the catheter 18. The temperature-sensing electrode or temperature sensor is further configured to communicate the generated signal to the ECU 34 and/or the ablation generator 26. In the latter instance, the ablation generator 26 would be configured to report the temperature to the ECU 34. Accordingly, the ECU 34 and/or ablation generator 26 is electrically connected to the temperature-sensing electrode or temperature sensor (i.e., either by wire(s) or wirelessly) and is configured to receive the electrical signal therefrom.

With respect to the sensing of contact between the catheter 18 and the tissue 12, any number of different contact sensing techniques may be used. For example, using a real-time image, such as a fluoroscopic image, for example, a physician may be able to visualize when the catheter 18 contacts the tissue 12. In another example, a real-time image may be used in conjunction with a physician's tactile sensing to determine contact has been made. In either instance, when the physician believes contact has been made, he may trigger the measurement of the phase angle between the electrode 16 and the tissue 12 by inputting a command into a user interface, such as, for example, the user interface 80 described above. Accordingly, the user input device 80 is configured to generate signal in response to an input by the user.

In another exemplary embodiment, the catheter 18 may have a sensing element (not shown) disposed at or near the tip thereof (i.e., at or near the distal end 50 of the catheter 18) and electrically connected to, for example, the ECU 34. The sensing element, which may comprise an electrode or a sensor, for example, is configured and operative to generate a signal indicative of contact between the sensing element and the tissue 12. Exemplary methods of contact sensing are described in U.S. patent application Ser. No. 12/347,216, filed Dec. 31, 2008 and entitled "Multiple Shell Construction to Emulate Chamber Contraction with a Mapping System," incorporated herein by reference above. In one exemplary embodiment, the sensing element may take the form of any one or more of a variety of electrical-based, electro-mechanical-based, force-based, optically-based, as well as other technology-based approaches known in the art for determining when the sensing element is in contact with the surface of the tissue 12.

An alternate approach for sensing contact is to assess the degree of electrical coupling as expressed, for example, in an electrical coupling index (ECI) between such a sensing element and the surface, as seen by reference to, for example, U.S. patent application Ser. No. 12/253,637, filed May 30, 2008 and entitled "System and Method for Assessing Coupling Between an Electrode and Tissue," which is incorporated herein by reference in its entirety.

In yet another alternate approach, an electrically-measured parameter indicative of contact, such as, for exemplary purposes only, the phase angle of a measured complex impedance, may be used to determine when the sensing element is in contact with tissue 12. One phase angle measurement technique may be as described in U.S. Patent Publication No. 2009/0171345 entitled "System and Method for Measurement of an Impedance Using a Catheter such as an Ablation Catheter," which is incorporated herein by reference in its entirety.

Accordingly, the system 10 may employ one or more of the above-described techniques to sense when the catheter 18 has contacted the tissue 12 in order to make the necessary measurements needed for the temperature prediction algorithm.

It should be noted that although the equations above relating to predicting tissue temperature and the corresponding description above and below focus on the combination of the R, X, Z, and φ components of the complex impedance, it should be understood that, in addition or alternatively, combinations comprising less than all of the complex impedance components, and derivatives or functional equivalents thereof, may be used in predicting tissue temperature. For example, in addition to the values of the constant and coefficients of the index equation above changing due to factors such as the type of catheter, the type of ablation generator, and other characteristics or parameters, these factors may also determine or impact which component or components of the complex impedance and/or aspects of the power are the most significant, and therefore, best for use in the equation for calculating the predicted tissue temperature at a certain depth below the surface of the tissue and using certain equipment. Therefore, the present invention is not meant to be limited to the use of any particular complex impedance components, particular aspects of the RF power, or number of components. Rather, equations used to calculate the predicted tissue temperature that are based on one or more components of one or more complex impedances, and one or more aspects of the power applied to the tissue 12 remain within the spirit and scope of the present invention.

Once the particular complex impedance components to be used in the algorithm for a particular catheter or arrangement of the system 10 are determined and the form of the algorithm/equation is resolved, the components of the complex impedance (or an indication corresponding thereto), the equation to be used, and/or the specific terms of the equation (including, if appropriate, the constant(s) and/or coefficients for the equation terms) may be stored or programmed into the ECU 34, or a memory/storage device 73 (best shown in FIG. 1) associated therewith or accessible thereby. Alternatively, as described above, the catheter 18 or another component in the system 10 may include a memory, such as an EEPROM, that is configured to store the above identified information or a memory address for accessing the information stored in another memory location corresponding to that particular type of catheter and/or other equipment of the system 10. The ECU 34 may retrieve this information or addresses directly or indirectly and use it to calculate the predicted tissue temperature.

Figure 14:
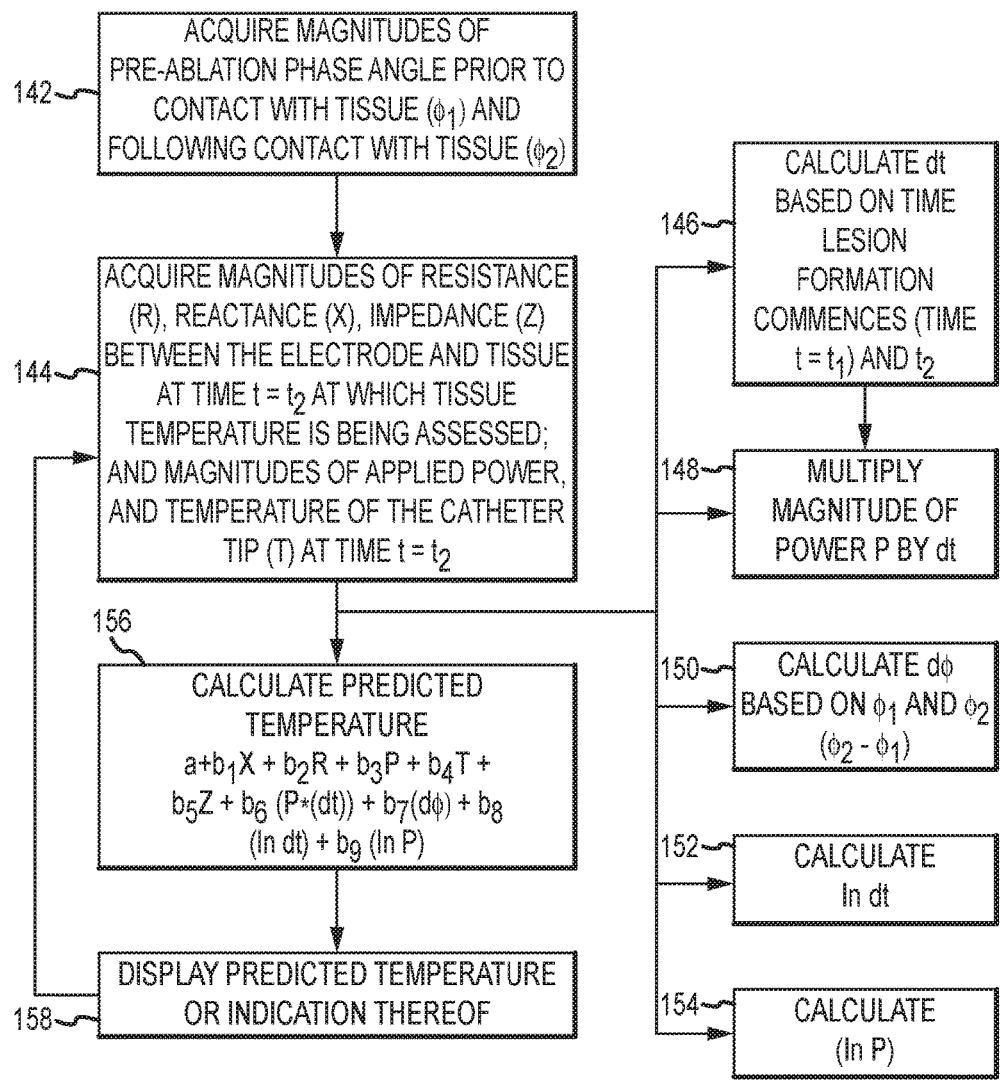
FIG. 14 is a flow chart illustrative of another exemplary embodiment of the methodology illustrated in FIG. 4 shown in greater detail.

With reference to FIG. 14, an exemplary tissue temperature prediction calculation will be described. For purposes of clarity, brevity, and illustration, the description below has been limited to an embodiment wherein the temperature is calculated based using the equation (9) above. It will be appreciated in view of the above, however, that the present disclosure is not meant to be limited to such an embodiment.

As an initial matter, in addition to being configured to calculate the predicted tissue temperature described above, in an exemplary embodiment, the ECU 34 is also configured to acquire and/or calculate the terms used in the equation for making the calculation (i.e., P(dt), φ, dt, (ln dt), (ln P), etc.). In this embodiment, the ECU 34 is configured to acquire magnitudes for the components of the complex impedance (i.e., X, R, Z, and $\phi$), the magnitudes of the instantaneous power (P) applied to the tissue 12, the elapsed time of the lesion formation process, and the temperature of the catheter tip.

More particularly, with reference to FIG. 14, the ECU 34 is configured to acquire magnitudes for the pre-ablation phase angle $\phi_1$ between the electrode 16 and the tissue 12 prior to the electrode 16 contacting the tissue 12, and the pre-ablation phase angle $\phi_2$ once the electrode 16 contacts the tissue 12 (Step 142). These magnitudes may be received from the complex impedance sensor 64, and may be stored along in a temporary or permanent memory or storage medium that is either part of, or accessible by, the ECU 34, such as, for example, the memory 73.

The ECU 34 is further configured to acquire magnitudes for X, R, Z, P, and the temperature (T) of the catheter tip at a point in time $t=t_2$ at which the depth of the lesion is assessed (the lesion formation process commencing at time $t=t_1$) (Step 144). The X, R, and Z magnitudes may be received from the complex impedance sensor 64, the P magnitude may be received from the ablation generator 26, or a reporting system associated therewith, and the T magnitude may be received from the temperature-sensing electrode or temperature sensor or the ablation generator 26. Each magnitude may be correlated and/or stored along with the corresponding time (i.e., $t=t_2$) in a memory or storage device such as that described above in the manner, for example, illustrated in FIG. 15. The ECU is still further configured to calculate the duration of the lesion formation process by calculating the change in time from when the lesion formation process commenced (i.e., time $t=t_1$), to when the temperature calculation is being made (i.e., time $t=t_2$, for example). The duration (dt) may then be stored in a memory or storage device as described above.

Because the temperature of the tissue may be assessed as the lesion is being formed such that the tissue temperature may be predicted/monitored in real-time, the ECU 34 is further configured to sample the magnitudes for X, R, Z, P, and T throughout the formation of the lesion at one or more respective predetermined sampling rates in order to constantly and continuously monitor the predicted temperature of the tissue. In an exemplary embodiment, a sampling rate on the order of 100 to 800 times per second may be used, however, the present disclosure is not meant to be limited to such a range of rates but rather a sampling rate that is greater than or less than 100 to 800 Hz may be used in different embodiments. Accordingly, the ECU 34 is configured to sample the signal received from the complex impedance sensor 64 at a predetermined rate and to store the corresponding X, R, and Z, magnitudes ($X_1, X_2, \ldots, X_n$; $R_1, R_2, \ldots, R_n$; and $Z_1, Z_2, \ldots, Z_n$) derived therefrom in the memory or storage medium described above along with the corresponding times (i.e., $t_1, t_2, \ldots, t_n$) at which the samples were taken (See FIG. 15). Similarly, the ECU 34 is configured to sample the signals received from the ablation generator 26, or an associated reporting system, and the temperature-sensing electrode or temperature sensor (in an embodiment wherein the temperature-sensing electrode or temperature sensor communicates with the ECU 34 directly) at a predetermined rate, and to store the corresponding power and temperature values ($P_1, P_2, \ldots, P_n$ and $T_1, T_2, \ldots, T_n$) in a memory such as that described above along with the corresponding times (i.e., $t_1, t_2, \ldots, t_n$) at which the samples were taken (See FIG. 15).

In an exemplary embodiment, after each set of samples of X, R, Z, P, and T is taken, the system 10 is configured to calculate the predicted tissue temperature described above. Alternatively, rather than calculating the predicted temperature after each set of samples, the ECU 34 may be configured to calculate the predicted temperature at some other rate such as after a certain number of sets of samples have been collected, after a certain amount of time has elapsed, upon receiving instructions from the user to do so, or after the lesion formation process has been completed. For the purposes of clarity and brevity alone, the description below will be directed to an embodiment wherein the predicted depth is calculated after a set of samples of each of the X, R, Z, P, and T is collected at a particular point in time, which, for this example, is time $t=t_2$. It will be appreciated, however that the present invention is not meant to be limited to such an embodiment.

Accordingly, after a set of samples of each of X, R, Z, P, and T are collected, the ECU 34 is configured to perform a number of calculations. For example, and as illustrated in FIG. 14, the ECU 34 is configured to calculate a change in the time (dt), or the elapsed time, represented by the time interval from the point in time that the lesion formation process commenced (i.e., time $t=t_1$, in this embodiment) to the point in time that the current sample was taken (i.e., time $t=t_2$) (Step 146). The ECU 34 is further configured to multiply the magnitude of the power ($P_2$) with the change in time (dt) (Step 148), to calculate the change in phase angle (d$\phi$) between $\phi_2$ and $\phi_1$ by subtracting $\phi_1$ from $\phi_2$ (Step 150), to calculate the natural log of the magnitude of the duration or change in time (dt) (Step 152), and to calculate the natural log of the power ($P_2$) applied to the tissue (Step 154).

Once all of the terms above are calculated, the ECU 34 is configured and able to calculate the predicted tissue temperature at that point in time (Step 156). Accordingly, using equation (9) above as an example, the ECU 34 is configured to acquire the correct or appropriate values for the constant a and the coefficients $b_1$-$b_9$, and to process these values with the terms described above to come to a predicted temperature of the tissue a predetermined depth below the surface of the tissue 12 (i.e., in this embodiment, 3 mm below the endocardial surface). Accordingly, the computer program stored or accessible by the ECU 34 includes code for carrying out the execution of the predicted temperature equation. Once the predicted temperature is calculated, it may be used in a number of ways, such as, for example, in the same manner as was described above in great detail for the calculated predicted lesion depth (i.e., the calculated temperature may be used and displayed in same manner as the calculated predicted lesion depth). Accordingly, the description above relating to the use and display of the predicted lesion depth applies here with equal force, and therefore, will not be repeated in its entirety.

However, for illustrative purposes only, in one exemplary embodiment, the ECU 34 is configured to generate a signal representative of an indicator or indication of the predicted temperature, and may be further configured to control a display, such as, for example, the display 36, to display the indicator represented by the signal generated by the ECU 34. In other words, the calculated temperature may be displayed for the user of the system 10 to see (Step 158). In one exemplary embodiment, the predicted tissue temperature may be displayed in numerical form (e.g., a digital readout) on the display 36 of the visualization, mapping, and navigation system 32, as generally illustrated in FIG. 8*a*. In other embodiments, the predicted tissue temperature may be displayed, not in numerical form (e.g., a digital readout), but as a visual representation indicative of the predicted tissue temperature. The visual representation 222 indicative of the predicted tissue temperature may comprise a graph (e.g., bar graph or graph of any other shape), a meter, a "stop light" design comprising three, vertically stacked circular images, an indicator needle, a "gas tank gauge," or any number of other visual representations that may be used to indicate a temperature. Although the visual representation of predicted tissue temperature is generally illustrated as a bar graph in FIG. 8c, any number of other visual representations may be used in accordance with other embodiments of the invention. Different colors, shapes, and/or sizes of images may be used as a visual representation 222 indicative of predicted tissue temperature. Although FIG. 8a includes only the numerical form of the tissue temperature on the display 36 of the visualization, mapping, and navigation system 32, both the numerical form and a visual representation 222 may be displayed in accordance with other embodiments of the system 10, as generally illustrated in FIG. 8c. In other embodiments, only the visual representation indicative of the predicted tissue temperature may be displayed. In addition to a visual representation indicative of the predicted tissue temperature, there may be other visual indications of the predicted tissue temperature such as messages, warnings, alerts, lights, color changes, blinking, specialized images, and/or any of other numerous visual indications known to those of ordinary skill in the art. In addition to and/or instead of the visual representation indicative of the predicted tissue temperature, there may also be at least one of an audible indication (e.g., buzzer, alarm, audible message, etc.), a tactile indication, and/or a vibrational indication of the predicted tissue temperature. The audible indication, tactile indication, and/or vibrational indication may be used in connection with the catheter 18 (e.g., handle 44) in order to provide feedback to the user (e.g., clinician or physician) of the system 10. For example, the audible indication, tactile indication, and/or vibrational indication may be presented if a value indicative of the predicted tissue temperature of the target tissue exceeds a predetermined threshold. The value of the predetermined threshold may be input into ECU 34 through the input interface of the ECU 34.

The temperature magnitude may also be displayed with the duration of time that the temperature has remained at that temperature, and/or along with a log of prior temperature calculations. This embodiment provides the physician or clinician using the system 10 with a real-time indication of tissue temperature. Accordingly, if the ECU 34 calculates the predicted tissue temperature at 3 mm below the surface of the tissue 12 is 50° C., a reading of "50° C." will be displayed on the display 36. Based on the displayed predicted temperature, and using his/her experience, the user of the system 10 may be able to interpret the displayed temperature to determine the depth of the lesion being formed at that particular location. More particularly, if the temperature reaches a predetermined magnitude, the user may be able to tell that the lesion has reached the depth to which the temperature corresponds. For example, if the calculated temperature corresponds to the predicted temperature of the tissue 3 mm below the surface of the tissue, based on the displayed calculated temperature, the user may be able to determine whether or not the lesion has reached a depth of 3 mm. Accordingly, rather than the system 10 predicting the lesion depth, in this embodiment, the system 10 predicts the temperature of the tissue a predetermined depth below the surface, and then the user of the system interprets the predicted temperature to assess the lesion depth for himself/ herself. Thus, the system 10 in this embodiment provides a tool that the user of the system 10 may use to assess lesion depth, as opposed to assessing lesion depth itself It will be appreciated that while the description above has been limited to an embodiment wherein the predicted temperature corresponds to the temperature of the tissue at a depth of 3 mm below the surface of the tissue, the present disclosure is not meant to be limited to such an embodiment. Rather, it is contemplated that the tissue temperature at depths greater than or less than 3 mm below the surface of the tissue may be predicted in a similar manner to that described above, and therefore, embodiments of the system 10 for predicting temperatures at depths other than 3 mm remain within the spirit and scope of the present disclosure.

Regardless of how the calculated predicted temperature is processed and/or displayed, once the predicted temperature has been calculated and evaluated for a set of samples taken at a predetermined point in time, in an exemplary embodiment, the system 10 may be configured to repeat the above-described process for a set of subsequent samples taken at a subsequent point in time in accordance with a predetermined rate of calculating the predicted temperature (i.e., for each set of samples taken for X, R, P, T, Z, and dt, for example; after a predetermined number of sets of samples are taken; after predetermined amount of time has elapsed, etc.). The process may be continuously repeated at a given rate until, for example, the physician or clinician terminates the process, or the lesion formation process has been otherwise stopped.

In another exemplary embodiment, the ECU 34 may be configured to generate a signal representative of an indicator or indication of a predicted likelihood of steam pop (or endocardial barotrauma), and may further be configured to control a display, such as, for example, the display 36, to display the indicator represented by the signal generated by the ECU 34. Steam pop is also referred to in the art as "tissue pop." Steam pop is well known to clinicians, physicians, electrophysiologists and other users of ablation systems. In particular, when the interface between the electrode 16 and the tissue 12 increases rapidly above the boiling point as a result of the energy applied to the tissue, it can vaporize water and/or blood, thus causing an audible pop. If the water and/or blood is contained within the tissue, the vaporization may cause disruption to the tissue. In particular, steam popping may result from the formation of bubbles within heated tissue, and the expansion and/or rupturing of tissue by these bubbles. Steam popping caused by the expansion of bubbles may result in the undesirable tearing of tissue and the release of emboli and/or micro-bubbles into blood.

Numerous factors may have an impact on the algorithm for the predicted likelihood of steam pop. These factors include, for example and without limitation: the reactance, the resistance, the impedance, and the phase angle components of the complex impedance between the electrode 16 and the tissue 12, the instantaneous power applied to the tissue 12 at the point in time for which the predicted likelihood of steam pop is made, the duration of the lesion formation process, the temperature of the tip of the catheter, and the calculated predicted temperature. Various other factors would possibly have an impact on the algorithm for the predicted likelihood of steam pop including, for example and without limitation, certain parameters and/or characteristics of the equipment and/or arrangement of the system 10 (such as, for example, the type of catheter and ablation generator being used, the irrigation flow rate, etc.), as well as the depth below the surface (e.g., endocardial surface) of the tissue 12 for which the temperature is being predicted.

Accordingly, a visual representation indicative of the predicted likelihood of steam pop may be displayed for the user of the system 10 to see. In one exemplary embodiment, the predicted likelihood of steam pop may be displayed as a percentage in numerical form (e.g., digital readout) on the display 36 of the visualization, mapping, and navigation system 32, as generally illustrated in FIG. 8a. In other embodiments, the predicted likelihood of steam pop may be displayed as a visual representation 224 comprising a graph (e.g., bar graph or graph of any other shape), meter, a "stop light" design comprising three, vertically stacked circular images, an indicator needle, a "gas tank gauge," or any number of other visual representations that may be indicative of the predicted likelihood of steam pop. Different colors, shapes, and/or sizes of images may be used as a visual representation indicative of the predicted likelihood of steam pop. Although FIG. 8a includes only the numerical form of the likelihood of steam pop on the display 36 of the visualization, mapping, and navigation system 32, both the numerical form and a visual representation 224 may be displayed in accordance with other embodiments of the system 10, as generally illustrated in FIG. 8c. In other embodiments, only the visual representation indicative of the predicted likelihood of steam pop may be displayed. In addition to a visual representation indicative of the predicted likelihood of steam pop as described above, there may be other visual indications of the predicted likelihood of steam pop such as messages, warnings, alerts, lights, color changes, blinking, specialized images, and/or any of other numerous visual indications known to those of ordinary skill in the art. For example, as generally illustrated in FIG. 8c, the visual representation 224 of predicted likelihood of steam pop may comprise a status message (e.g., "Steam pop likely" or "Steam pop not likely"). In addition to the visual representation 224 indicative of the predicted likelihood of steam pop, the system 10 may further include a sensitivity slider bar 223. The sensitivity slider bar 223 may be configured to allow the user to adjust the sensitivity of the system 10 with regard to the algorithm used in connection with the predicted likelihood of steam pop. Although a slider bar is described in detail, other interfaces may be used to adjust the sensitivity of the system 10 with regard to the predicted likelihood of steam pop. In particular, the sensitivity slider bar 223 may be used to change the level of the threshold against which the gathered data for steam pop prediction will be compared (i.e., a lower threshold may make it more likely that a steam pop will be predicted and the visual representation 224 will change from "Steam pop not likely" to "Steam pop likely," and a higher threshold may make is less likely that a steam pop will be predicted and the visual representation 224 will change from "Steam pop not likely" to "Steam pop likely."). Increased sensitivity (e.g., a lower threshold) may result in fewer false negative predictions, but more false positive predictions. Decreased sensitivity (e.g., a higher threshold) may result in fewer false positive predictions, but more false negative predictions. In addition to and/or instead of the visual representation indicative of the predicted likelihood of steam pop, there may also be at least one of an audible indication (e.g., buzzer, alarm, audible message, etc.), a tactile indication, and/or a vibrational indication of the predicted likelihood of steam pop. The audible indication, tactile indication, and/or vibrational indication may be used in connection with the catheter 18 (e.g., handle 44) in order to provide feedback to the user (e.g., clinician or physician) of the system 10. For example, the audible indication, tactile indication, and/or vibrational indication may be presented if a value indicative of the predicted likelihood of steam pop of the target tissue exceeds a predetermined threshold. The value of the predetermined threshold may be input into ECU 34 through the input interface of the ECU 34.

In accordance with another aspect of the disclosure, the system 10 may take the form of an automated catheter system 82, such as, for example and without limitation, a robotic catheter system or a magnetic-based catheter system. As will be described below, the automated catheter system 82 may be fully or partially automated, and so may allow for at least a measure of user control through a user input.

In the embodiment wherein the automated catheter system 82 is a robotic catheter system (i.e., robotic catheter system 82), a robot is used, for example, to control the movement of the catheter 18 and/or to carry out therapeutic, diagnostic, or other activities. In an exemplary embodiment, the robotic catheter system 82 may be configured such that information relating to the calculated predicted lesion depth and/or tissue temperature may be communicated from the ECU 34 to a controller or control system 84 of the robotic catheter system 82. In an exemplary embodiment, the ECU 34 and the controller 84 are one in the same. However, in another exemplary embodiment, the two are separate and distinct components. For ease of description purposes only, the following description will be directed to the latter, separate and distinct arrangement. It should be noted, however, that the embodiment wherein the controller 84 and the ECU 34 are the same remains within the spirit and scope of the present invention.

Figure 16:
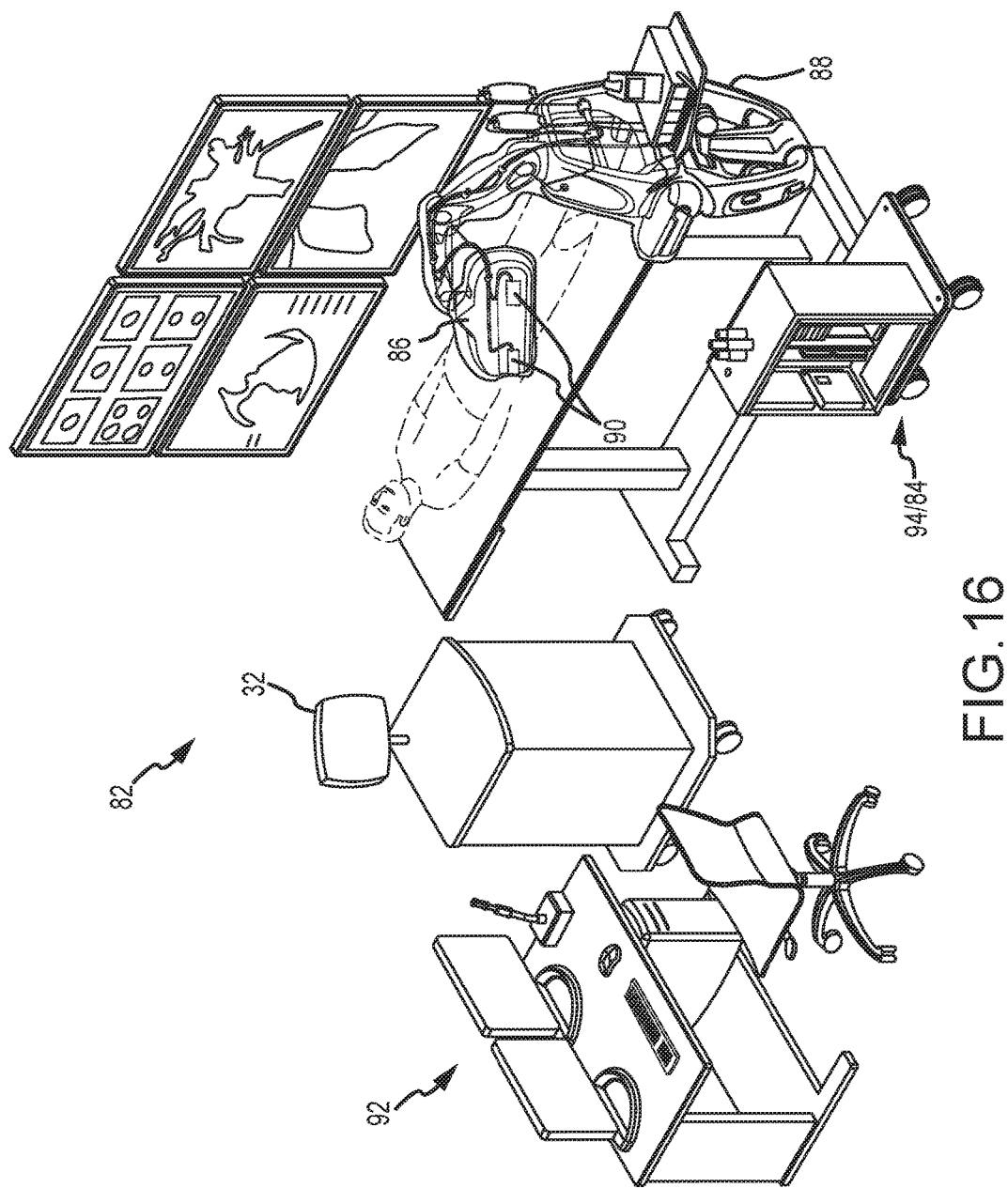
FIG. 16 is an isometric diagrammatic view of a robotic catheter system illustrating an exemplary layout of various system components in accordance with the present teachings.
Figure 17:
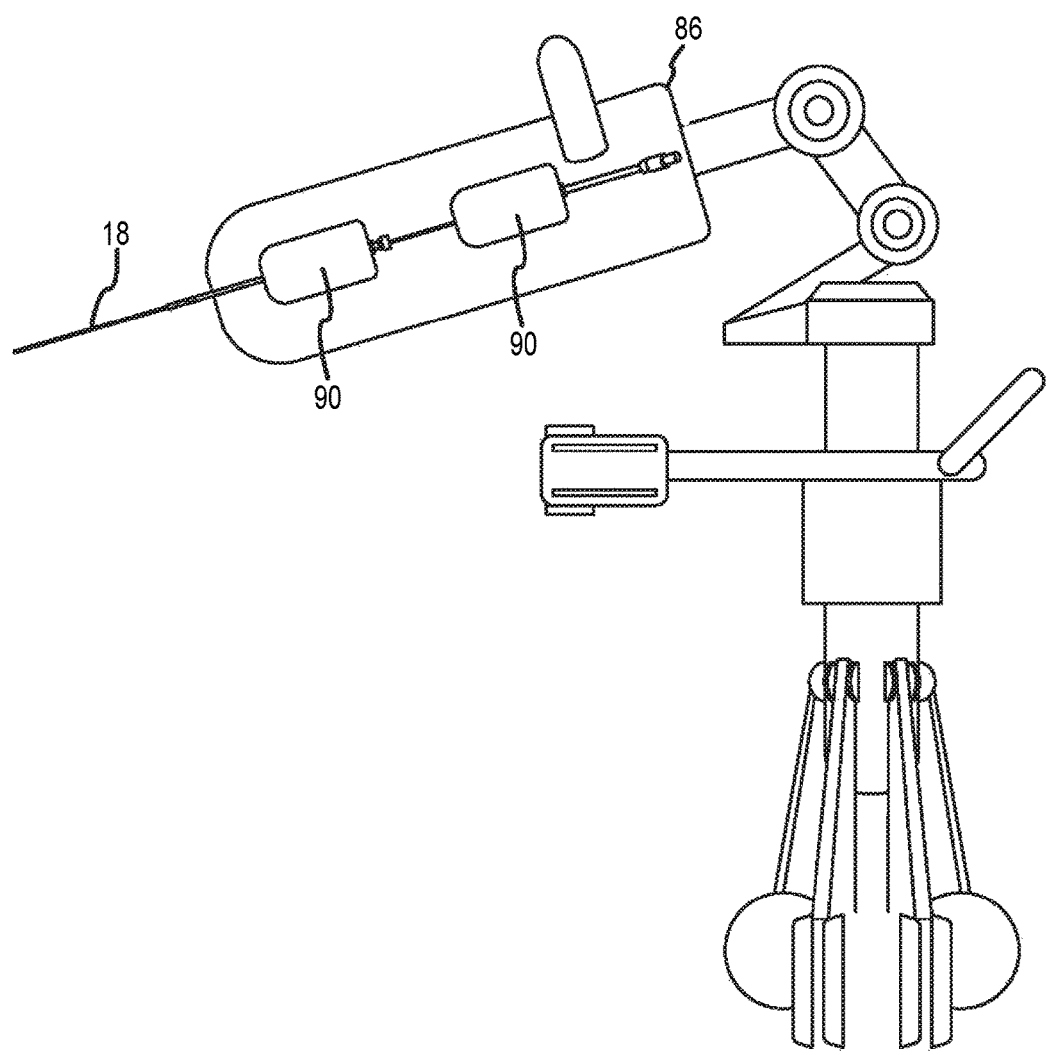
FIG. 17 is an isometric diagrammatic view of an exemplary embodiment of a robotic catheter manipulator support structure in accordance with the present teachings.

The information communicated to the controller 84 may be in the form of signal(s) generated by the ECU 34 that are representative of the predicted lesion depth or temperature. As will be described in greater detail below, the controller/control system 84 may use this information in the control and operation of the robotic catheter system 82. With reference to FIGS. 16 and 17, the robotic catheter system 82 will be briefly described. A full description of the robotic catheter system 82 is set forth in commonly-assigned and co-pending U.S. patent application Ser. No. 12/347,811 entitled "Robotic Catheter System," the disclosure of which is hereby incorporated by reference herein in its entirety.

Accordingly, FIGS. 16 and 17 illustrate the robotic catheter system 82. The robotic catheter system 82 provides the ability for precise and dynamic automated control in, for example, diagnostic, therapeutic, mapping, and ablative procedures. In an exemplary embodiment, the robotic catheter system 82 includes one or more robotic catheter manipulator assemblies 86 supported on a manipulator support structure 88. The robotic catheter manipulator assembly 86 may include one or more removably mounted robotic catheter device cartridges 90, for example, that are generally linearly movable relative to the robotic catheter manipulator assembly 86 to cause the catheter associated therewith (i.e., catheter 18) to be moved (e.g., advanced, retracted, etc.). The catheter manipulator assembly 86 serves as the mechanical control for the movements or actions of the cartridge 90. The robotic catheter system 82 may further include a human input device and control system ("input control system") 92, which may include a joystick and related controls with which a physician/clinician may interact to control the manipulation of the cartridge 90, and therefore, the catheter 18 of the system 82. The robotic catheter system 82 may still further include an electronic control system 94, which, in an exemplary embodiment, consists of or includes the controller 84, which translates motions of the physician/clinician at the input device into a resulting movement of the catheter. As with the system 10 described above, the robotic catheter system 82 may further include the visualization, mapping, and navigation system 32, to provide the clinician/physician with real-time or near-real-time positioning information concerning the catheter and various types of anatomical maps, models, and/or geometries of the cardiac structure of interest, for example.

In addition to, or instead of, the manual control provided by the input control system 92, the robotic catheter system 82 may involve automated catheter movement. For example, in one exemplary embodiment, a physician/clinician may identify locations (potentially forming a path) on a rendered computer model of the cardiac structure. The system 82 can be configured to relate those digitally selected points to positions within the patient's actual/physical anatomy, and may command and control the movement of the catheter 18 to defined positions. Once in a defined position, either the physician/clinician or the system 82 could perform desired treatment or therapy, or perform diagnostic evaluations. The system 82 could enable full robotic control by using optimized path planning routines together with the visualization, mapping, and navigation system 32.

As briefly described above, in an exemplary embodiment, information relating to the predicted lesion depth, the likelihood that a lesion has reached a predetermined depth, or predicted tissue temperature is input into controller 84 and may be used in the control and operation of the robotic catheter system 82. In an exemplary embodiment, the information is generated by, for example, the ECU 34 as described in great detail above. This information is then communicated by the ECU 34 to the controller 84. In one exemplary embodiment the information is simply stored within the robotic catheter system 82. Accordingly, no affirmative action is taken by the controller 84, or any other component of the robotic catheter system 82, in response to the information. In another exemplary embodiment, however, the information may be used by the robotic catheter system 82 to control one or more aspects of the operation of the system 82.

More particularly, in an exemplary embodiment, when it is determined, based on, for example, the calculated predicted lesion depth, that a lesion of a particular depth has been formed in the tissue 12, the controller 84 may be configured to retract or move the catheter 18 away from the tissue 12. The controller 84 may also be configured to cause the RF power being applied to the tissue 12 to be reduced or turned off completely. In such an instance, the controller 84 would be connected to the ablation generator 26 either directly or indirectly through, for example, the ECU 34 to allow communication between the controller 84 and the ablation generator 26 to reduce or turn-off the power applied to the tissue 12.

In another exemplary embodiment, instead of the controller 84 taking the affirmative steps to move away from the tissue or causing the power applied to the tissue 12 to be reduced or turned off, the controller 84 is configured to inquire as to whether the ablation procedure should go on, whether the controller 84 should move the catheter 18, whether the power should be reduced, etc. This inquiry may be directed to a physician/clinician, the ECU 34, or another component within the system 82. Depending on the feedback the controller 84 receives, it may take the necessary actions to carry out the instructions embodied by the feedback.

It will be appreciated that while the description thus far has been primarily with respect to an RF-based ablation system, the disclosure herein is not meant to be so limited. Rather, one of ordinary skill in the art will appreciate that the disclosure herein may find application with ablation systems other than RF-based ablation systems, such as, for example and without limitation, high intensity ultrasound (HIFU) ablation systems, cryogenic ablation systems, chemical ablation systems, and laser-based ablation systems. Accordingly ablation systems other than RF-based ablation systems remain within the spirit and scope of this disclosure.

Figure 18:
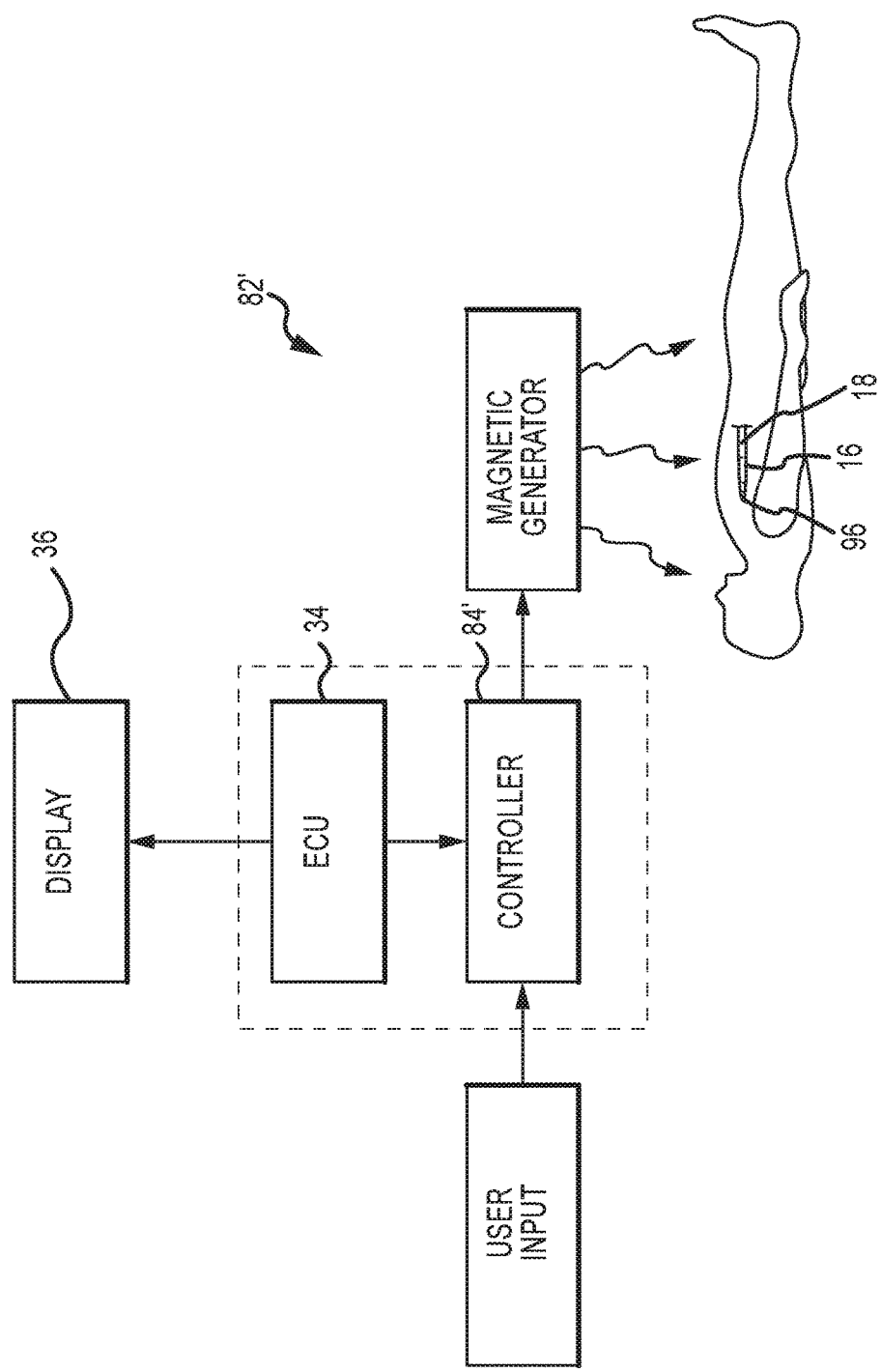
FIG. 18 is a schematic diagram of a magnetic-based catheter manipulation system in accordance with the present teachings.

With reference to FIG. 18, an exemplary embodiment of the automated catheter guidance system 82 comprising a magnetic-based catheter system (i.e., magnetic-based catheter system 82') is illustrated. In one exemplary embodiment, one or more externally generated magnetic fields produced by one or more electromagnets are used to move, guide, and/or steer a magnetically-tipped catheter through a patient's body. The externally generated magnetic fields exert a desired torque on the catheter to cause the position of the catheter to be manipulated in a desired way (e.g., advance, retract, bend, rotate, speed up, slow down, etc.). Accordingly, as with the robotic catheter system described above, the magnetic fields may be used to control the movement of the catheter 18 and/or to allow the system 10 to carry out therapeutic, diagnostic, or other activities at given locations within the patient's body. A full description of a magnetic-based catheter system is set forth in U.S. Pat. No. 6,507,751 entitled "Method and Apparatus Using Shaped Field of Repositionable Magnet to Guide Implant," and U.S. Published Patent Application No. 2007/0016006 A1 entitled "Apparatus and Method for Shaped Magnetic Field Control for Catheter, Guidance, Control, and Imaging," the disclosures of which are hereby incorporated by reference herein in their entireties.

In an exemplary embodiment, the magnetic-based catheter system 82' may be configured such that information relating to the calculated predicted lesion depth or tissue temperature, or the determination as to the likelihood that the lesion has reached a predetermined depth may be communicated from the ECU 34 to a controller or control system 84' of the magnetic-based catheter system 82'. In an exemplary embodiment, the ECU 34 and the controller 84' are one in the same. However, in another exemplary embodiment, the two are separate and distinct components. For ease of description purposes only, the following description will be directed to the latter, separate and distinct arrangement. It should be noted, however, that the embodiment wherein the controller 84' and the ECU 34 are the same remains within the spirit and scope of the present invention.

The information communicated to the controller 84' may be in the form of the signal(s) described above representative of the calculated lesion depth, tissue temperature, and/or likelihood that the lesion has reached a predetermined depth. As will be described in greater detail below, the controller/control system 84' may use this information in the control and operation of the magnetic-based catheter system 82'.

As with the robotic catheter system described above, the magnetic-based catheter system 82' provides the ability for precise and dynamic automated control in, for example, diagnostic, therapeutic, mapping, and ablative procedures. In an exemplary embodiment, the magnetic-based catheter system 82' includes somewhat similar structure to that of the robotic catheter system described above to effect the movement of the catheter 18. For example, system 82' may comprise a catheter manipulator assembly 86' that includes, in part, one or more external magnetic field generators configured to create the magnetic field(s) required to induce the movement of the catheter 18, and a magnetic element 96 mounted thereon or therein. The system 82' may further comprise support structures and the like to support catheter 18. As also with the robotic catheter system, the magnetic-based catheter system 82' may further include a human input device and control system ("input control system"), which may include a joystick and related controls with which a physician/clinician may interact to control the manipulation the catheter 18. In one exemplary embodiment, the system 82' is configured such that the physician or clinician may input a command for the catheter to move in a particular way. The system 82' processes that input and adjusts the strength and/or orientation of the external magnetic fields to cause the catheter 18 to move as commanded. The magnetic-based catheter system 82' may also still further include an electronic control system, which, as with the electronic control system of the robotic catheter system described above, may consist of or include the controller 84', that translates motions of the physician/clinician at the input device into a resulting movement of the catheter. Finally, in an exemplary embodiment, the magnetic-based catheter system 82' may further include the visualization, mapping and navigation system 32, to provide the clinician/physician with real-time or near-real-time positioning information concerning the catheter and various types of anatomical maps, models, and/or geometries of the cardiac structure of interest, for example.

As briefly described above, in an exemplary embodiment, information relating to the calculated lesion depth or tissue temperature, or the likelihood that the lesion has reached a predetermined depth, is input into controller 84' and may be used in the control and operation of the magnetic-based catheter system 82'. In an exemplary embodiment, the information is generated by, for example, the ECU 34 as described in great detail above. This information is then communicated by the ECU 34 to the controller 84'. In one exemplary embodiment the information is simply stored within the magnetic-based catheter system 82'. Accordingly, no affirmative action is taken by the controller 84', or any other component of the magnetic-based catheter system 82', in response to the information. In another exemplary embodiment, however, the information may be used by the magnetic-based catheter system 82' to control one or more aspects of the operation of the system 82'.

More particularly, in an exemplary embodiment, when it is determined, based on, for example, the calculated lesion depth, that a lesion of a particular depth has been formed, the controller 84' may be configured to retract or move the catheter 18 away from the tissue 12 by adjusting the strength and/or orientation of the external magnetic field. The controller 84' may also be configured to cause the RF power being applied to the tissue 12 to be reduced or turned off completely. In such an instance, the controller 84' would be connected to the ablation generator 26 either directly or indirectly through, for example, the ECU 34 to allow communication between the controller 84' and the ablation generator 26 to reduce or turn-off the power applied to the tissue 12.

In another exemplary embodiment, instead of the controller 84' taking the affirmative steps to move away from the tissue or causing the power applied to the tissue 12 to be reduced or turned off, the controller 84' is configured to inquire as to whether the ablation procedure should go on, whether the controller 84' should move the catheter 18, whether the power should be reduced, etc. This inquiry may be directed to a physician/clinician, the ECU 34, or another component within the system 82'. Depending on the feedback the controller 84' receives, it may take the necessary actions to carry out the instructions embodied by the feedback.

It will be appreciated that in addition to the structure of the system 10 and the article of manufacture described above, another aspect of the present disclosure is a method for assessing the formation of a lesion in tissue on which an ablation procedure is being performed is provided. With respect to FIG. 4, and in its most general form, the method includes a first step 100 of acquiring, by the ECU 34, one or more values for one or more components of a complex impedance between the electrode 16 and the tissue 12. A second step 102 includes acquiring, by the ECU 34, a value for the power applied to the tissue 12 during the formation of the lesion therein. A third step 104 includes calculating, by the ECU 34, a value responsive to the magnitudes for the one or more complex impedance components and the applied power, wherein the value is indicative of one of a predicted lesion depth, a likelihood that the lesion has reached a predetermined depth, and a predicted tissue temperature.

With reference to FIG. 6, a more detailed description of one exemplary embodiment of the method will be described. In this embodiment, the calculated value is indicative of a predicted lesion depth. In the interest of clarity and brevity, the methodology will be described solely with respect to equation (3) above. It will be appreciated, however, that the present disclosure is not meant to be limited solely to this prediction algorithm or methodology.

In such an embodiment, magnitudes for first and second components of the complex impedance are acquired. These components comprise resistance (R) and phase angle ($\phi$). Accordingly, in step 106, a magnitude of the pre-ablation phase angle between the electrode 16 and the tissue 12 is acquired by the ECU 34 corresponding to a point in time prior to the commencement of the lesion formation process (i.e., time $t=t_0$). Additionally, magnitudes for the resistance and the phase angle between the electrode 16 and the tissue 12 are acquired by the ECU 34 corresponding to a point in time at which the lesion formation process commences (i.e., just after initiation of RF power/energy delivery to the tissue 12) (i.e., time t=In step 108, magnitudes for the resistance and phase angle between the electrode 16 and the tissue 12 corresponding to the time at which the lesion depth is being predicted, as well as a magnitude of the average power applied to the tissue to that point in the lesion formation process, are acquired by the ECU 34.

In step 110, the ECU 34 calculates a change in resistance (dR) between the resistance magnitude corresponding to the point in time at which the lesion formation process commences (i.e., time $t=t_1$) and the resistance magnitude corresponding to the point in time at which the lesion depth is being predicted. In step 112, the ECU 34 calculates or determines a change in time (dt), or the amount of elapsed time between the start of the lesion formation process and the time at which the predicted depth is being calculated.

In step 114, the ECU 34 calculates a change in phase angle (d q5) between the phase angle magnitude corresponding to the point in time at which the lesion formation process commences (i.e., time $t=t_1$) and the phase angle magnitude corresponding to the point in time at which the lesion depth is being predicted.

In step 116, the natural log of the magnitude of the average power is calculated by the ECU 34.

Once each of the above described calculations are made, the ECU 34 is configured to acquire the appropriate values for the constant and coefficients of the predicted depth equation, and to then process these values with the calculations described above to calculate the predicted depth (Step 117). More particularly, step 117 includes summing a predetermined constant with: the product of a first coefficient and the natural log of the average power; the product of a second coefficient and the term (dt); the product of a third coefficient and the magnitude of the pre-ablation phase angle; the product of a fourth coefficient and the term dR; and the product of a fifth coefficient and the term dφ.

With continued reference to FIG. 6, in an exemplary embodiment, the method further includes a step 118 that includes generating, by the ECU 34, a signal or indicator representative of the calculated predicted lesion depth, and controlling, by the ECU 34, a display device, such as, for example, the display 36, to display the predicted lesion depth, or an indicator thereof, represented by the signal generated by the ECU 34. This display may be in the form of a numeric display, or some other form, such as, for example, markers on an image/model. The ECU 34 is further configured to repeat the above described methodology using R, φ, and Avg.P samples corresponding to a subsequent point in time in the lesion formation process.

With reference to FIGS. 9a and 9b, in another exemplary embodiment described in great detail above, rather than displaying the predicted lesion depth as described above, the method further includes a step 120 of setting at least one target lesion depth, and a step 122 of comparing the calculated predicted depth to the target. In this embodiment, the display step 118 of the method comprises displaying an indication to user as to whether the predicted depth meets, exceeds, or falls below the target. Accordingly, the ECU 34 is configured to compare the predicted depth to one or more targets, to generate one or more signals representative of one or more indicators corresponding to the result of the comparison(s), and to control the display 36 to display the indicator(s) represented by the generated signal(s). As with the embodiment above, once the indicator is displayed, the ECU 34 is configured to repeat the above described process for a subsequent set of samples.

With respect to FIG. 10, a more detailed description of another exemplary embodiment of the method of assessing the formation of a lesion in a tissue 12 will be provided. In this embodiment, the calculated value is indicative of a likelihood that the lesion has reached a predetermined depth. In the interest of clarity and brevity, the methodology will be described solely with respect to equation (7) above. It will be appreciated, however, that the present disclosure is not meant to be limited solely to this particular algorithm or methodology of assessing the likelihood that a lesion has reached a predetermined depth.

In such an embodiment, in step 124, magnitudes for the resistance ($R_1$) and reactance ($X_1$) between the tissue 12 and the electrode 16 at the point in time at which the lesion formation process commences (i.e., time $t=t_1$) are acquired, and an ECI ($ECI_1$) is calculated based on $R_1$ and $X_1$.

In step 126, magnitudes of the resistance ($R_2$) and reactance ($X_2$) between the tissue 12 and the electrode 16 at the point in time at which the lesion depth is assessed (i.e., time $t=t_2$) are acquired, and an ECI ($ECI_2$) is calculated based on $R_2$ and $X_2$.

In step 128, a magnitude for the average power (Avg.P) applied to the tissue 12 during the lesion formation process is acquired.

In step 130, a magnitude for the change in time between the onset of the lesion formation process and the time at which the lesion depth is assessed, or the duration of the lesion formation process, is calculated (dt); and in step 132, the natural log of the magnitude of the change in time (dt) is calculated.

In step 134, the change in the ECI between the onset of the lesion formation process and the time at which the lesion depth is assessed is calculated (dECI).

Once each of the above described calculations are made, the ECU 34 is configured to acquire the appropriate values for the constant and coefficients of the equation, and to then process these values with the calculations described above to calculate the value or index (Step 136). More particularly, step 136 includes summing a predetermined constant with: the product of a first coefficient and magnitude of the average power (Avg.P); the product of a second coefficient and the natural log of the magnitude of the change in time (dt); and the product of a third coefficient and the magnitude of the change in ECI (dECI).

With continued reference to FIG. 10, the method further includes a step 138 of comparing, by the ECU 34, the calculated value or index to a threshold, and generating a signal representative of an indicator that the depth is above or below the target depth based on the comparison of the value/index with the threshold. In an exemplary embodiment, the method further includes a step 140 of controlling, by the ECU 34, the display device to display the indicator represented by the generated signal. Additionally, in an exemplary embodiment, the method may further include a step 137 performed prior to the comparison step 138 that comprises adjusting the threshold value. More particularly, step 137 may include receiving, by the ECU 34, an input from a user input device, such as, for example, user input device 80, and then adjusting the threshold value in response to the user input.

In an exemplary embodiment, the system 10, and the ECU 34, in particular, is further configured to repeat the above described methodology using samples corresponding to a subsequent point in time in the lesion formation process.

In alternate exemplary embodiments, the method further includes, as described in greater detail above, one or more of the steps of: receiving, from a user input device, an input corresponding to the desired target depth (i.e., adjusting the target depth); receiving, from a user input device, an input corresponding to the desired sensitivity of the system (i.e., adjusting the threshold); and calculating a value or index for a second target depth simultaneous with the calculation of the value or index for a first target depth.

With reference to FIG. 14, a more detailed description of another exemplary embodiment of the method of assessing the formation of a lesion in a tissue 12 will be provided. In this embodiment, the calculated value is indicative of a predicted temperature of the tissue a predetermined depth below the surface of the tissue. In the interest of clarity and brevity, the methodology will be described solely with respect to equation (9) above. It will be appreciated, however, that the present disclosure is not meant to be limited solely to this prediction algorithm or methodology.

In such an embodiment, in step 142, magnitudes for the pre-ablation phase angle between the electrode 16 and the tissue 12 both prior to ($φ_1$) and following ($φ_2$) the catheter 18 contacting the tissue 12 are acquired. In step 144, magnitudes for the resistance, reactance, and impedance between the electrode 16 and the tissue 12, the magnitude of the instantaneous power applied to the tissue 12, and the magnitude of the temperature of the tip of the catheter 18, all corresponding to the time at which the temperature of the tissue is being predicted, are acquired by the ECU 34.

In step 146, the ECU 34 calculates or determines a change in time (dt), or the amount of elapsed time between the start of the lesion formation and the time at which the predicted temperature is being calculated. In step 148, the ECU 34 multiplies the magnitude of the instantaneous power with the change in time (dt).

In step 150, the ECU 34 calculates the change in pre-ablation phase angle (dφ) based on phase angle magnitudes φ₁ and φ₂.

In step 152, the natural log of the magnitude of change in time (dt) is calculated by the ECU 34; and in step 154, the natural log of the magnitude of the instantaneous power applied to the tissue 12 is calculated by the ECU 34.

Once each of the above described calculations are made, the ECU 34 is configured to acquire the appropriate values for the constant and coefficients of the predicted temperature equation, and to then process these values with the calculations described above to calculate the predicted temperature (Step 156). More particularly, step 156 includes summing a predetermined constant with: the product of a first coefficient and magnitude of the reactance (X); the product of a second coefficient and magnitude of the resistance (R); the product of a third coefficient and the magnitude of the power (P) applied to the tissue 12; the product of a fourth coefficient and the magnitude of the temperature of the catheter tip (T); the product of a fifth coefficient and the magnitude of the impedance (Z); the product of a sixth coefficient and the product of the power (P) applied to the tissue and the term (dt); the product of seventh coefficient and the term dφ; the product of an eighth coefficient and the natural log of the term (dt); and the product of a ninth coefficient and the natural log of the power applied to the tissue 12.

With continued reference to FIG. 14, in an exemplary embodiment, the method further includes a step 158 that includes generating, by the ECU 34, a signal or indicator representative of the calculated predicted temperature, and controlling, by the ECU 34, a display device, such as, for example, the display 36, to display the predicted temperature, or an indicator thereof, represented by the signal generated by the ECU 34. This display may be in the form of a numeric display, or some other form, such as, for example, markers on an image/model. The ECU 34 is further configured to repeat the above described methodology using samples corresponding to a subsequent point in time in the lesion formation process.

It should be noted that the processes described above are lesion-by-lesion processes. As such, for each new lesion that is performed during an ablation process (multiple lesions may be performed during a single ablation process), the values for the factors used in the equation(s) for calculating the value must be reevaluated and reset in order for the calculated values to be accurate. In order for the system 10, and the ECU 34, in particular, to know when a new lesion is being performed, and therefore, when to reset and/or reevaluate the appropriate values or factors, the system 10 may further include a means or mechanism for informing the ECU 34 that a new lesion formation process is commencing. In an exemplary embodiment, the system 10 includes a user input device, such as, for example and without limitation, a trigger mechanism on the handle 44 of the catheter 18, a button associated with the visualization, mapping, and navigation system 32, or a device such as that described above with respect to user input device 80, that is electrically connected to, and configured for communication with, the ECU 34 to allow the user to indicate when a new lesion formation process is commencing. Alternatively, this may be carried out algorithmically by having the system 32, for example, determine the start of a lesion based on detection of catheter stability or some other factor/attribute. In yet another embodiment, the system 10 is configured, based on the input to ECU 34 from the ablation generator 26, to determine when one lesion formation process is concluded, and when another lesion formation process is commencing. Accordingly, it is contemplated that any number of means or mechanisms could be used to inform the ECU 34 that a lesion formation process is about to commence, or has commenced, and each of these means/mechanisms remain within the spirit and scope of the present invention.

It should be understood that the system 10, particularly ECU 34, as described above may include conventional processing apparatus known in the art, capable of executing preprogrammed instructions stored in an associated memory, all performing in accordance with the functionality described herein. It is contemplated that the methods described herein, including without limitation the method steps of embodiments of the disclosure, will be programmed in a preferred embodiment, with the resulting software being stored in an associated memory and where so described, may also constitute the means for performing such methods. Implementation of the invention, in software, in view of the foregoing enabling description, would require no more than routine application of programming skills by one of ordinary skill in the art. Such a system may further be of the type having both ROM, RAM, a combination of non-volatile and volatile (modifiable) memory so that the software can be stored and yet allow storage and processing of dynamically produced data and/or signals.

Although several embodiments of this disclosure have been described above with a certain degree of particularity, those skilled in the art could make numerous alterations to the disclosed embodiments without departing from the scope of this disclosure. All directional references (e.g., upper, lower, upward, downward, left, right, leftward, rightward, top, bottom, above, below, vertical, horizontal, clockwise and counterclockwise) are only used for identification purposes to aid the reader's understanding of the present disclosure, and do not create limitations, particularly as to the position, orientation, or use of the system, article of manufacture and methodology of the present disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the disclosure as defined in the appended claims.

What is claimed is:

1. A system including a graphical user interface for displaying characteristics of target tissue during an ablation procedure, the system comprising:
   an electronic control unit (ECU) configured to:
      receive a signal indicative of a contact force measured between a first electrode and the target tissue for a time period, wherein the time period is a time during which ablation energy is applied to the target tissue;
      receive at least one characteristic of the target tissue;
      measure a temperature during the time period;
      determine a predicted depth value of a lesion in the target tissue based on each of the following: i) the time period, ii) the signal indicative of the contact force, and iii) the temperature;

associate the predicted depth value with the at least one characteristic of the target tissue; and
output the predicted depth value; and
a display device operatively connected to the ECU, wherein the display device is configured to receive the predicted depth value and display a visual representation of the predicted depth value and one or more colors associated with the predicted depth value of the lesion in the target tissue for the time period.

2. The system of claim 1, the ECU further configured to receive as an input data a complex impedance measured between a second electrode and the target tissue for the time period during the ablation procedure; and
determine a predicted depth value of a lesion in the target tissue based on each of the following: i) the time period, ii) the signal indicative of the contact force, iii) the temperature and iv) the complex impedance.

3. The system of claim 2, wherein the ECU is further configured to determine a predicted temperature of the tissue at a predetermined depth below a surface of the tissue using one or more of (i) components of the complex impedance, (ii) an instantaneous power, (iii) the time period, and (iv) the temperature.

4. The system of claim 1, wherein the one or more colors comprise a first color associated with a first range of predicted depth values of the lesion in the target tissue for the time period.

5. The system of claim 4, wherein the one or more colors further comprises a second color associated with a second range of predicted depth values of the lesion in the target tissue for the time period.

6. The system of claim 5, wherein the one or more colors further comprises a third color associated with a third range of predicted depth values of the lesion in the target tissue for the time period.

7. The system of claim 1, wherein the visual representation is displayed and continuously updated during the time period.

8. The system of claim 1, wherein the at least one characteristic of the target tissue comprises a thickness of the target tissue.

9. The system of claim 1, wherein the display device is further configured to display a visual representation indicative of an ablation catheter used to perform the ablation procedure.

10. The system of claim 9, wherein the visual representation indicative of the ablation catheter used to perform the ablation procedure includes a first view along a first axis of a body upon which the ablation procedure is performed and includes a second view along a second axis of the body upon which the ablation procedure is performed.

11. The system of claim 1, wherein the display device is further configured to display a visual representation indicative of the transmurality of a lesion in the targeted tissue.

12. The system of claim 1, wherein the ECU is configured to store the predicted depth value, to retrieve the stored predicted depth value subsequent to the time period, and to output the stored predicted depth value to the display device subsequent to the time period, and wherein the display device is configured to display a visual representation of the stored predicted depth value of the lesion in the target tissue subsequent to the time period.

13. The system of claim 1, wherein the display device is further configured to display a slider bar configured to adjust a threshold against which the predicted depth value of the lesion in the target tissue may be compared, thereby adjusting a sensitivity of the graphical user interface system.

14. A system including a graphical user interface for displaying characteristics of target tissue during an ablation procedure, the system comprising:
an ablation catheter comprising
a first sensor configured for obtaining data regarding a contact force measured between a first electrode and the target tissue for the time period, wherein the time period is a time during which ablation energy is applied to the target tissue,
a second sensor proximate a distal end of the ablation catheter configured for obtaining data regarding a temperature measured for the time period;
an electroanatomic visualization, mapping, and navigation system configured for generating an anatomical model of at least the target tissue, the electroanatomic visualization, mapping, and navigation system including a display device for displaying the anatomical model; and
a graphical user interface system comprising: an electronic control unit (ECU) configured to receive as an input data a signal indicative of the contact force for the time period; receive as an input an input data the temperature; determine a predicted depth value of a lesion in the target tissue based on each of the following: i) the time period, ii) the signal indicative of the contact force, and iii) the temperature; associate the predicted depth value with the thickness of the target tissue; and output the predicted depth value;
wherein the display device is operatively connected to the ECU and is configured to receive the predicted depth value and to display i) a visual representation of the predicted depth value of the lesion in the target tissue for the time period and ii) a visual representation of the thickness of the target tissue.

15. The system of claim 14, the ablation catheter further comprising
a third sensor configured for obtaining data regarding a complex impedance measured between a second electrode and the target tissue for a time period during the ablation procedure,
the ECU further configured to receive as an input data the complex impedance for the time period; receive as an input data a thickness of the target tissue; determine a predicted depth value of a lesion in the target tissue based on each of the following: i) the time period, ii) the signal indicative of the contact force, iii) the temperature, and iv) the complex impedance.

16. The system of claim 14, wherein the display device is further configured to display a visual representation indicative of a location of the ablation catheter used to perform the ablation procedure relative to the anatomical model generated by the electroanatomical model generated by the electroanatomical visualization, mapping, and navigation system.

17. The system of claim 14, wherein at least one of the display device and the ablation catheter is configured to present at least one of an audible indication, a tactile indication, and a vibrational indication if the predicted depth value of the lesion in the target tissue for the time period exceeds a predetermined threshold.

18. A method for displaying characteristics of target tissue during an ablation procedure, the method comprising:
obtaining data regarding a thickness of the target tissue;
displaying a visual representation indicative of the thickness of the target tissue;
obtaining data regarding a contact force measured between a first electrode and the target tissue for the time period, wherein the time period is a time during which ablation energy is applied to the target tissue;

obtaining data regarding a temperature measured within the time period proximate the target tissue;

determining a predicted depth value of a lesion in the target tissue based on each of the following: i) the time period, iii) the signal indicative of the contact force, and iii) the temperature;

associating the predicted depth value with the thickness of the target tissue; and displaying a visual representation of the predicted depth value of the lesion in the target tissue for the time period.

19. The method of claim 18, further comprising obtaining data regarding a complex impedance measured between a second electrode and the target tissue for a time period during the ablation procedure, determining a predicted depth value of a lesion in the target tissue based on each of the following: i) the time period, iii) the signal indicative of the contact force, iii) the temperature; and iv) the complex impedance.

* * * * *